US008759533B2

(12) United States Patent
Connolly et al.

(10) Patent No.: US 8,759,533 B2
(45) **Date of Patent: *Jun. 24, 2014**

(54) DI-AZETIDINYL DIAMIDE AS MONOACYLGLCEROL LIPASE INHIBITORS

(71) Applicant: Janssen Pharmaceutica, NV, Beerse (BE)

(72) Inventors: Peter J. Connolly, New Providence, NJ (US); Mark J. Macielag, Gwynedd Valley, PA (US); Bin Zhu, Newtown, PA (US)

(73) Assignee: Janssen Pharmaceutica NV (BE)

( * ) Notice: Subject to any disclaimer, the term of this patent is extended or adjusted under 35 U.S.C. 154(b) by 0 days.

This patent is subject to a terminal disclaimer.

(21) Appl. No.: 13/798,699

(22) Filed: Mar. 13, 2013

(65) Prior Publication Data

US 2013/0196968 A1 Aug. 1, 2013

Related U.S. Application Data

(62) Division of application No. 13/224,654, filed on Sep. 2, 2011.

(60) Provisional application No. 61/379,764, filed on Sep. 3, 2010.

(51) Int. Cl.

| | |
|---|---|
| ***A61K 31/4035*** | (2006.01) |
| ***A61K 31/423*** | (2006.01) |
| ***A61K 31/427*** | (2006.01) |
| ***A61K 31/397*** | (2006.01) |
| ***A61K 31/454*** | (2006.01) |
| ***C07D 401/14*** | (2006.01) |
| ***C07D 403/14*** | (2006.01) |
| ***C07D 409/14*** | (2006.01) |
| ***C07D 413/14*** | (2006.01) |
| ***C07D 417/14*** | (2006.01) |
| ***C07D 403/04*** | (2006.01) |
| ***C07D 513/04*** | (2006.01) |
| ***A61K 31/428*** | (2006.01) |
| ***A61K 31/429*** | (2006.01) |
| ***A61K 31/404*** | (2006.01) |

(52) U.S. Cl.
USPC ........... 548/153; 548/200; 548/465; 548/180; 548/953; 548/224; 548/181; 514/210.18

(58) Field of Classification Search
None
See application file for complete search history.

(56) References Cited

U.S. PATENT DOCUMENTS

| | | | | |
|---|---|---|---|---|
| 2004/0167224 | A1 | 8/2004 | Ozaki et al. | |
| 2006/0148844 | A1 | 7/2006 | Nakade et al. | |
| 2007/0142394 | A1 | 6/2007 | Solomon et al. | |
| 2007/0293496 | A1 | 12/2007 | Ozaki et al. | |
| 2010/0041651 | A1 | 2/2010 | Even et al. | |
| 2010/0324011 | A1 | 12/2010 | Bian et al. | |
| 2010/0324012 | A1 | 12/2010 | Bian et al. | |
| 2010/0324013 | A1 | 12/2010 | Bian et al. | |
| 2010/0324014 | A1 | 12/2010 | Bian et al. | |
| 2010/0324015 | A1 | 12/2010 | Chevalier et al. | |
| 2010/0324016 | A1 | 12/2010 | Flores et al. | |
| 2010/0331299 | A1 | 12/2010 | Bian et al. | |
| 2010/0331300 | A1 | 12/2010 | Bian et al. | |
| 2011/0015170 | A1 | 1/2011 | Bian et al. | |
| 2011/0015171 | A1 | 1/2011 | Bian et al. | |
| 2012/0058986 | A1* | 3/2012 | Connolly et al. | 514/210.18 |
| 2013/0196969 | A1 | 8/2013 | Connolly et al. | |

FOREIGN PATENT DOCUMENTS

| | | | |
|---|---|---|---|
| EP | 2180048 | A1 | 4/2010 |
| FR | 2915199 | | 10/2008 |
| WO | WO 98/37077 | A1 | 8/1998 |
| WO | WO 99/19297 | A1 | 4/1999 |
| WO | WO 00/63168 | A1 | 10/2000 |
| WO | WO 01/77101 | A1 | 10/2001 |
| WO | WO 2004/056800 | | 7/2004 |
| WO | WO 2006/097175 | | 9/2006 |
| WO | WO 2008/145842 | | 12/2008 |
| WO | WO 2009/132267 | | 10/2009 |
| WO | WO 2010/124121 | | 10/2010 |
| WO | WO 2012/030907 | | 3/2012 |

OTHER PUBLICATIONS

International Search Report re: PCT/US2011/049885 dated Oct. 6, 2011.

Benito et al., "Cannabinoid CB2 receptors in human brain inflammation", Brit J Pharmacol, 2008, vol. 153, pp. 277-285.

Ben-Shabat et al., "An entourage effect: inactive endogenous fatty acid glycerol esters enhance 2-arachidonoyl-glycerol cannabinoid activity", Eur J Pharmacol, 1998, vol. 353, pp. 23-31.

Cravatt et al.,"The Endogenous Cannabinoid System and Its Role in Nociceptive Behavior", J Neurobiol, 2004, vol. 61, pp. 149-160.

Comelli et al., "The inhibition of monoacylglycerol lipase by URB602 showed an anti-inflammatory and anti-nociceptive effect in a murine model of acute inflammation", Brit J Pharmacol, 2007, vol. 152, pp. 787-794.

Cavuoto et al.,"The expression of receptors for endocannabinoids in human and rodent skeletal muscle", Biochem Biophys Res Commun, 2007, vol. 364, pp. 105-110.

Devane et al., "Isolation and Structure of a Brain Constituent That Binds to the Cannabinoid Receptor", Science, 1992, vol. 258, pp. 1946-1949.

(Continued)

*Primary Examiner* — Laura L. Stockton
(74) *Attorney, Agent, or Firm* — Thomas J. Dodd

(57) ABSTRACT

Disclosed are compounds, compositions and methods for treating various diseases, syndromes, conditions and disorders, including pain. Such compounds are represented by Formula (I) as follows:

Formula (I)

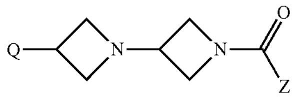

wherein Q and Z are defined herein.

12 Claims, No Drawings

(56) References Cited

OTHER PUBLICATIONS

Di Marzo et al., "Endocannabinoids: New Targets for Drug Development", Curr Pharm Des, 2000, vol. 6, pp. 1361-1380.
Di Marzo et al., "Endocannabinoids and the Regulation of their levels in Health and Disease", Curr Opin Lipidol, 2007, vol. 18, pp. 129-140.
Dogrul et al., "'Knock-down' of spinal CB1 receptors produces abnormal pain and elevates spinal dynorphin content in mice", Pain, 2002, vol. 100, pp. 203-209.
Guindon et al.,"Cannabinoid CB2 receptors: a therapeutic target for the treatment of inflammatory and neuropathic pain", Brit J Pharmacol, 2008, vol. 153, pp. 319-334.
Hajrasouliha et al., "Endogenous cannabinoids contribute to remote ischemic preconditioning via cannabinoid CB2 receptors in the rat heart", Eur J Pharmacol, 2008, vol. 579, pp. 246-252.
Jhaveri et al., "Endocannabinoid metabolism and uptake: novel targets for neuropathic and inflammatory pain", Brit J Pharmacol, 2007, vol. 152, pp. 624-632.
Kathuria et al., "Modulation of anxiety through blockade of anandamide hydrolysis", Nat Med, 2003, vol. 9, pp. 76-81.
Lichtman et al., "Pharmacological Activity of Fatty Acid Amides Is Regulated, but Not Mediated, by Fatty Acid Amide Hydrolase in Vivo", J Pharmacol Exp Ther, 2002, 302, 73-9.
Lichtman et al., "Mice lacking fatty acid amide hydrolase exhibit a cannabinoid receptor-mediated phenotypic hypoalgesia", Pain, 2004, vol. 109, pp. 319-327.
Matsuda et al., "Structure of a Cannabinoid Receptor and Functional Expression of the cloned cDNA", Nature, 1990, vol. 346, pp. 561-564.
Matulis, D., Kranz, J. K., Salemme, F. R., and Todd, M. J. (2005) *Biochemistry*, 44, 5258-66.
McCarberg B. et al., "The Future of Cannabinoids as Analgesic Agents: A Pharmacologic, Pharmacokinetic, and Pharmacodynamic Overview", Amer J Ther, 2007, vol. 14, pp. 475-483.
Mechoulam et al., "Identification of an Endogenous 2-Monoglyceride, Present in Canine Gut, that Binds to Cannabinoid Receptors", Biochem Pharmacol, 1995, vol. 50, pp. 83-90.
Munro et al., "Molecular Characterization of a Peripheral Receptor for Cannabinoids", Nature, 1993, vol. 365, pp. 61-65.
Njic, Ya Fatou et al, "Aqueous humor outflow effects of 2-arachidonylglycerol", Exp. Eye Res., 2008, vol. 87(2), pp. 106-114.
Pacher et al., "Pleiotropic effects of the $CB_2$ cannabinoid receptor activation on human monocyte migration: implications for atherosclerosis and inflammatory diseases", Amer J Physiol, 2008, vol. 294, pp. H1133-H1134.
Pantoliano et al., (2001) *J Biomol Screen* 6, 429-40.
Pertwee,"The diverse CB1 and CB2 receptor pharmacology of three plant cannabinoids: $\Delta^9$-tetrahydrocannabinol, cannabidiol and $\Delta^9$-tetrahydrocannabivarin", Brit J Pharmacol, 2008, vol. 153, pp. 199-215.
Piomelli, "The Molecular Logic of Endocannabinoid Signalling", Nat Rev Neurosci, 2003, vol. 4, pp. 873-884.
Sugiura et al., "2-Arachidonoylglycerol: A Possible Endogenous Cannabinoid Receptor Ligand in Brain", Biochem Biophys Res Commun, 1995, vol. 215, pp. 89-97.
Walker et al., "Pain modulation by release of the endogenous cannabinoid anandamide", Proc Natl Acad Sci USA, 1999, vol. 96, pp. 12198-12203.

* cited by examiner

DI-AZETIDINYL DIAMIDE AS MONOACYLGLCEROL LIPASE INHIBITORS

CROSS-REFERENCE TO RELATED APPLICATIONS

This application is a divisional of U.S. application Ser. No. 13/224,654, filed Sep. 2, 2011, currently pending, which claims priority to U.S. provisional patent application No. 61/379,764, filed Sep. 3, 2010, now abandoned, which are hereby incorporated by reference in their entirety.

STATEMENT REGARDING FEDERALLY SPONSORED RESEARCH OR DEVELOPMENT

The research and development of the invention described below was not federally sponsored.

BACKGROUND OF THE INVENTION

*Cannabis sativa* has been used for the treatment of pain for many years. $\Delta^9$-tetrahydrocannabinol is a major active ingredient from *Cannabis sativa* and an agonist of cannabinoid receptors (Pertwee, *Brit J Pharmacol,* 2008, 153, 199-215). Two cannabinoid G protein-coupled receptors have been cloned, cannabinoid receptor type 1 ($CB_1$ Matsuda et al., *Nature,* 1990, 346, 561-4) and cannabinoid receptor type 2 ($CB_2$ Munro et al., *Nature,* 1993, 365, 61-5). $CB_1$ is expressed centrally in brain areas, such as the hypothalamus and nucleus accumbens as well as peripherally in the liver, gastrointestinal tract, pancreas, adipose tissue, and skeletal muscle (Di Marzo et al., *Curr Opin Lipidol,* 2007, 18, 129-140). $CB_2$ is predominantly expressed in immune cells, such as monocytes (Pacher et al., *Amer J Physiol,* 2008, 294, H1133-H1134), and under certain conditions, also in the brain (Benito et al., *Brit J Pharmacol,* 2008, 153, 277-285) and in skeletal (Cavuoto et al., *Biochem Biophys Res Commun,* 2007, 364, 105-110) and cardiac (Hajrasouliha et al., *Eur J Pharmacol,* 2008, 579, 246-252) muscle. An abundance of pharmacological, anatomical and electrophysiological data, using synthetic agonists, indicate that increased cannabinoid signaling through $CB_1$/$CB_2$ promotes analgesia in tests of acute nociception and suppresses hyperalgesia in models of chronic neuropathic and inflammatory pain (Cravatt et al., *J Neurobiol,* 2004, 61, 149-60; Guindon et al., *Brit J Pharmacol,* 2008, 153, 319-334).

Efficacy of synthetic cannabinoid receptor agonists is well documented. Moreover, studies using cannabinoid receptor antagonists and knockout mice have also implicated the endocannabinoid system as an important modulator of nociception. Anandamide (AEA) (Devane et al., *Science,* 1992, 258, 1946-9) and 2-arachidinoylglycerol (2-AG) (Mechoulam et al., *Biochem Pharmacol,* 1995, 50, 83-90; Sugiura et al., *Biochem Biophys Res Commun,* 1995, 215, 89-97) are two major endocannabinoids. AEA is hydrolyzed by fatty acid amide hydrolase (FAAH) and 2-AG is hydrolyzed by monoacylglycerol lipase (MGL) (Piomelli, *Nat Rev Neurosci,* 2003, 4, 873-884). Genetic ablation of FAAH elevates endogenous AEA and results in a $CB_1$-dependent analgesia in models of acute and inflammatory pain (Lichtman et al., *Pain,* 2004, 109, 319-27), suggesting that the endocannabinoid system functions naturally to inhibit pain (Cravatt et al., *J Neurobiol,* 2004, 61, 149-60). Unlike the constitutive increase in endocannabinoid levels using FAAH knockout mice, use of specific FAAH inhibitors transiently elevates AEA levels and results in antinociception in vivo (Kathuria et al., *Nat Med,* 2003, 9, 76-81). Further evidence for an endocannabinoid-mediated antinociceptive tone is demonstrated by the formation of AEA in the periaqueductal grey following noxious stimulation in the periphery (Walker et al., *Proc Natl Acad Sci USA,* 1999, 96, 12198-203) and, conversely, by the induction of hyperalgesia following antisense RNA-mediated inhibition of $CB_1$ in the spinal cord (Dogrul et al., *Pain,* 2002, 100, 203-9).

With respect to 2-AG, intravenous delivery of 2-AG produces analgesia in the tail flick (Mechoulam et al., *Biochem Pharmacol,* 1995, 50, 83-90) and hot plate (Lichtman et al., *J Pharmacol Exp Ther,* 2002, 302, 73-9) assays. In contrast, it was demonstrated that 2-AG given alone is not analgesic in the hot plate assay, but when combined with other 2-monoacylglycerols (i.e., 2-linoleoyl glycerol and 2-palmitoyl glycerol), significant analgesia is attained, a phenomenon termed the "entourage effect" (Ben-Shabat et al., *Eur J Pharmacol,* 1998, 353, 23-31). These "entourage" 2-monoacylglycerols are endogenous lipids that are co-released with 2-AG and potentiate endocannabinoid signaling, in part, by inhibiting 2-AG breakdown, most likely by competition for the active site on MGL. This suggests that synthetic MGL Inhibitors will have a similar effect. Indeed, URB602, a relatively weak synthetic MGL Inhibitor, showed an antinociceptive effect in a murine model of acute inflammation (Comelli et al., *Brit J Pharmacol,* 2007, 152, 787-794).

Although the use of synthetic cannabinoid agonists have conclusively demonstrated that increased cannabinoid signaling produces analgesic and anti-inflammatory effects, it has been difficult to separate these beneficial effects from the unwanted side effects of these compounds. An alternative approach is to enhance the signaling of the endocannabinoid system by elevating the level of 2-AG, the endocannabinoid of highest abundance in the central nervous system (CNS) and gastrointestinal tract, which may be achieved by inhibition of MGL. Therefore, MGL inhibitors are potertially useful for the treatment of pain, inflammation, and CNS disorders (Di Marzo et al., *Curr Pharm Des,* 2000, 6, 1361-80; Jhaveri et al., *Brit J Pharmacol,* 2007, 152, 624-632; McCarberg Bill et al., *Amer J Ther,* 2007, 14, 475-83), as well as glaucoma and disease states arising from elevated intraocular pressure (Njie, Ya Fatou; He, Fang; Qiao, Zhuanhong; Song, Zhao-Hui, *Exp. Eye Res.,* 2008, 87(2):106-14).

SUMMARY OF THE INVENTION

The present invention is directed to a compound of Formula (I)

Formula (I)

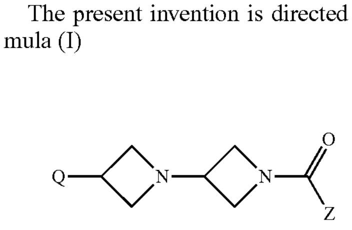

wherein

Q is selected from

Q1

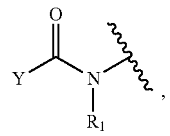

-continued

Q2

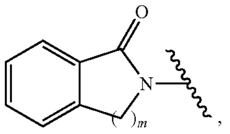

or

Q3

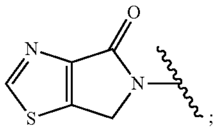

wherein

Y is $C_{6-10}$aryl or a heteroaryl that is thiazolyl, pyrrolyl, or oxazolyl;

$R^1$ is hydrogen or $C_{1-4}$ alkyl; and m is an integer from 1 to 3;

Z is $C_{6-10}$aryl or a heteroaryl selected from the group consisting of quinolinyl, benzothiophenyl, benzoxazolyl, benzothiazolyl, benzimidazolyl, indolyl, and indazolyl;

wherein Z is (i) optionally independently substituted with one to three substituents selected from the group consisting of $C_{1-4}$ alkyl, fluoro, chloro, bromo, trifluoromethyl, and piperidin-1-yl; provided that no more than one substituent on Z is piperidin-1-yl; or (ii) (a) substituted with

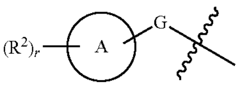

and (b) optionally further substituted with one additional methyl, chloro, fluoro, or phenyl substituent;

wherein ring A is phenyl, thienyl, or benzothiophenyl; provided that when ring A is thienyl or benzothiophenyl, G is a bond or $-CH_2-$; or when ring A is phenyl, G is selected from the group consisting of a bond, O, $-CH_2-$, $SO_2$, and C(O); and $R^2$ is trifluoromethyl, fluoro, chloro, or methanesulfonyl;

r is an integer from 0 to 3;

and enantiomers, diastereomers, solvates and pharmaceutically acceptable salts thereof.

The present invention also provides, inter alia, a pharmaceutical composition comprising, consisting of and/or consisting essentially of a pharmaceutically acceptable carrier, a pharmaceutically acceptable excipient, and/or a pharmaceutically acceptable diluent, and a compound of Formula (I), or a pharmaceutically acceptable salt form thereof.

Also provided are processes for making a pharmaceutical composition comprising, consisting of, and/or consisting essentially of admixing a compound of Formula (I) and a pharmaceutically acceptable carrier, a pharmaceutically acceptable excipient, and/or a pharmaceutically acceptable diluent.

The present invention further provides, inter alia, methods for treating or ameliorating a MGL-modulated disorder in a subject, including a human or other mammal in which the disease, syndrome, or condition is affected by the modulation of the MGL enzyme, such as pain and the diseases that lead to such pain, inflammation and CNS disorders, using a compound of Formula (I).

The present invention also provides, inter alia, methods for producing the instant compounds and pharmaceutical compositions and medicaments thereof.

DETAILED DESCRIPTION OF THE INVENTION

With reference to substituents, the term "independently" refers to the situation where when more than one substituent is possible, the substituents may be the same or different from each other.

The term "alkyl" whether used alone or as part of a substituent group, refers to straight and branched carbon chains having 1 to 8 carbon atoms. Therefore, designated numbers of carbon atoms (e.g., $C_{1-8}$) refer independently to the number of carbon atoms in an alkyl moiety or to the alkyl portion of a larger alkyl-containing substituent. In substituent groups with multiple alkyl groups, such as, $(C_{1-6}alkyl)_2$amino-, the $C_{1-6}$alkyl groups of the dialkylamino may be the same or different.

The term "alkoxy" refers to an —O-alkyl group, wherein the term "alkyl" is as defined above.

The terms "alkenyl" and "alkynyl" refer to straight and branched carbon chains having 2 or more carbon atoms, wherein an alkenyl chain contains at least one double bond and an alkynyl chain contains at least one triple bond.

The term "cycloalkyl" refers to saturated or partially saturated, monocyclic or polycyclic hydrocarbon rings of 3 to 14 carbon atoms. Examples of such rings include cyclopropyl, cyclobutyl, cyclopentyl, cyclohexyl, cycloheptyl and adamantyl.

The term "benzo-fused cycloalkyl" refers to a 5- to 8-membered monocyclic cycloalkyl ring fused to a benzene ring. The carbon atom ring members that form the cycloalkyl ring may be fully saturated or partially saturated.

The term "heterocyclyl" refers to a nonaromatic monocyclic or bicyclic ring system having 3 to 10 ring members and which contains carbon atoms and from 1 to 4 heteroatoms independently selected from the group consisting of N, O, and S. Included within the term heterocyclyl is a nonaromatic cyclic ring of 5 to 7 members in which 1 to 2 members are nitrogen, or a nonaromatic cyclic ring of 5 to 7 members in which 0, 1 or 2 members are nitrogen and up to 2 members are oxygen or sulfur and at least one member must be either nitrogen, oxygen or sulfur; wherein, optionally, the ring contains zero to one unsaturated bonds, and, optionally, when the ring is of 6 or 7 members, it contains up to 2 unsaturated bonds. The carbon atom ring members that form a heterocycle ring may be fully saturated or partially saturated. The term "heterocyclyl" also includes two 5 membered monocyclic heterocycloalkyl groups bridged to form a bicyclic ring. Such groups are not considered to be fully aromatic and are not referred to as heteroaryl groups. When a heterocycle is bicyclic, both rings of the heterocycle are non-aromatic and at least one of the rings contains a heteroatom ring member. Examples of heterocycle groups include, and are not limited to, pyrrolinyl (including 2H-pyrrole, 2-pyrrolinyl or 3-pyrrolinyl), pyrrolidinyl, imidazolinyl, imidazolidinyl, pyrazolinyl, pyrazolidinyl, piperidinyl, morpholinyl, thiomorpholinyl, and piperazinyl. Unless otherwise noted, the heterocycle is attached to its pendant group at any heteroatom or carbon atom that results in a stable structure.

The term "benzo-fused heterocyclyl" refers to a 5 to 7 membered monocyclic heterocycle ring fused to a benzene ring. The heterocycle ring contains carbon atoms and from 1 to 4 heteroatoms independently selected from the group consisting of N, O, and S. The carbon atom ring members that form the heterocycle ring may be fully saturated or partially saturated. Unless otherwise noted, benzo-fused heterocycle ring is attached to its pendant group at a carbon atom of the benzene ring.

The term “aryl” refers to an unsaturated, aromatic monocyclic or bicyclic ring of 6 to 10 carbon members. Examples of aryl rings include phenyl and naphthalenyl.

The term “heteroaryl” refers to an aromatic monocyclic or bicyclic aromatic ring system having 5 to 10 ring members and which contains carbon atoms and from 1 to 4 heteroatoms independently selected from the group consisting of N, O, and S. Included within the term heteroaryl are aromatic rings of 5 or 6 members wherein the ring consists of carbon atoms and has at least one heteroatom member. Suitable heteroatoms include nitrogen, oxygen, and sulfur. In the case of 5 membered rings, the heteroaryl ring preferably contains one member of nitrogen, oxygen or sulfur and, in addition, up to 3 additional nitrogens. In the case of 6 membered rings, the heteroaryl ring preferably contains from 1 to 3 nitrogen atoms. For the case wherein the 6 membered ring has 3 nitrogens, at most 2 nitrogen atoms are adjacent. Examples of heteroaryl groups include furyl, thienyl, pyrrolyl, oxazolyl, thiazolyl, imidazolyl, pyrazolyl, isoxazolyl, isothiazolyl, oxadiazolyl, triazolyl, thiadiazolyl, pyridinyl, pyridazinyl, pyrimidinyl, pyrazinyl, indolyl, isoindolyl, benzofuryl, benzothienyl, indazolyl, benzimidazolyl, benzothiazolyl, benzoxazolyl, benzisoxazolyl, benzothiadiazolyl, benzotriazolyl, quinolinyl, isoquinolinyl and quinazolinyl. Unless otherwise noted, the heteroaryl is attached to its pendant group at any heteroatom or carbon atom that results in a stable structure.

The term “halogen” or “halo” refers to fluorine, chlorine, bromine and iodine.

The term “formyl” refers to the group —C(=O)H.

The term “oxo” refers to the group (=O).

Whenever the term “alkyl” or “aryl” or either of their prefix roots appear in a name of a substituent (e.g., arylalkyl, alkylamino) the name is to be interpreted as including those limitations given above for “alkyl” and “aryl.” Designated numbers of carbon atoms (e.g., $C_1$-$C_6$ and $C_{1-6}$, which are synonymous) refer independently to the number of carbon atoms in an alkyl moiety, an aryl moiety, or in the alkyl portion of a larger substituent in which alkyl appears as its prefix root. For alkyl and alkoxy substituents, the designated number of carbon atoms includes all of the independent members included within a given range specified. For example, $C_{1-6}$ alkyl would include methyl, ethyl, propyl, butyl, pentyl and hexyl individually as well as sub-combinations thereof (e.g., $C_{1-2}$, $C_{1-3}$, $C_{1-4}$, $C_{1-5}$, $C_{2-6}$, $C_{3-6}$, $C_{4-6}$, $C_{5-6}$, $C_{2-5}$, etc.).

In general, under standard nomenclature rules used throughout this disclosure, the terminal portion of the designated side chain is described first followed by the adjacent functionality toward the point of attachment. Thus, for example, a “$C_1$-$C_6$ alkylcarbonyl” substituent refers to a group of the formula:

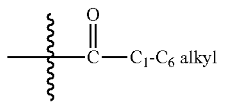

The term “R” at a stereocenter designates that the stereocenter is purely of the R-configuration as defined in the art; likewise, the term “S” means that the stereocenter is purely of the S-configuration. As used herein, the terms “*R” or “*S” at a stereocenter are used to designate that the stereocenter is of pure but unknown configuration. As used herein, the term “RS” refers to a stereocenter that exists as a mixture of the R- and S-configurations. Similarly, the terms “*RS” or “*SR” refer to a stereocenter that exists as a mixture of the R- and S-configurations and is of unknown configuration relative to another stereocenter within the molecule.

Compounds containing one stereocenter drawn without a stereo bond designation are a mixture of 2 enantiomers. Compounds containing 2 stereocenters both drawn without stereo bond designations are a mixture of 4 diastereomers. Compounds with 2 stereocenters both labeled “RS” and drawn with stereo bond designations are a 2-component mixture with relative stereochemistry as drawn. Compounds with 2 stereocenters both labeled “*RS” and drawn with stereo bond designations are a 2-component mixture with relative stereochemistry unknown. Unlabeled stereocenters drawn without stereo bond designations are a mixture of the R- and S-configurations. For unlabeled stereocenters drawn with stereo bond designations, the absolute stereochemistry is as depicted.

Unless otherwise noted, it is intended that the definition of any substituent or variable at a particular location in a molecule be independent of its definitions elsewhere in that molecule. It is understood that substituents and substitution patterns on the compounds of Formula (I), including Formulas (Ia), (Ib), and (Ic), can be selected by one of ordinary skill in the art to provide compounds that are chemically stable and that can be readily synthesized by techniques known in the art as well as those methods set forth herein.

The term “subject” refers to an animal, preferably a mammal, most preferably a human, who has been the object of treatment, observation or experiment.

The term “therapeutically effective amount” refers to an amount of an active compound or pharmaceutical agent, including a compound of the present invention, which elicits the biological or medicinal response in a tissue system, animal or human that is being sought by a researcher, veterinarian, medical doctor or other clinician, which includes alleviation or partial alleviation of the symptoms of the disease, syndrome, condition, or disorder being treated.

The term “composition” refers to a product that includes the specified ingredients in therapeutically effective amounts, as well as any product that results, directly, or indirectly, from combinations of the specified ingredients in the specified amounts.

The term “MGL inhibitor” is intended to encompass a compound that interacts with MGL to substantially reduce or eliminate its catalytic activity, thereby increasing the concentrations of its substrate(s).

The term “MGL-modulated” is used to refer to the condition of being affected by the modulation of the MGL enzyme including the condition of being affected by the inhibition of the MGL enzyme, such as, for example, pain and the diseases that lead to such pain, inflammation and CNS disorders.

As used herein, unless otherwise noted, the term “affect” or “affected” (when referring to a disease, syndrome, condition or disorder that is affected by the inhibition of MGL) shall include a reduction in the frequency and/or severity of one or more symptoms or manifestations of said disease, syndrome, condition or disorder; and/or include the prevention of the development of one or more symptoms or manifestations of said disease, syndrome, condition or disorder or the development of the disease, condition, syndrome or disorder.

The compounds of Formula (I), including Formulas (Ia), (Ib), and (Ic), are useful in methods for treating, ameliorating and/or preventing a disease, a syndrome, a condition or a disorder that is affected by the inhibition of MGL. Such methods comprise, consist of and/or consist essentially of administering to a subject, including an animal, a mammal, and a human in need of such treatment, amelioration and/or prevention, a therapeutically effective amount of a compound of Formula (I), including Formulas (Ia), (Ib), and (Ic), or an enantiomer, diastereomer, solvate or pharmaceutically acceptable salt form thereof. In particular, the compounds of Formula (I), including Formulas (Ia), (Ib), and (Ic), are useful for treating, ameliorating and/or preventing pain; diseases, syndromes, conditions, or disorders causing such pain; inflammation and/or CNS disorders. More particularly, the compounds of Formula (I), including Formulas (Ia), (Ib), and (Ic), are useful for treating, ameliorating and/or preventing inflammatory pain, inflammatory hypersensitivity conditions and/or neuropathic pain, comprising administering to a subject in need thereof a therapeutically effective amount of a compound of Formula (I), including Formulas (Ia), (Ib), and (Ic), as herein defined.

Examples of inflammatory pain include pain due to a disease, condition, syndrome, disorder, or a pain state including inflammatory bowel disease, visceral pain, migraine, post operative pain, osteoarthritis, rheumatoid arthritis, back pain, lower back pain, joint pain, abdominal pain, chest pain, labor, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis, pain due to physical trauma, headache, sinus headache, tension headache, or arachnoiditis.

One type of inflammatory pain is inflammatory hyperalgesia/hypersensitivity. Examples of inflammatory hyperalgesia include a disease, syndrome, condition, disorder, or pain state including inflammation, osteoarthritis, rheumatoid arthritis, back pain, joint pain, abdominal pain, musculoskeletal diseases, skin diseases, post operative pain, headaches, toothache, burn, sunburn, insect sting, neurogenic bladder, urinary incontinence, interstitial cystitis, urinary tract infection, cough, asthma, chronic obstructive pulmonary disease, rhinitis, contact dermatitis/hypersensitivity, itch, eczema, pharyngitis, enteritis, irritable bowel syndrome, inflammatory bowel diseases including Crohn's Disease, ulcerative colitis, urinary incontinence, benign prostatic hypertrophy, cough, asthma, rhinitis, nasal hypersensitivity, itch, contact dermatitis and/or dermal allergy and chronic obstructive pulmonary disease.

In an embodiment, the present invention is directed to a method for treating, ameliorating and/or preventing inflammatory visceral hyperalgesia in which an enhanced visceral irritability exists, comprising, consisting of, and/or consisting essentially of the step of administering to a subject in need of such treatment a therapeutically effective amount of a compound, salt or solvate of Formula (I), including Formulas (Ia), (Ib), and (Ic). In a further embodiment, the present invention is directed to a method for treating inflammatory somatic hyperalgesia in which a hypersensitivity to thermal, mechanical and/or chemical stimuli exists, comprising administering to a mammal in need of such treatment a therapeutically effective amount of a compound of Formula (I), including Formulas (Ia), (Ib), and (Ic), or an enantiomer, diastereomer, solvate or pharmaceutically acceptable salt thereof.

A further embodiment of the present invention is directed to a method for treating, ameliorating and/or preventing neuropathic pain. Examples of a neuropathic pain include pain due to a disease, syndrome, condition, disorder, or pain state including cancer, neurological disorders, spine and peripheral nerve surgery, brain tumor, traumatic brain injury (TBI), spinal cord trauma, chronic pain syndrome, fibromyalgia, chronic fatigue syndrome, lupus, sarcoidosis, peripheral neuropathy, bilateral peripheral neuropathy, diabetic neuropathy, central pain, neuropathies associated with spinal cord injury, stroke, amyotrophic lateral sclerosis (ALS), Parkinson's disease, multiple sclerosis, sciatic neuritis, mandibular joint neuralgia, peripheral neuritis, polyneuritis, stump pain, phantom limb pain, bony fractures, oral neuropathic pain, Charcot's pain, complex regional pain syndrome I and II (CRPS I/II), radiculopathy, Guillain-Barre syndrome, meralgia paresthetica, burning-mouth syndrome, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, postherpetic neuralgia, causalgia, red neuralgia, Sluder's neuralgia, splenopalatine neuralgia, supraorbital neuralgia, trigeminal neuralgia, vulvodynia, or vidian neuralgia.

One type of neuropathic pain is neuropathic cold allodynia, which can be characterized by the presence of a neuropathy-associated allodynic state in which a hypersensitivity to cooling stimuli exists. Examples of neuropathic cold allodynia include allodynia due to a disease, condition, syndrome, disorder or pain state including neuropathic pain (neuralgia), pain arising from spine and peripheral nerve surgery or trauma, traumatic brain injury (TBI), trigeminal neuralgia, postherpetic neuralgia, causalgia, peripheral neuropathy, diabetic neuropathy, central pain, stroke, peripheral neuritis, polyneuritis, complex regional pain syndrome I and II (CRPS I/II) and radiculopathy.

In a further embodiment, the present invention is directed to a method for treating, ameliorating and/or preventing neuropathic cold allodynia in which a hypersensitivity to a cooling stimuli exists, comprising, consisting of, and/or consisting essentially of the step of administering to a subject in need of such treatment a therapeutically effective amount of a compound of Formula (I), including Formulas (Ia), (Ib), and (Ic), or an enantiomer, diastereomer, solvate or pharmaceutically acceptable salt thereof.

In a further embodiment, the present invention is directed to a method for treating, ameliorating and/or preventing CNS disorders. Examples of CNS disorders include anxieties, such as social anxiety, post-traumatic stress disorder, phobias, social phobia, special phobias, panic disorder, obsessive-compulsive disorder, acute stress disorder, separation anxiety disorder, and generalized anxiety disorder, as well as depression, such as major depression, bipolar disorder, seasonal affective disorder, post natal depression, manic depression, and bipolar depression.

Embodiments of the present invention include a compound of Formula (I)

Formula (I)

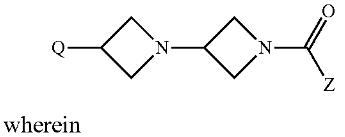

wherein a) Q is selected from

Q1

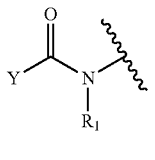
,

-continued

Q2

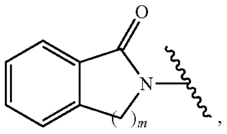

, or

Q3

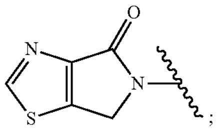

;

wherein

Y is phenyl or thiazolyl;

$R^1$ is hydrogen or methyl; and m is 1;

b) Q is selected from

Q1

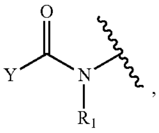

,

Q2

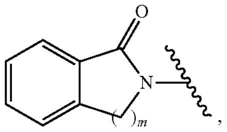

, or

Q3

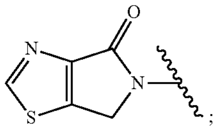

;

wherein

Y is phenyl or thiazolyl;

$R^1$ is hydrogen; and m is 1;

c) Z is $C_{6-10}$aryl or a heteroaryl selected from the group consisting of benzothiophenyl, benzoxazolyl, benzothiazolyl, indolyl, and indazolyl;

wherein Z is (i) optionally independently substituted with one to two substituents selected from the group consisting of $C_{1-4}$ alkyl, fluoro, chloro, bromo, trifluoromethyl, and piperidin-1-yl; provided that no more than one substituent on Z is piperidin-1-yl; or (ii) (a) substituted with

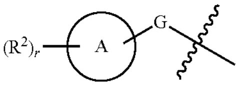

and (b) optionally further substituted with one additional methyl, chloro, fluoro, or phenyl substituent;

wherein ring A is phenyl, thienyl, or benzothiophenyl; provided that when ring A is thienyl or benzothiophenyl, G is a bond or —$CH_2$—; or when ring A is phenyl, G is selected from the group consisting of a bond, O, —$CH_2$—, $SO_2$, or C(O);

$R^2$ is trifluoromethyl, fluoro, chloro, or methanesulfonyl;

r is an integer from 0 to 3;

d) Z is $C_{6-10}$aryl or a heteroaryl selected from the group consisting of benzothiophenyl, benzoxazolyl, benzothiazolyl, indolyl, and indazolyl;

wherein Z is (i) optionally independently substituted with one to two substituents selected from the group consisting of $C_{1-4}$ alkyl, fluoro, chloro, bromo, and trifluoromethyl; or (ii) (a) substituted with

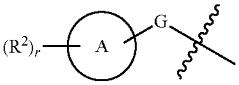

and (b) optionally further substituted with one additional methyl, chloro, fluoro, or phenyl substituent;

wherein ring A is phenyl or thienyl; provided that when ring A is thienyl, G is a bond or —$CH_2$—; or when ring A is phenyl, G is selected from the group consisting of a bond, —$CH_2$—, or $SO_2$;

$R^2$ is trifluoromethyl, fluoro, chloro, or methanesulfonyl;

r is an integer from 0 to 2;

and any combination of embodiments a) through d) above, provided that it is understood that combinations in which different embodiments of the same substituent would be combined are excluded;

and enantiomers, diastereomers, solvates and pharmaceutically acceptable salts thereof.

An embodiment of the present invention is directed to a compound of Formula (I)

Formula (I)

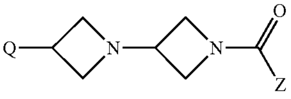

wherein:

Q is selected from

Q1

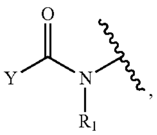

,

Q2

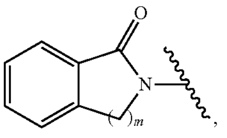

, or

-continued

Q3

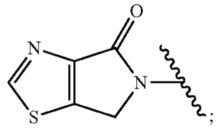

wherein

Y is phenyl or thiazolyl;

$R^1$ is hydrogen or methyl; and m is 1;

Z is $C_{6-10}$aryl or a heteroaryl selected from the group consisting of benzothiophenyl, benzoxazolyl, benzothiazolyl, indolyl, and indazolyl;

wherein Z is (i) optionally independently substituted with one to two substituents selected from the group consisting of $C_{1-4}$ alkyl, fluoro, chloro, bromo, trifluoromethyl, and piperidin-1-yl; provided that no more than one substituent on Z is piperidin-1-yl; or (ii) (a) substituted with

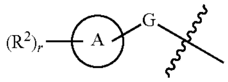

and (b) optionally further substituted with one additional methyl, chloro, fluoro, or phenyl substituent;

wherein ring A is phenyl, thienyl, or benzothiophenyl; provided that when ring A is thienyl or benzothiophenyl, G is a bond or —$CH_2$—; or when ring A is phenyl, G is selected from the group consisting of a bond, O, —$CH_2$—, $SO_2$, or C(O);

$R^2$ is trifluoromethyl, fluoro, chloro, or methanesulfonyl;

r is an integer from 0 to 3;

and enantiomers, diastereomers, solvates and pharmaceutically acceptable salts thereof.

An embodiment of the present invention is directed to a compound of Formula (I)

Formula (I)

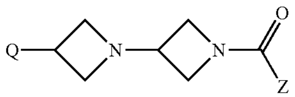

wherein:

Q is selected from

Q1

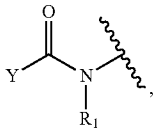

,

-continued

Q2

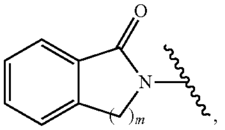

, or

Q3

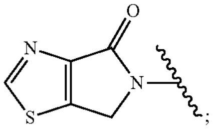

wherein

Y is phenyl or thiazolyl;

$R^1$ is hydrogen; and m is 1;

Z is $C_{6-10}$aryl or a heteroaryl selected from the group consisting of benzothiophenyl, benzoxazolyl, benzothiazolyl, indolyl, and indazolyl;

wherein Z is (i) optionally independently substituted with one to two substituents selected from the group consisting of $C_{1-4}$ alkyl, fluoro, chloro, bromo, and trifluoromethyl; or (ii) (a) substituted with

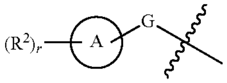

and (b) optionally further substituted with one additional methyl, chloro, fluoro, or phenyl substituent;

wherein ring A is phenyl or thienyl; provided that when ring A is thienyl, G is a bond or —$CH_2$—; or when ring A is phenyl, G is selected from the group consisting of a bond, —$CH_2$—, or $SO_2$;

$R^2$ is trifluoromethyl, fluoro, chloro, or methanesulfonyl;

r is an integer from 0 to 2;

and enantiomers, diastereomers, solvates and pharmaceutically acceptable salts thereof.

Embodiments of the present invention are directed to compounds of Formula (Ia), listed in Table 1, below.

TABLE 1

Formula (Ia)

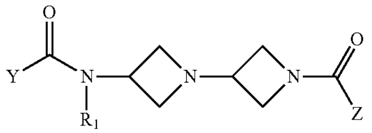

| Cpd No. | Y | $R_1$ | Z |
|---|---|---|---|
| 1 | thiazol-2-yl | H | 1-(4-trifluoromethylphenyl)-1H-indol-5-yl |
| 2 | thiazol-4-yl | H | 4-(3-trifluoromethylphenyl)phenyl |
| 3 | thiazol-2-yl | H | 1-(phenylsulfonyl)-1H-indol-5-yl |
| 4 | thiazol-2-yl | H | 2-phenyl-benzothiazol-6-yl |
| 5 | thiazol-2-yl | H | 4-(3-trifluoromethylphenyl)phenyl |

TABLE 1-continued

Formula (Ia)

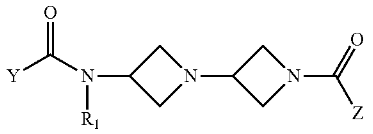

| Cpd No. | Y | $R_1$ | Z |
|---|---|---|---|
| 6 | thiazol-2-yl | H | 6-phenyl-benzothiophen-2-yl |
| 7 | thiazol-2-yl | H | 6-trifluoromethyl-benzothiophen-2-yl |
| 8 | thiazol-2-yl | H | 4-trifluoromethyl-benzothiophen-2-yl |
| 9 | thiazol-2-yl | H | 4-(5-trifluoromethyl-thien-2-yl)-phenyl |
| 10 | thiazol-2-yl | H | 4-(phenylmethyl)-phenyl |
| 11 | thiazol-4-yl | H | 1-(4-fluorophenyl)-1H-indol-5-yl |
| 12 | thiazol-2-yl | H | 4-(4-trifluoromethylphenyl)-phenyl |
| 13 | thiazol-2-yl | H | 1-phenyl-1H-indol-5-yl |
| 14 | thiazol-4-yl | H | 4-(4-trifluoromethylphenyl)-phenyl |
| 15 | thiazol-2-yl | H | 3-methyl-5-chloro-benzothiophen-2-yl |
| 16 | thiazol-2-yl | H | 4-(4-trifluoromethyl phenylmethyl)phenyl |
| 17 | thiazol-2-yl | H | 2-phenyl-benzoxazol-6-yl |
| 18 | thiazol-2-yl | H | 4-(3-methanesulfonylphenyl) phenyl |
| 19 | thiazol-2-yl | H | 5-bromo-naphth-2-yl |
| 20 | thiazol-2-yl | H | 4-(3-trifluoromethyl phenylmethyl)phenyl |
| 21 | thiazol-2-yl | H | 6-phenyl-naphth-2-yl |
| 22 | thiazol-4-yl | H | 2-phenyl-benzothiazol-6-yl |
| 23 | thiazol-2-yl | H | 6-bromo-benzothiophen-2-yl |
| 24 | phenyl | H | 5-bromo-naphth-2-yl |
| 25 | phenyl | H | 5-phenyl-naphth-2-yl |
| 26 | phenyl | H | 4-(4-trifluoromethyl phenylmethyl)phenyl |
| 27 | thiazol-2-yl | H | 1-phenyl-1H-indol-6-yl |
| 28 | thiazol-2-yl | H | 2-(3-trifluoromethylphenyl)-benzoxazol-6-yl |
| 29 | thiazol-2-yl | H | 4-phenyl-phenyl |
| 30 | thiazol-2-yl | H | 2-(4-trifluoromethylphenyl)-benzoxazol-6-yl |
| 31 | phenyl | H | 4-(phenylmethyl)phenyl |
| 32 | thiazol-2-yl | H | 4-phenoxy-phenyl |
| 33 | thiazol-2-yl | H | 2-(4-chlorophenyl)-benzoxazol-6-yl |
| 34 | phenyl | H | 6-phenyl-naphth-2-yl |
| 35 | thiazol-2-yl | H | 2-phenyl-benzoxazol-5-yl |
| 36 | phenyl | H | 3-methyl-5-chloro-benzothiophen-2-yl |
| 37 | thiazol-2-yl | methyl | 6-trifluoromethyl-benzothiophen-2-yl |
| 38 | thiazol-2-yl | H | 4-(phenylcarbonyl)-phenyl |
| 39 | phenyl | H | 4-phenyl-phenyl |
| 40 | thiazol-2-yl | H | 6-bromo-naphth-2-yl |
| 41 | phenyl | H | 2-phenyl-benzoxazol-6-yl |
| 42 | phenyl | H | 6-bromo-naphth-2-yl |
| 43 | thiazol-2-yl | H | 4-bromophenyl |
| 44 | phenyl | H | 5-trifluoromethyl-benzothiophen-2-yl |
| 45 | phenyl | H | 4-phenoxy-phenyl |
| 46 | thiazol-4-yl | H | 2-bromo-benzothiazol-6-yl |
| 47 | thiazol-2-yl | H | 5-trifluoromethyl-benzothiazol-2-yl |
| 48 | thiazol-4-yl | methyl | 6-trifluoromethyl-benzothiophen-2-yl |
| 49 | thiazol-4-yl | H | 6-trifluoromethyl-benzothiophen-2-yl |
| 50 | thiazol-2-yl | H | 3-chloro-6-trifluoromethyl-benzothiophen-2-yl |
| 51 | thiazol-4-yl | H | 3-chloro-6-trifluoromethyl-benzothiophen-2-yl |
| 52 | thiazol-2-yl | H | 1-phenyl-1H-indazol-5-yl |

TABLE 1-continued

Formula (Ia)

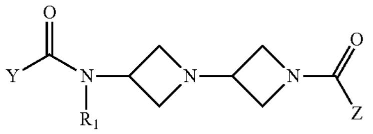

| Cpd No. | Y | $R_1$ | Z |
|---|---|---|---|
| 53 | thiazol-2-yl | H | 5-phenyl-naphth-2-yl |
| 54 | thiazol-4-yl | H | 1-(3,4-difluorophenyl)-1H-indol-5-yl |
| 55 | thiazol-2-yl | H | 1-(2,4-difluorophenyl)-1H-indol-5-yl |
| 56 | thiazol-2-yl | H | 3-methyl-6-trifluoromethyl-benzothiophen-2-yl |
| 57 | thiazol-2-yl | H | 1-(3,4-difluorophenyl)-1H-indol-5-yl |
| 58 | thiazol-2-yl | H | 2-methyl-4-(3-trifluoromethylphenyl)-phenyl |
| 59 | thiazol-2-yl | H | 2-fluoro-4-(4-trifluoromethylphenyl)-phenyl |
| 60 | thiazol-4-yl | H | 1-(2,4-difluorophenyl)-1H-indol-5-yl |
| 61 | thiazol-2-yl | H | 1-(4-fluorophenyl)-1H-indol-5-yl |
| 62 | thiazol-2-yl | H | 1-(4-fluorophenyl)-3-methyl-1H-indol-5-yl |
| 63 | thiazol-2-yl | H | 2-methyl-4-(4-trifluoromethylphenyl)phenyl |
| 64 | thiazol-2-yl | H | 2-fluoro-4-(3-trifluoromethylphenyl)phenyl |
| 65 | thiazol-2-yl | H | 3-methyl-6-bromo-benzothiophen-2-yl |
| 66 | thiazol-2-yl | H | 3-methyl-6-phenyl-benzothiophen-2-yl |
| 67 | thiazol-4-yl | H | 3-methyl-6-trifluoromethyl-benzothiophen-2-yl |

and pharmaceutically acceptable salts thereof.

Embodiments of the present invention are directed to compounds of Formula (Ib), listed in Table 2, below.

TABLE 2

Formula (Ib)

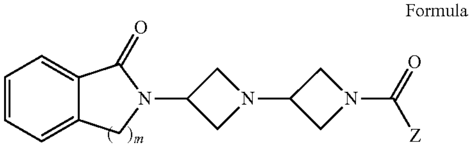

| Cpd No. | m | Z |
|---|---|---|
| 68 | 1 | 3-chloro-6-phenyl-benzothiophen-2-yl |
| 69 | 1 | 6-phenyl-naphth-2-yl |
| 70 | 1 | 1-(4-trifluoromethylphenyl)-1H-indol-5-yl |
| 71 | 1 | 1-(phenylsulfonyl)-1H-indol-5-yl |
| 72 | 1 | 6-(3-methanesulfonylphenyl)-benzothiophen-2-yl |
| 73 | 1 | 3-chloro-6-bromo-benzothiophen-2-yl |
| 74 | 1 | 3,6-diphenyl-benzothiophen-2-yl |
| 75 | 1 | 1-(3-trifluoromethylphenyl)-1H-indol-5-yl |
| 76 | 1 | 4-(5-trifluoromethyl-thien-2-yl)phenyl |
| 77 | 1 | 2-phenyl-benzoxazol-5-yl |

TABLE 2-continued

Formula (Ib)

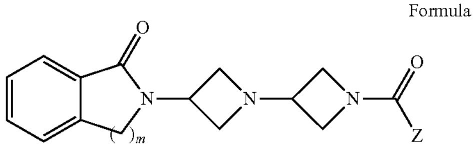

| Cpd No. | m | Z |
|---|---|---|
| 78 | 1 | 2-(3-trifluoromethylphenyl)-benzoxazol-6-yl |
| 79 | 1 | 5-phenyl-benzothiophen-2-yl |
| 80 | 1 | 4-(3-methanesulfonylphenyl) phenyl |
| 81 | 1 | 6-trifluoromethyl-benzothiophen-2-yl |
| 82 | 1 | 5-(3-methanesulfonylphenyl) benzothiophen-2-yl |
| 83 | 1 | 5-bromo-naphth-2-yl |
| 84 | 1 | 2-phenyl-benzoxazol-6-yl |
| 85 | 1 | 1-phenyl-1H-indol-5-yl |
| 86 | 1 | 4-(3-trifluoromethyl phenylmethyl)phenyl |
| 87 | 1 | 6-bromo-benzothiophen-2-yl |
| 88 | 1 | 2-(4-chlorophenyl)-benzoxazol-6-yl |
| 89 | 1 | 1-(2-trifluoromethylphenyl)-1H-indol-5-yl |
| 90 | 1 | 6-bromo-naphth-2-yl |
| 91 | 1 | 4-piperidin-1-yl-phenyl |
| 92 | 1 | 4-phenyl-phenyl |
| 93 | 1 | 5-bromo-benzothiophen-2-yl |
| 94 | 1 | 4-(phenylmethyl)phenyl |
| 95 | 1 | 4-(benzothiophen-2-yl)phenyl |
| 96 | 1 | 4-bromophenyl |
| 97 | 1 | 5-phenyl-naphth-2-yl |
| 98 | 1 | 6-phenyl-benzothiophen-2-yl |
| 99 | 1 | 3-chloro-6-trifluoromethyl-benzothiophen-2-yl |
| 100 | 1 | 3-chloro-6-fluoro-benzothiophen-2-yl |
| 101 | 1 | 3-methyl-6-trifluoromethyl-benzothiophen-2-yl |
| 102 | 1 | 1-(4-fluorophenyl)-1H-indol-5-yl |

and pharmaceutically acceptable salts thereof.

Embodiments of the present invention are directed to compounds of Formula (Ic), listed in Table 3, below.

TABLE 3

Formula (Ic)

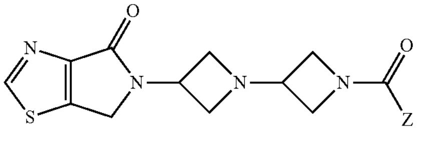

| Cpd No. | Z |
|---|---|
| 103 | 3-methyl-6-trifluoromethyl-benzothiophen-2-yl |
| 104 | 2-methyl-4-(3-trifluoromethylphenyl)phenyl |
| 105 | 2-methyl-4-(4-trifluoromethylphenyl)phenyl |
| 106 | 1-(4-trifluoromethylphenyl)-1H-indol-5-yl |

and pharmaceutically acceptable salts thereof.

For use in medicine, salts of compounds of Formula (I), including Formulas (Ia), (Ib), and (Ic), refer to non-toxic "pharmaceutically acceptable salts." Other salts may, however, be useful in the preparation of compounds of Formula (I), including Formulas (Ia), (Ib), and (Ic), or of their pharmaceutically acceptable salts thereof. Suitable pharmaceutically acceptable salts of compounds of Formula (I), including Formulas (Ia), (Ib), and (Ic), include acid addition salts which can, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of Formula (I), including Formulas (Ia), (Ib), and (Ic), carry an acidic moiety, suitable pharmaceutically acceptable salts thereof may include alkali metal salts, such as sodium or potassium salts; alkaline earth metal salts, such as, calcium or magnesium salts; and salts formed with suitable organic ligands, such as, quaternary ammonium salts. Thus, representative pharmaceutically acceptable salts include acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include acids including acetic acid, 2,2-dichloroactic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucoronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebaic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

Embodiments of the present invention include prodrugs of compounds of Formula (I), including Formulas (Ia), (Ib), and (Ic). In general, such prodrugs will be functional derivatives of the compounds that are readily convertible in vivo into the required compound. Thus, in the methods of treating or preventing embodiments of the present invention, the term "administering" encompasses the treatment or prevention of the various diseases, conditions, syndromes and disorders described with the compound specifically disclosed or with a compound that may not be specifically disclosed, but which converts to the specified compound in vivo after administration to a patient. Conventional procedures for the selection and preparation of suitable prodrug derivatives are described, for example, in "Design of Prodrugs", ed. H. Bundgaard, Elsevier, 1985.

Where the compounds according to embodiments of this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention. The skilled artisan will understand that the term compound as used herein, is meant to include solvated compounds of Formula (I), including Formulas (Ia), (Ib), and (Ic).

Where the processes for the preparation of the compounds according to certain embodiments of the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

One embodiment of the present invention is directed to a composition, including a pharmaceutical composition, comprising, consisting of, and/or consisting essentially of the (+)-enantiomer of a compound of Formula (I) wherein said composition is substantially free from the (−)-isomer of said compound. In the present context, substantially free means less than about 25%, preferably less than about 10%, more preferably less than about 5%, even more preferably less than about 2% and even more preferably less than about 1% of the (−)-isomer calculated as.

$$\%(+)-\text{enantiomer} = \frac{(\text{mass}(+)-\text{enantiomer})}{(\text{mass}(+)-\text{enantiomer})+(\text{mass}(-)-\text{enantiomer})} \times 100.$$

Another embodiment of the present invention is a composition, including a pharmaceutical composition, comprising, consisting of, and consisting essentially of the (−)-enantiomer of a compound of Formula (I) wherein said composition is substantially free from the (+)-isomer of said compound. In the present context, substantially free from means less than about 25%, preferably less than about 10%, more preferably less than about 5%, even more preferably less than about 2% and even more preferably less than about 1% of the (+)-isomer calculated as $$\%(-)-\text{enantiomer} = \frac{(\text{mass}(-)-\text{enantiomer})}{(\text{mass}(+)-\text{enantiomer})+(\text{mass}(-)-\text{enantiomer})} \times 100.$$

During any of the processes for preparation of the compounds of the various embodiments of the present invention, it may be necessary and/or desirable to protect sensitive or reactive groups on any of the molecules concerned. This may be achieved by means of conventional protecting groups, such as those described in *Protective Groups in Organic Chemistry, Second Edition*, J. F. W. McOmie, Plenum Press, 1973; T. W. Greene & P. G. M. Wuts, *Protective Groups in Organic Synthesis*, John Wiley & Sons, 1991; and T. W. Greene & P. G. M. Wuts, *Protective Groups in Organic Synthesis, Third Edition*, John Wiley & Sons, 1999. The protecting groups may be removed at a convenient subsequent stage using methods known from the art.

Even though the compounds of embodiments of the present invention (including their pharmaceutically acceptable salts and pharmaceutically acceptable solvates) can be administered alone, they will generally be administered in admixture with a pharmaceutically acceptable carrier, a pharmaceutically acceptable excipient and/or a pharmaceutically acceptable diluent selected with regard to the intended route of administration and standard pharmaceutical or veterinary practice. Thus, particular embodiments of the present invention are directed to pharmaceutical and veterinary compositions comprising compounds of Formula (I) and at least one pharmaceutically acceptable carrier, pharmaceutically acceptable excipient, and/or pharmaceutically acceptable diluent.

By way of example, in the pharmaceutical compositions of embodiments of the present invention, the compounds of Formula (I), including Formulas (Ia), (Ib), and (Ic), may be admixed with any suitable binder(s), lubricant(s), suspending agent(s), coating agent(s), solubilizing agent(s), and combinations thereof.

Solid oral dosage forms, such as tablets or capsules, containing the compounds of the present invention may be administered in at least one dosage form at a time, as appropriate. It is also possible to administer the compounds in sustained release formulations.

Additional oral forms in which the present inventive compounds may be administered include elixirs, solutions, syrups, and suspensions; each optionally containing flavoring agents and coloring agents.

Alternatively, compounds of Formula (I), including Formulas (Ia), (Ib), and (Ic), can be administered by inhalation (intratracheal or intranasal) or in the form of a suppository or pessary, or they may be applied topically in the form of a lotion, solution, cream, ointment or dusting powder. For example, they can be incorporated into a cream comprising, consisting of, and/or consisting essentially of an aqueous emulsion of polyethylene glycols or liquid paraffin. They can also be incorporated, at a concentration of between about 1% and about 10% by weight of the cream, into an ointment comprising, consisting of, and/or consisting essentially of a white wax or white soft paraffin base together with any stabilizers and preservatives as may be required. An alternative means of administration includes transdermal administration by using a skin or transdermal patch.

The pharmaceutical compositions of the present invention (as well as the compounds of the present invention alone) can also be injected parenterally, for example intracavernosally, intravenously, intramuscularly, subcutaneously, intradermally or intrathecally. In this case, the compositions will also include at least one of a suitable carrier, a suitable excipient, and a suitable diluent.

For parenteral administration, the pharmaceutical compositions of the present invention are best used in the form of a sterile aqueous solution that may contain other substances, for example, enough salts and monosaccharides to make the solution isotonic with blood.

For buccal or sublingual administration, the pharmaceutical compositions of the present invention may be administered in the form of tablets or lozenges, which can be formulated in a conventional manner.

By way of further example, pharmaceutical compositions containing at least one of the compounds of Formula (I), including Formulas (Ia), (Ib), and (Ic), as the active ingredient can be prepared by mixing the compound(s) with a pharmaceutically acceptable carrier, a pharmaceutically acceptable diluent, and/or a pharmaceutically acceptable excipient according to conventional pharmaceutical compounding techniques. The carrier, excipient, and diluent may take a wide variety of forms depending upon the desired route of administration (e.g., oral, parenteral, etc.). Thus for liquid oral preparations, such as suspensions, syrups, elixirs and solutions, suitable carriers, excipients and diluents include water, glycols, oils, alcohols, flavoring agents, preservatives, stabilizers, coloring agents and the like; for solid oral preparations, such as powders, capsules and tablets, suitable carriers, excipients and diluents include starches, sugars, diluents, granulating agents, lubricants, binders, disintegrating agents and the like. Solid oral preparations also may be optionally coated with substances, such as, sugars, or be enterically-coated so as to modulate the major site of absorption and disintegration. For parenteral administration, the carrier, excipient and diluent will usually include sterile water, and other ingredients may be added to increase solubility and preservation of the composition. Injectable suspensions or solutions may also be prepared utilizing aqueous carriers along with appropriate additives, such as solubilizers and preservatives.

A therapeutically effective amount of a compound of Formula (I), including Formulas (Ia), (Ib), and (Ic), or a pharmaceutical composition thereof includes a dose range from about 0.1 mg to about 3000 mg, or any particular amount or range therein, in particular from about 1 mg to about 1000 mg, or any particular amount or range therein; or, more particularly, from about 10 mg to about 500 mg, or any particular amount or range therein, of active ingredient in a regimen of about 1 to about 4 times per day for an average (70 kg) human; although, it is apparent to one skilled in the art that the therapeutically effective amount for a compound of Formula (I), including Formulas (Ia), (Ib), and (Ic), will vary as will the diseases, syndromes, conditions, and disorders being treated.

For oral administration, a pharmaceutical composition is preferably provided in the form of tablets containing about 0.01, about 10, about 50, about 100, about 150, about 200, about 250, and about 500 milligrams of a compound of Formula (I), including Formulas (Ia), (Ib), and (Ic).

Advantageously, a compound of Formula (I), including Formulas (Ia), (Ib), and (Ic), may be administered in a single daily dose, or the total daily dosage may be administered in divided doses of two, three and four times daily.

Optimal dosages of a compound of Formula (I), including Formulas (Ia), (Ib), and (Ic), to be administered may be readily determined and will vary with the particular compound used, the mode of administration, the strength of the preparation and the advancement of the disease, syndrome, condition or disorder. In addition, factors associated with the particular subject being treated, including subject gender, age, weight, diet and time of administration, will result in the need to adjust the dose to achieve an appropriate therapeutic level and desired therapeutic effect. The above dosages are thus exemplary of the average case. There can be, of course, individual instances wherein higher or lower dosage ranges are merited, and such are within the scope of this invention.

Compounds of Formula (I), including Formulas (Ia), (Ib), and (Ic), may be administered in any of the foregoing compositions and dosage regimens or by means of those compositions and dosage regimens established in the art whenever use of a compound of Formula (I), including Formulas (Ia), (Ib), and (Ic), is required for a subject in need thereof.

As MGL inhibitors, the compounds of Formula (I), including Formulas (Ia), (Ib), and (Ic), are useful in methods for treating and preventing a disease, a syndrome, a condition or a disorder in a subject, including an animal, a mammal and a human in which the disease, the syndrome, the condition or the disorder is affected by the modulation of the MGL enzyme. Such methods comprise, consist of and/or consist essentially of administering to a subject, including an animal, a mammal, and a human in need of such treatment or prevention a therapeutically effective amount of a compound, salt or solvate of Formula (I), including Formulas (Ia), (Ib), and (Ic). In particular, the compounds of Formula (I), including Formulas (Ia), (Ib), and (Ic), are useful for preventing or treating pain, or diseases, syndromes, conditions, or disorders causing such pain, or for treating inflammation or CNS disorders.

Examples of inflammatory pain include pain due to a disease, condition, syndrome, disorder, or a pain state, including inflammatory bowel disease, visceral pain, migraine, post operative pain, osteoarthritis, rheumatoid arthritis, back pain, lower back pain, joint pain, abdominal pain, chest pain, labor pain, musculoskeletal diseases, skin diseases, toothache, pyresis, burn, sunburn, snake bite, venomous snake bite, spider bite, insect sting, neurogenic bladder, interstitial cystitis, urinary tract infection, rhinitis, contact dermatitis/hypersensitivity, itch, eczema, pharyngitis, mucositis, enteritis, irritable bowel syndrome, cholecystitis, pancreatitis, postmastectomy pain syndrome, menstrual pain, endometriosis pain, pain due to physical trauma, headache, sinus headache, tension headache, or arachnoiditis.

Examples of CNS disorders include anxieties, such as social anxiety, post-traumatic stress disorder, phobias, social phobia, special phobias, panic disorder, obsessive-compulsive disorder, acute stress disorder, separation anxiety disorder, and generalized anxiety disorder, as well as depression, such as major depression, bipolar disorder, seasonal affective disorder, post natal depression, manic depression, and bipolar depression.

General Synthetic Methods

Representative compounds of the present invention can be synthesized in accordance with the general synthetic methods described below and illustrated in the schemes and examples that follow. Since the schemes are an illustration, the invention should not be construed as being limited by the chemical reactions and conditions described in the schemes. The various starting materials used in the schemes and examples are commercially available or may be prepared by methods well within the skill of persons versed in the art. The variables are as defined herein.

Abbreviations used in the instant specification, particularly the schemes and examples, are as follows:

AcCl acetyl chloride
AcOH glacial acetic acid
aq. aqueous
Bn or Bzl benzyl
Boc tert-butyloxycarbonyl
conc. concentrated
DCC N,N'-dicyclohexyl-carbodiimide
DCE 1,2-dichloroethane
DCM dichloromethane
DIPEA diisopropyl-ethyl amine
DMAP 4-dimethylaminopyridine
DMF N,N-dimethylformamide
DMSO dimethylsulfoxide DPPA diphenylphosphoryl azide
EDC N-(3-dimethylaminopropyl)-N'-ethylcarbodiimide hydrochloride
ESI electrospray ionization
EtOAc ethyl acetate
EtOH ethanol
h hour(s)
HATU O-(1H-7-azabenzotriazol-1-yl)-1,1,3,3-tetramethyluronium hexafluorophosphate
HBTU O-(1H-benzotriazol-1-yl)-1,1,3,3-tetramethyluronium hexafluorophosphate
HEK human embryonic kidney
HEPES (4-(2-hydroxyethyl)-1-piperazineethane sulfonic acid
HPLC high performance liquid chromatography
HOBt N-hydroxybenzotriazole
mCPBA meta-chloroperoxybenzoic acid
MeCN acetonitrile
MeOH methanol
MeOTf methyl triflate
MHz megahertz
min minutes
MS mass spectrometry
NMR nuclear magnetic resonance
PIPES piperazine-N,N'-bis(2-ethanesulfonic acid)
PyBrOP bromo-tris-pyrrolidinophosphonium hexafluorophosphate
RP reverse-phase
$R_t$ retention time
TEA or $Et_3N$ triethylamine
TFA trifluoroacetic acid
THF tetrahydrofuran
TLC thin layer chromatography
TMS tetramethylsilane Scheme A illustrates a route for the synthesis of compounds of Formula (Ia) wherein Y and Z are as defined herein and $R_1$ is hydrogen.

Scheme A

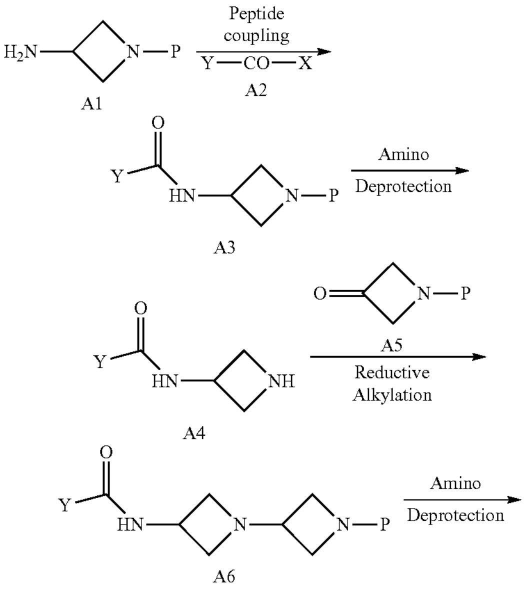

A1 A3 A4 A6

-continued

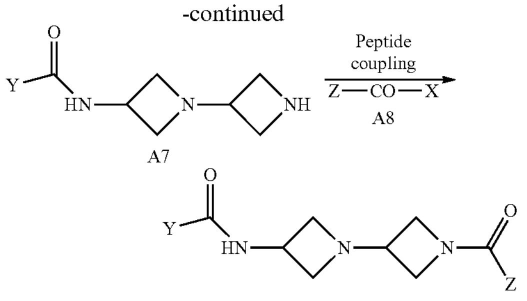

A7

Formula (Ia)

A compound of formula A1 (wherein P is a conventional amino protecting group such as Boc, Fmoc, Cbz, and the like) is either commercially available or may be prepared by known methods described in the scientific literature. A compound of formula A1 may be treated with a carboxylic acid of formula A2 (wherein X is hydroxy) in the presence of an appropriate coupling agent such as HATU, DCC, EDC, HBTU, PyBrOP, and the like; and optionally in the presence of a base such as DIPEA, to afford a compound of formula A3. Similarly, an acid chloride of formula A2 (wherein X is chloro) may be used to effect the acylation of a compound of formula A1. In such case a non-nucleophilic base such as pyridine may be added to afford a compound of Formula A3. Conventional amino deprotection of a compound of formula A3 affords an amine of formula A4 which may undergo a reductive alkylation with a compound of formula A5 (wherein P is a conventional amino protecting group such as Boc, Fmoc, Cbz, and the like) in the presence of a hydride source such as sodium triacetoxyborohydride to afford a compound of formula A6. Removal of amino protecting group P by conventional methods affords an amine of formula A7, which may be treated with a Z-substituted carboxylic acid of formula A8 (wherein X is hydroxy) in the presence of an appropriate coupling agent such as HATU, DCC, EDC, HBTU, PyBrOP, and the like; and optionally in the presence of a base such as DIPEA, to afford a compound of Formula (Ia). Similarly, an acid chloride of formula A8 (wherein X is chloro) may be used to effect the acylation of a compound of formula A7. In such case a non-nucleophilic base such as pyridine may be added to afford a compound of Formula (Ia).

Scheme B illustrates a route for the synthesis of compounds of Formula (Ia) wherein Y and Z are as defined herein and $R_1$ is $C_{1-4}$alkyl.

Scheme B

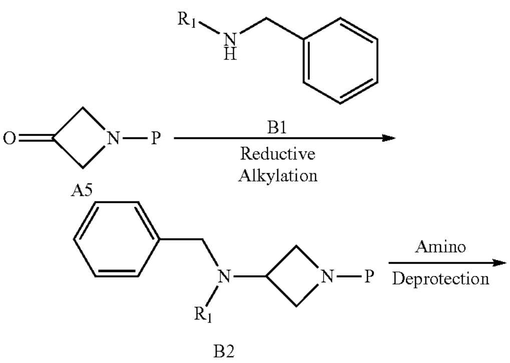

A5 B2

-continued

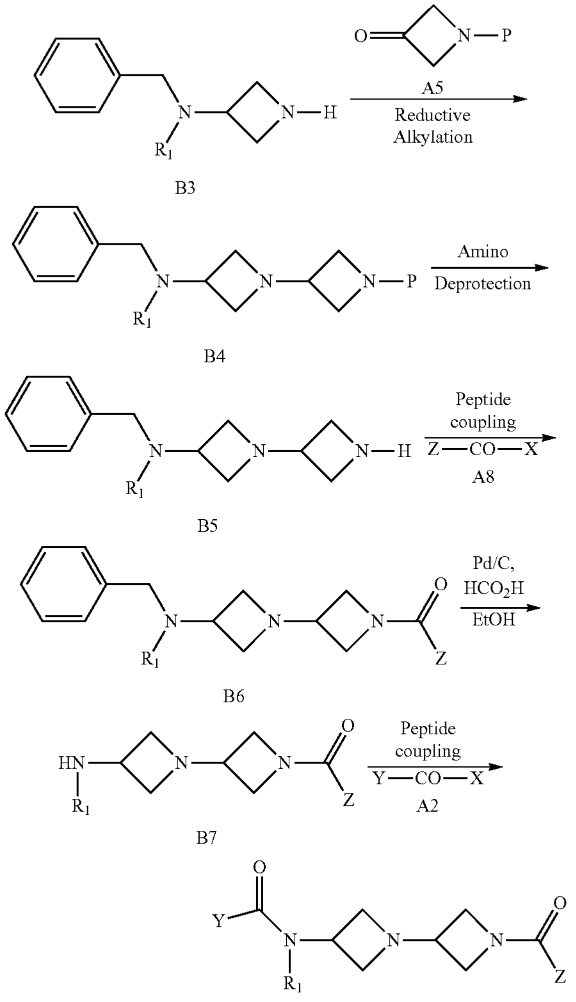

B3

B4

B5

B6

B7

Formula (Ia)

The compound of formula A5 may undergo a reductive alkylation with a commercially available $R_1$-substituted benzyl amine (B1) in the presence of a hydride source, such as, sodium triacetoxyborohydride, and in an aprotic solvent, such as, dichloromethane, dichloroethane, and the like, to afford a compound of formula B2. Conventional removal of amino protecting group P followed by a reductive alkylation with a compound of formula A5, as previously described in Scheme A, affords a compound of formula B4. Removal of amino protecting group P affords the secondary amine of formula B5, which may then participate in a peptide coupling reaction with a compound of formula A8 as described in Scheme A to afford a compound of formula B6. The benzyl protecting group may be removed with a palladium catalyst, in the presence of formic acid and in an alcoholic solvent, such as, methanol or ethanol, to afford an amine of formula B7. Coupling with a compound of formula A2 using the conditions previously described in Scheme A affords the final compound of Formula (Ia).

Scheme C illustrates a route for the synthesis of compounds of Formula (Ib) wherein m and Z are as defined herein.

Scheme C

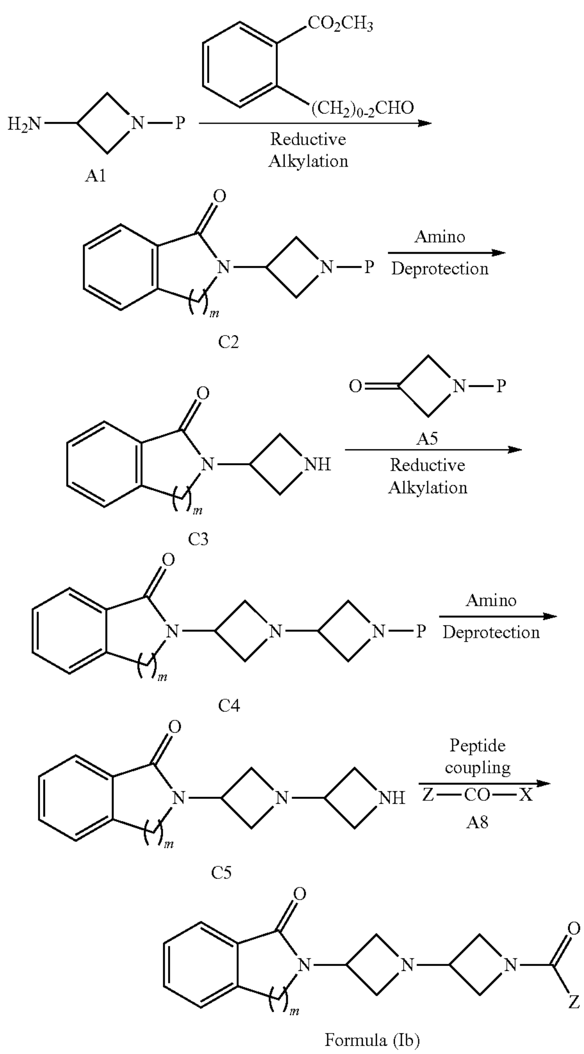

A1

C2

C3

C4

C5

Formula (Ib)

The compound of formula A1 may be treated with an aldehyde of formula C1 in the presence of a hydride source, such as, sodium triacetoxyborohydride, and in an aprotic solvent, such as, dichloromethane, dichloroethane, and the like, to afford a compound of formula C2. Removal of amino protecting group P using convention methods affords an amine of formula C3. Reductive alkylation with a compound of formula A5, as described in previous schemes, affords a compound of formula C4. Amino deprotection followed by coupling with a compound of formula A8 under peptide coupling conditions affords a desired compound of Formula (Ib).

Scheme D illustrates a route for the synthesis of compounds of Formula (Ic) wherein Z is as defined herein.

Scheme D

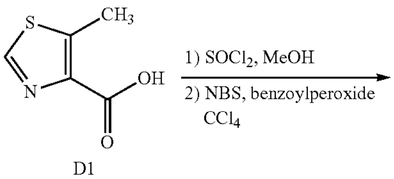

D1

-continued

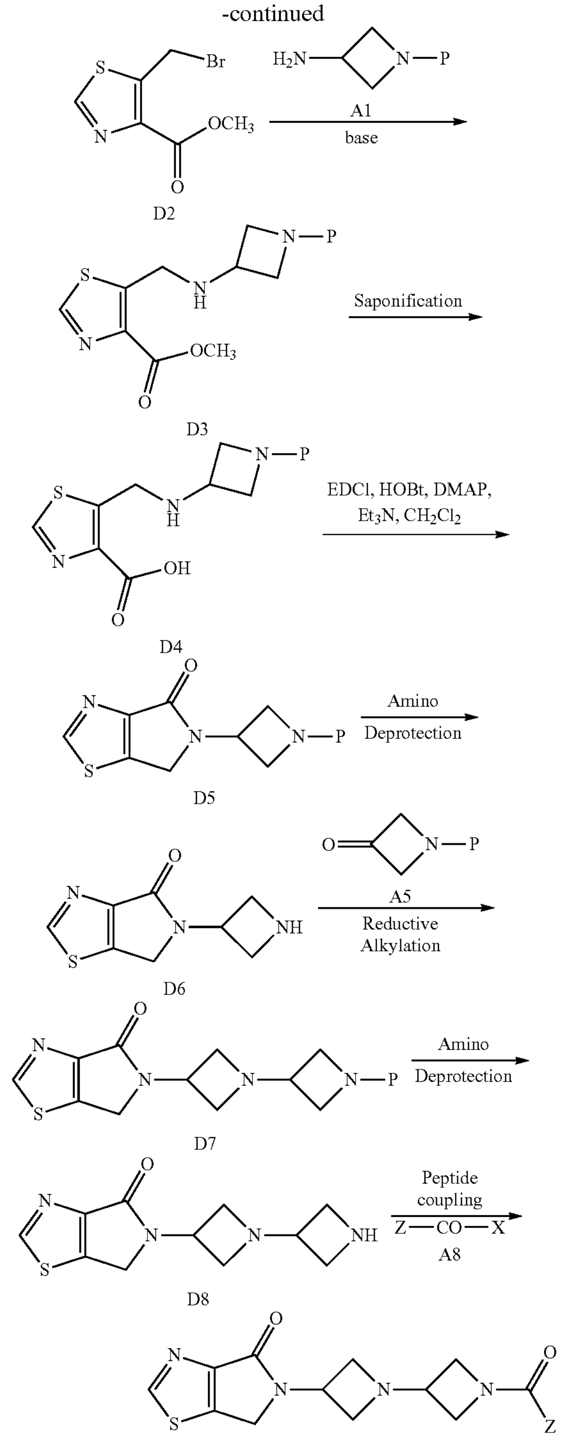

A1, D2, D3, D4, D5, A5, D6, D7, D8, A8

Formula (Ic)

A compound of formula D1 is either commercially available or may be prepared by known methods described in the scientific literature. The compound of formula D1 may be converted to a compound of formula D2 by the action of thionyl chloride and methanol to give the methyl ester, followed by N-bromosuccinimide in the presence of benzoylperoxide in carbon tetrachloride to give the final methyl bromide. Nucleophilic displacement of the bromide of formula D2 with an amine of formula A1, in the presence of an inorganic base, such as, potassium carbonate, affords a compound of formula D3. Conventional saponification using reagents, such as, sodium hydroxide in ethanol affords the corresponding carboxylic acid of formula D4. Treatment of a compound of formula D4 with EDCI, in the presence of a coupling additive, such as, HOBt, and in the presence of a hindered organic base, such as, DMAP, affords the cyclized product of formula D5. Conventional amino deprotection of a compound of formula D5 followed by reductive alkylation with a compound of formula A5 affords a compound of formula D7. Removal of the amino protecting group P followed by coupling with the compound of formula A8 as previously described affords a compound of Formula (Ic) of the present invention.

Example 1

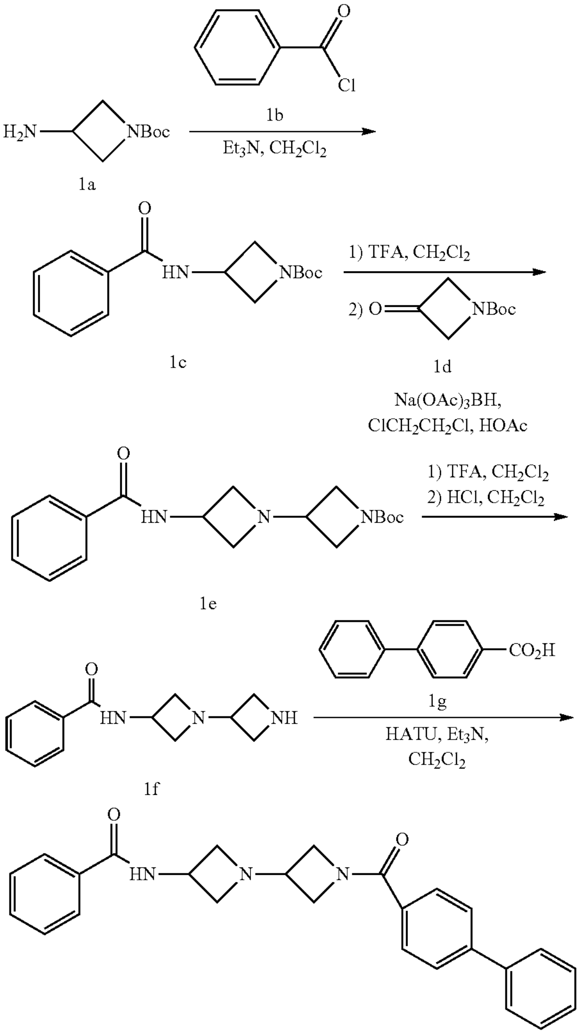

1a, 1b, 1c, 1d, 1e, 1f, 1g

Cpd 39

A. tert-Butyl 3-benzamidoazetidine-1-carboxylate, 1c

To a solution of 1-Boc-3-aminoazetidine 1a (1.2 g, 6.98 mmol) and $Et_3N$ (2.4 mL, 17.3 mmol) in $CH_2Cl_2$ (70 mL) at 0° C. was added benzoyl chloride 1b (0.89 mL, 7.68 mmol).

The reaction was kept at 0° C. for 3 h, quenched with aq. $NaHCO_3$, and the resulting mixture was extracted with $CH_2Cl_2$. The organic solution was dried over $Na_2SO_4$ and concentrated. Purification by flash column chromatography (silica gel, 40% EtOAc/heptane) gave compound 1c (1.9 g).

B. tert-Butyl 3-benzamido-[1,3'-biazetidine]-1'-carboxylate, 1e

To a solution of 1c (1.45 g, 5.25 mmol) in $CH_2Cl_2$ (20 mL) at room temperature was added $CF_3CO_2H$ (5 mL). The reaction was stirred at room temperature for 1.5 h. The reaction was concentrated and the resulting residue was dissolved in a mixed solution of 1,2-dichloroethane (10 mL) and acetic acid (0.5 mL). To the resulting solution at room temperature was added 1-Boc-azetidin-3-one 1d (0.99 g, 5.79 mmol), followed by $Na(OAc)_3BH$ (1.23 g, 5.80 mmol). The reaction mixture was stirred at room temperature for 20 h. Additional 1-Boc-azetidin-3-one 1d (0.50 g, 2.92 mmol) and $Na(OAc)_3BH$ (0.62 g, 2.92 mmol) was added. The reaction was stirred for another 6 h before it was quenched by the addition of aq. $NaHCO_3$. The resulting mixture was extracted with $CH_2Cl_2$. The organic solution was dried over $Na_2SO_4$ and concentrated. Purification by flash column chromatography (silica gel, 4% MeOH/$CH_2Cl_2$) gave compound 1e (0.93 g).

C. N-[1'-(Biphenyl-4-ylcarbonyl)-1,3'-biazetidin-3-yl]benzamide, Cpd 39

A solution of compound 1e (65 mg, 0.20 mmol) in $CH_2Cl_2$ (2 mL) and $CF_3CO_2H$ (0.5 mL) was stirred at room temperature for 2 h. The reaction mixture was concentrated and the resulting residue was dissolved in $CH_2Cl_2$ (3 mL). To this solution was added 1N HCl in ether (1 mL, 1 mmol), and the resulting mixture was concentrated to give compound 1f. To a mixture of compound 1f (0.20 mmol), 4-phenylbenzoic acid (59 mg, 0.30 mmol), and $Et_3N$ (0.17 mL, 1.22 mmol) in $CH_2Cl_2$ (3 mL) was added HATU (114 mg, 0.30 mmol). The reaction was stirred at room temperature for 20 h. The mixture was diluted with $CH_2Cl_2$, washed with aq. $NaHCO_3$, dried over $Na_2SO_4$ and concentrated. Purification by flash column chromatography (silica gel, 4% MeOH/$CH_2Cl_2$) gave compound 39 (40 mg). MS 412 ($M+H^+$).

Following the procedure described above for Example 1 and substituting the appropriate reagents, starting materials and purification methods known to those skilled in the art, the following compounds of the present invention were prepared:

| Cpd | Name and data |
|---|---|
| 1 | N-[1'-({1-[4-(Trifluoromethyl)phenyl]-1H-indol-5-yl}carbonyl)-1,3'-biazetidin-3-yl]-1,3-thiazole-2-carboxamide. $^1H$ NMR (CHLOROFORM-d, 400 MHz): δ = 8.0 (s, 1 H), 7.50-7.90 (m, 8 H), 7.40 (s, 1H), 6.80 (s, 1H), 4.75(m, 1 H), 4.00-4.40 (m, 4 H), 3.75 (m, 2 H), 3.55 (m, 1 H), 3.20 ppm (m, 2 H). MS 526 ($M + H^+$). |
| 3 | N-(1'-{[1-(Phenylsulfonyl)-1H-indol-5-yl]carbonyl}-1,3'-biazetidin-3-yl)-1,3-thiazole-2-carboxamide. MS 522 ($M + H^+$). |
| 4 | N-{1'-[(2-Phenyl-1,3-benzothiazol-6-yl)carbonyl]-1,3'-biazetidin-3-yl}-1,3-thiazole-2-carboxamide MS 476 ($M + H^+$). |
| 9 | N-[1'-({4-[5-(Trifluoromethyl)thiophen-2-yl]phenyl}carbonyl)-1,3'-biazetidin-3-yl]-1,3-thiazole-2-carboxamide. MS 493 ($M + H^+$). |
| 10 | N-{1'-[(4-Benzylphenyl)carbonyl]-1,3'-biazetidin-3-yl}-1,3-thiazole-2-carboxamide. MS 433 ($M + H^+$). |

-continued

| Cpd | Name and data |
|---|---|
| 11 | N-(1'-{[1-(4-Fluorophenyl)-1H-indol-5-yl]carbonyl}-1,3'-biazetidin-3-yl)-1,3-thiazole-4-carboxamide. MS 476 ($M + H^+$). |
| 13 | N-{1'-[(1-Phenyl-1H-indol-5-yl)carbonyl]-1,3'-biazetidin-3-yl}-1,3-thiazole-2-carboxamide. MS 458 ($M + H^+$). |
| 15 | N-{1'-[(5-Chloro-3-methyl-1-benzothiophen-2-yl)carbonyl]-1,3'-biazetidin-3-yl}-1,3-thiazole-2-carboxamide. MS 447 ($M + H^+$). |
| 16 | N-[1'-({4-[4-(Trifluoromethyl)benzyl]phenyl}carbonyl)-1,3'-biazetidin-3-yl]-1,3-thiazole-2-carboxamide. MS 501 ($M + H^+$). |
| 17 | N-{1'-[(2-Phenyl-1,3-benzoxazol-6-yl)carbonyl]-1,3'-biazetidin-3-yl}-1,3-thiazole-2-carboxamide $^1H$ NMR (CHLOROFORM-d, 400 MHz): δ = 8.27 (m, 2 H), 7.52-7.92 (m, 8 H), 4.78(m, 1 H), 4.20-4.40 (m, 2 H), 4.15 (m, 1 H), 4.04 (m, 1 H), 3.75 (m, 2 H), 3.55 (m, 1 H), 2.23 ppm (m, 2 H). MS 460 ($M + H^+$). |
| 19 | N-{1'-[(5-Bromonaphthalen-2-yl)carbonyl]-1,3'-biazetidin-3-yl}-1,3-thiazole-2-carboxamide. MS 472 ($M + H^+$). |
| 20 | N-[1'-({4-[3-(Trifluoromethyl)benzyl]phenyl}carbonyl)-1,3'-biazetidin-3-yl]-1,3-thiazole-2-carboxamide. MS 501 ($M + H^+$). |
| 22 | N-{1'-[(2-Phenyl-1,3-benzothiazol-6-yl)carbonyl]-1,3'-biazetidin-3-yl}-1,3-thiazole-4-carboxamide. MS 476 ($M + H^+$). |
| 23 | N-{1'-[(6-Bromo-1-benzothiophen-2-yl)carbonyl]-1,3'-biazetidin-3-yl}-1,3-thiazole-2-carboxamide. MS 478 ($M + H^+$). |
| 24 | N-{1'-[(5-Bromonaphthalen-2-yl)carbonyl]-1,3'-biazetidin-3-yl}benzamide. MS 465 ($M + H^+$). |
| 26 | N-[1'-({4-[4-(Trifluoromethyl)benzyl]phenyl}carbonyl)-1,3'-biazetidin-3-yl]benzamide. MS 494 ($M + H^+$). |
| 27 | N-{1'-[(1-Phenyl-1H-indol-6-yl)carbonyl]-1,3'-biazetidin-3-yl}-1,3-thiazole-2-carboxamide. MS 458 ($M + H^+$). |
| 28 | N-[1'-({2-[3-(Trifluoromethyl)phenyl]-1,3-benzoxazol-6-yl}carbonyl)-1,3'-biazetidin-3-yl]-1,3-thiazole-2-carboxamide. MS 528 ($M + H^+$). |
| 29 | N-[1'-(Biphenyl-4-ylcarbonyl)-1,3'-biazetidin-3-yl]-1,3-thiazole-2-carboxamide. MS 419 ($M + H^+$). |
| 30 | N-[1'-({2-[4-(Trifluoromethyl)phenyl]-1,3-benzoxazol-6-yl}carbonyl)-1,3'-biazetidin-3-yl]-1,3-thiazole-2-carboxamide. MS 528 ($M + H^+$). |
| 31 | N-{1'-[(4-Benzylphenyl)carbonyl]-1,3'-biazetidin-3-yl}benzamide. MS 426 ($M + H^+$). |
| 32 | N-{1'-[(4-Phenoxyphenyl)carbonyl]-1,3'-biazetidin-3-yl}-1,3-thiazole-2-carboxamide. MS 435 ($M + H^+$). |
| 33 | N-(1'-{[2-(4-Chlorophenyl)-1,3-benzoxazol-6-yl]carbonyl}-1,3'-biazetidin-3-yl)-1,3-thiazole-2-carboxamide. MS 494 ($M + H^+$). |
| 35 | N-{1'-[(2-Phenyl-1,3-benzoxazol-5-yl)carbonyl]-1,3'-biazetidin-3-yl}-1,3-thiazole-2-carboxamide. MS 460 ($M + H^+$). |
| 36 | N-{1'-[(5-Chloro-3-methyl-1-benzothiophen-2-yl)carbonyl]-1,3'-biazetidin-3-yl}benzamide MS 440 ($M + H^+$). |
| 38 | N-(1'-{[4-(Phenylcarbonyl)phenyl]carbonyl}-1,3'-biazetidin-3-yl)-1,3-thiazole-2-carboxamide. MS 447 ($M + H^+$). |
| 40 | N-{1'-[(6-Bromonaphthalen-2-yl)carbonyl]-1,3'-biazetidin-3-yl}-1,3-thiazole-2-carboxamide. MS 472 ($M + H^+$). |
| 41 | N-{1'-[(2-Phenyl-1,3-benzoxazol-6-yl)carbonyl]-1,3'-biazetidin-3-yl}benzamide. MS 453 ($M + H^+$). |
| 42 | N-{1'-[(6-Bromonaphthalen-2-yl)carbonyl]-1,3'-biazetidin-3-yl}benzamide. MS 465 ($M + H^+$). |
| 43 | N-{1'-[(4-Bromophenyl)carbonyl]-1,3'-biazetidin-3-yl}-1,3-thiazole-2-carboxamide. MS 421 ($M + H^+$). |
| 44 | N-(1'-{[5-(Trifluoromethyl)-1-benzothiophen-2-yl[carbonyl}-1,3'-biazetidin-3-yl)benzamide. MS 460 ($M + H^+$). |
| 45 | N-{1'-[(4-Phenoxyphenyl)carbonyl]-1,3'-biazetidin-3-yl}benzamide. MS 428 ($M + H^+$). |

-continued

| Cpd | Name and data |
|---|---|
| 46 | N-{1'-[(2-Bromo-1,3-benzothiazol-6-yl)carbonyl]-1,3'-biazetidin-3-yl}-1,3-thiazole-4-carboxamide. MS 478 ($M + H^+$). |
| 52 | N-{1'-[(1-Phenyl-1H-indazol-5-yl)carbonyl]-1,3'-biazetidin-3-yl}-1,3-thiazole-2-carboxamide. MS 459 ($M + H^+$). |
| 54 | N-(1'-{[1-(3,4-Difluorophenyl)-1H-indol-5-yl[carbonyl}-1,3'-biazetidin-3-yl)-1,3-thiazole-4-carboxamide. MS 494 ($M + H^+$). |
| 55 | N-(1'-{[1-(2,4-Difluorophenyl)-1H-indol-5-yl[carbonyl}-1,3'-biazetidin-3-yl)-1,3-thiazole-2-carboxamide. MS 494 ($M + H^+$). |
| 57 | N-(1'-{[1-(3,4-Difluorophenyl)-1H-indol-5-yl[carbonyl}-1,3'-biazetidin-3-yl)-1,3-thiazole-2-carboxamide. MS 494 ($M + H^+$). |
| 60 | N-(1'-{[1-(2,4-Difluorophenyl)-1H-indol-5-yl[carbonyl}-1,3'-biazetidin-3-yl)-1,3-thiazole-4-carboxamide. MS 494 ($M + H^+$). |
| 61 | N-(1'-{[1-(4-Fluorophenyl)-1H-indol-5-yl]carbonyl}-1,3'-biazetidin-3-yl)-1,3-thiazole-2-carboxamide. MS 476 ($M + H^+$). |
| 62 | N-(1'-{[1-(4-Fluorophenyl)-3-methyl-1H-indol-5-yl[carbonyl}-1,3'-biazetidin-3-yl)-1,3-thiazole-2-carboxamide. MS 490 ($M + H^+$). |

Example 2

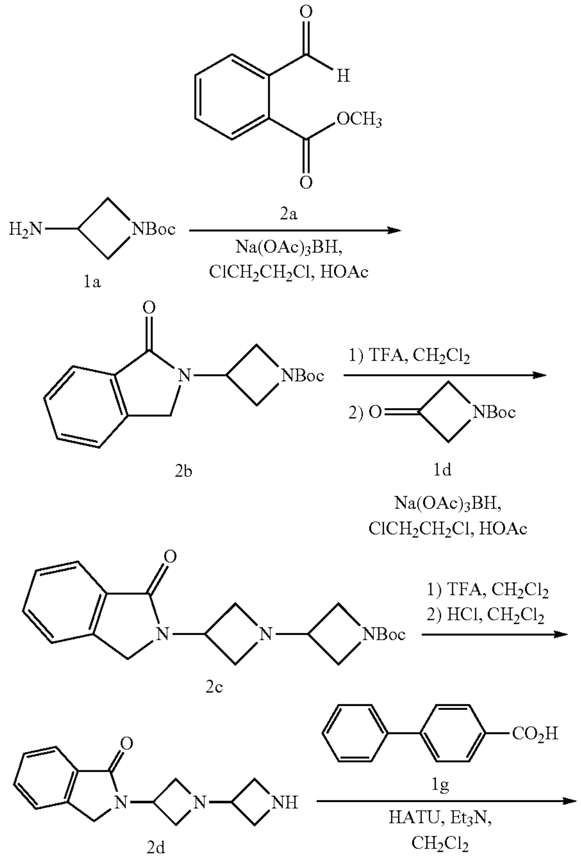

-continued

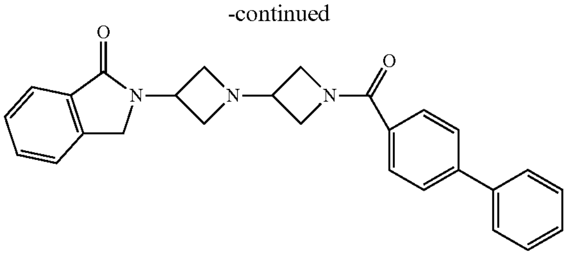

Cpd 92

A. tert-butyl 3-(1-oxoisoindolin-2-yl)azetidine-1-carboxylate, 2b

To a solution of 1-Boc-3-aminoazetidine 1a (1.0 g, 5.8 mmol) and methyl 2-formylbenzoate 2a (0.95 g, 5.8 mmol) in 1,2-dichloroethane (30 mL) and acetic acid (1.5 mL) was added $Na(OAc)_3BH$ (1.29 g, 6.08 mmol) at room temperature. The reaction was stirred for 5.5 h. It was quenched with aq. $NaHCO_3$, and the resulting mixture was extracted with $CH_2Cl_2$. The organic solution was dried over $Na_2SO_4$ and concentrated. Purification by flash column chromatography (silica gel, 40% EtOAc/heptane) gave compound 2b (1.46 g).

B. 2-[1'-(Biphenyl-4-ylcarbonyl)-1,3'-biazetidin-3-yl]-2,3-dihydro-1H-isoindol-1-one, Cpd 92

Compound 92 was prepared from intermediate 2b following the procedures described in Steps B and C of Example 1. MS 424 ($M+H^+$).

Following the procedure described above for Example 2 and substituting the appropriate reagents, starting materials and purification methods known to those skilled in the art, the following compounds of the present invention were prepared:

| Cpd | Name and data |
|---|---|
| 70 | 2-[1'-({1-[4-(Trifluoromethyl)phenyl]-1H-indol-5-yl}carbonyl)-1,3'-biazetidin-3-yl]-2,3-dihydro-1H-isoindol-1-one. $^1H$ NMR (CHLOROFORM-d, 400 MHz): δ = 8.00 (s, 1 H), 7.80 (m, 3H), 7.40-7.70 (m, 8 H), 6.80 (m, 1H), 5.05 (m, 1 H), 4.60 (s, 2H), 4.00-4.40 (m, 4 H), 3.70 (m, 2 H), 3.60 (m, 1 H), 3.40 ppm (m, 2 H). MS 531 ($M + H^+$). |
| 71 | 2-(1'-{[1-(Phenylsulfonyl)-1H-indol-5-yl]carbonyl}-1,3'-biazetidin-3-yl)-2,3-dihydro-1H-isoindol-1-one. MS 527 ($M + H^+$). |
| 75 | 2-{1'-[(6-Bromo-3-chloro-1-benzothiophen-2-yl)carbonyl]-1,3'-biazetidin-3-yl}-2,3-dihydro-1H-isoindol-1-one. MS 531 ($M + H^+$). |
| 76 | 2-[1'-({4-[5-(Trifluoromethyl)thiophen-2-yl]phenyl}carbonyl)-1,3'-biazetidin-3-yl]-2,3-dihydro-1H-isoindol-1-one. $^1H$ NMR (CHLOROFORM-d, 400 MHz): δ = 7.30-7.80 (m, 10 H), 5.05(m, 1 H), 4.60 (s, 2 H), 4.00-4.40 (m, 4 H), 3.70 (m, 2 H), 3.60 (m, 1 H), 3.45 ppm (m, 2 H). MS 498 ($M + H^+$). |
| 77 | 2-{1'-[(2-Phenyl-1,3-benzoxazol-5-yl)carbonyl]-1,3'-biazetidin-3-yl}-2,3-dihydro-1H-isoindol-1-one. $^1H$ NMR (CHLOROFORM-d, 400 MHz): δ = 8.26 (dd, J = 7.4, 1.6 Hz, 2 H), 8.02 (d, J = 1.2 Hz, 2 H), 7.84 (d, J = 7.4 Hz, 2 H), 7.77 (m, 1 H), 7.46-7.64 (m, 7 H), 5.09 (m, 1 H), 4.62 (s, 2 H), 4.00-4.40 (m, 4 H), 3.69 (m, 2 H), 3.61 (m, 1 H), 3.49 ppm (br. s., 2 H). MS 465 ($M + H^+$). |
| 78 | 2-[1'-({2-[3-(Trifluoromethyl)phenyl]-1,3-benzoxazol-6-yl}carbonyl)-1,3'-biazetidin-3-yl]-2,3-dihydro-1H-isoindol-1-one. MS 533 ($M + H^+$). |

-continued

| Cpd | Name and data |
|---|---|
| 83 | 2-{1'-[(5-Bromonaphthalen-2-yl)carbonyl]-1,3'-biazetidin-3-yl}-2,3-dihydro-1H-isoindol-1-one. MS 477 (M + H$^+$). |
| 84 | 2-{1'-[(2-Phenyl-1,3-benzoxazol-6-yl)carbonyl]-1,3'-biazetidin-3-yl}-2,3-dihydro-1H-isoindol-1-one. MS 465 (M + H$^+$). |
| 85 | 2-{1'-[(1-Phenyl-1H-indol-5-yl)carbonyl]-1,3'-biazetidin-3-yl}-2,3-dihydro-1H-isoindol-1-one. MS 463 (M + H$^+$). |
| 86 | 2-[1'-({4-[3-(Trifluoromethyl)benzyl]phenyl}carbonyl)-1,3'-biazetidin-3-yl]-2,3-dihydro-1H-isoindol-1-one. MS 506 (M + H$^+$). |
| 88 | 2-(1'-{[2-(4-Chlorophenyl)-1,3-benzoxazol-6-yl]carbonyl}-1,3'-biazetidin-3-yl)-2,3-dihydro-1H-isoindol-1-one. MS 499 (M + H$^+$). |
| 89 | 2-[1'-({1-[2-(Trifluoromethyl)phenyl]-1H-indol-5-yl}carbonyl)-1,3'-biazetidin-3-yl]-2,3-dihydro-1H-isoindol-1-one. MS 531 (M + H$^+$). |
| 90 | 2-{1'-[(6-Bromonaphthalen-2-yl)carbonyl]-1,3'-biazetidin-3-yl}-2,3-dihydro-1H-isoindol-1-one. MS 477 (M + H$^+$). |
| 91 | 2-{1'-[(4-Piperidin-1-ylphenyl)carbonyl]-1,3'-biazetidin-3-yl}-2,3-dihydro-1H-isoindol-1-one. MS 431 (M + H$^+$). |
| 94 | 2-{1'-[(4-Benzylphenyl)carbonyl]-1,3'-biazetidin-3-yl}-2,3-dihydro-1H-isoindol-1-one. MS 438 (M + H$^+$). |
| 96 | 2-{1'-[(4-Bromophenyl)carbonyl]-1,3'-biazetidin-3-yl}-2,3-dihydro-1H-isoindol-1-one. MS 427 (M + H$^+$). |
| 102 | 2-(1'-{[1-(4-Fluorophenyl)-1H-indol-5-yl]carbonyl}-1,3'-biazetidin-3-yl)-2,3-dihydro-1H-isoindol-1-one. MS 481 (M + H$^+$). |

Example 3

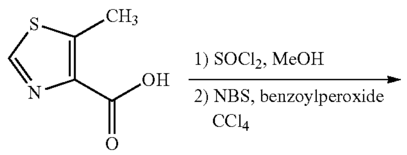

3a

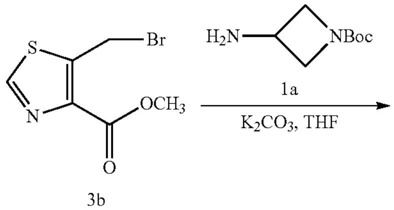

3b

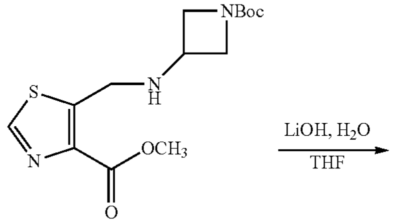

3c

-continued

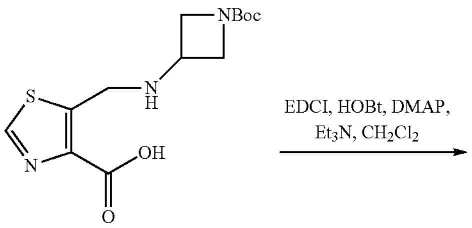

3d

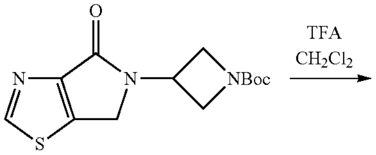

3e

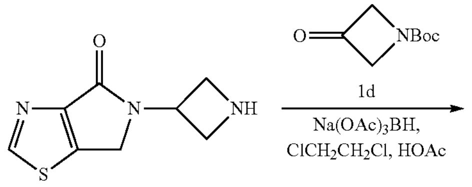

3f

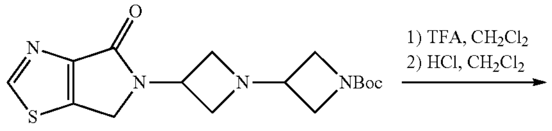

3g

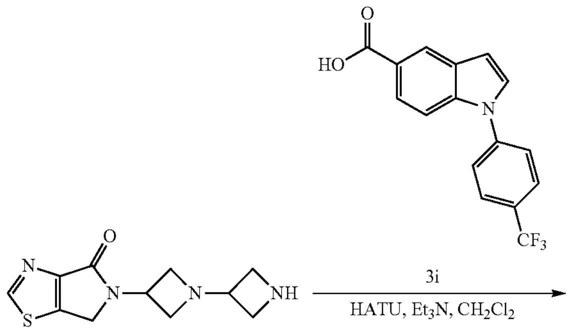

3h

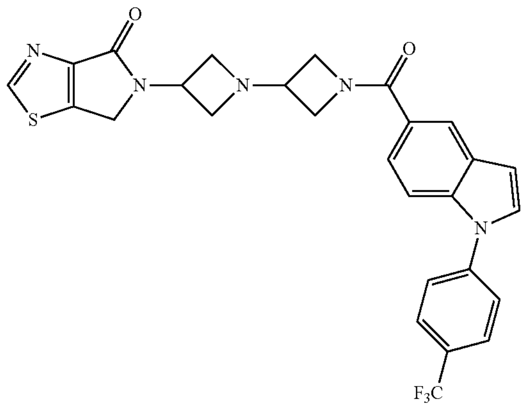

Cpd 106

A. Methyl 5-(bromomethyl)thiazole-4-carboxylate, 3b

To a mixture of 5-methylthiazole-4-carboxylic acid 3a (0.50 g, 3.49 mmol) in MeOH (15 mL) at 0° C. was added $SOCl_2$ (0.51 mL, 6.99 mmol). The reaction was warmed up to room temperature and then heated to reflux for 8 h. The reaction mixture was cooled to room temperature and concentrated. The residue was dissolved in $CH_2Cl_2$ and washed with aq. $NaHCO_3$. The organic solution was dried over $Na_2SO_4$ and concentrated. A portion of the resulting mixture (250 mg, 1.59 mmol) was heated to reflux in $CCl_4$ (15 mL) with NBS (311 mg, 1.75 mmol) and benzoyl peroxide (38.5 mg, 0.159 mmol) for 3 h. The reaction mixture was concentrated and purification by flash column chromatography (silica gel, 30% EtOAc/heptane) gave compound 3b (250 mg).

B. Methyl 5-(((1-(tert-butoxycarbonyl)azetidin-3-yl) amino)methyl)thiazole-4-carboxylate, 3c A mixture of compound 3b (250 mg, 1.06 mmol), 1-Boc-3-aminoazetidine 1a (310 mg, 1.80 mmol), and $K_2CO_3$ (248 mg, 1.80 mmol) in THF (12 mL) was heated to reflux for 6 h. The reaction mixture was cooled to room temperature and diluted with $CH_2Cl_2$. The resulting solution was washed with aq. $NaHCO_3$, dried over $Na_2SO_4$, and concentrated. Purification by flash column chromatography (silica gel, 3% MeOH/ $CH_2Cl_2$) gave compound 3c (210 mg).

C. tert-Butyl 3-(4-oxo-4H-pyrrolo[3,4-d]thiazol-5 (6H)-yl)azetidine-1-carboxylate, 3e A mixture of compound 3c (320 mg, 0.98 mmol) and $LiOH.H_2O$ (123 mg, 2.93 mmol) in THF (8 mL) and $H_2O$ (4 mL) was stirred at room temperature for 20 h. The pH of the reaction mixture was adjusted to 5 with aq. 10% HCl. Concentration gave the crude compound 3d. A mixture of compound 3d (0.98 mmol), HOBt (132 mg, 0.98 mmol), $Et_3N$ (0.41 mL, 2.93 mmol), EDCI (318 mg, 1.66 mmol), and DMAP (25 mg, 0.21 mmol) in DMF (4 mL) was heated at 65° C. for 5 h. The reaction mixture was cooled to room temperature and diluted with $CH_2Cl_2$. The solution was washed with $H_2O$, dried over $Na_2SO_4$ and concentrated. Purification by flash column chromatography (silica gel, 3% MeOH/ $CH_2Cl_2$) gave compound 3e (185 mg).

D. 5-[1'-({1-[4-(Trifluoromethyl)phenyl]-1H-indol-5-yl}carbonyl)-1,3'-biazetidin-3-yl]-5,6-dihydro-4H-pyrrolo[3,4-d][1,3]thiazol-4-one, Cpd 106

Compound 106 was prepared from intermediate 3e following the procedures described in Steps B and C of Example 1, except that 1-(4-trifluoromethylphenyl)indole-5-carboxylic acid was used in place of 4-phenylbenzoic acid. MS 538 ($M+H^+$).

Example 4

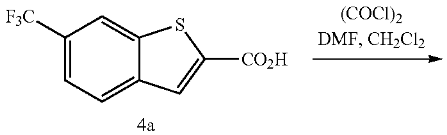

4a

-continued

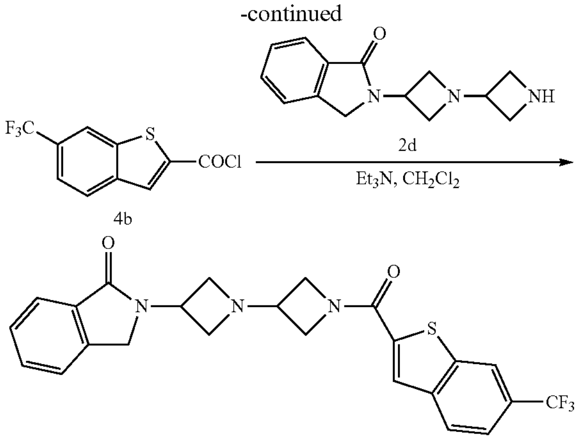

4b

Cpd 81

A. 6-(Trifluoromethyl)benzo[b]thiophene-2-carbonyl chloride, 4b

To a mixture of 6-(trifluoromethyl)benzo[b]thiophene-2-carboxylic acid 4a (65 mg, 0.26 mmol) in $CH_2Cl_2$ (2.5 mL) was added $(COCl)_2$ (0.026 mL, 0.30 mmol), followed by DMF (1 drop) at room temperature. The reaction was kept at room temperature for 20 h. The resulting solution was concentrated to give compound 4b.

B. 2-(1'-{[6-(Trifluoromethyl)-1-benzothiophen-2-yl]carbonyl}-1,3'-biazetidin-3-yl)-2,3-dihydro-1H-isoindol-1-one, Cpd 81

To a solution of compound 2d (0.24 mmol) and $Et_3N$ (0.08 mL, 0.58 mmol) in $CH_2Cl_2$ (3 mL) at 0° C. was added a solution of compound 4b (0.26 mmol) in $CH_2Cl_2$ (1 mL). The reaction was stirred at 0° C. for 4 h before it was quenched with aq. $NaHCO_3$. The mixture was extracted with $CH_2Cl_2$, and the organic solution was dried over $Na_2SO_4$ and concentrated. Purification by flash column chromatography (silica gel, 3% MeOH/$CH_2Cl_2$) gave compound 81 (57 mg). MS 472 ($M+H^+$).

Following the procedure described above for Example 4 and substituting the appropriate reagents, starting materials and purification methods known to those skilled in the art, the following compounds of the present invention were prepared:

| Cpd | Name and data |
|---|---|
| 7 | N-(1'-{[6-(Trifluoromethyl)-1-benzothiophen-2-yl[carbonyl}-1,3'-biazetidin-3-yl)-1,3-thiazole-2-carboxamide. MS 467 ($M + H^+$). |
| 8 | N-(1'-{[4-(Trifluoromethyl)-1-benzothiophen-2-yl[carbonyl}-1,3'-biazetidin-3-yl)-1,3-thiazole-2-carboxamide. MS 467 ($M + H^+$). |
| 47 | N-(1'-{[5-(Trifluoromethyl)-1,3-benzothiazol-2-yl[carbonyl}-1,3'-biazetidin-3-yl)-1,3-thiazole-2-carboxamide. MS 468 ($M + H^+$). |
| 49 | N-(1'-{[6-(Trifluoromethyl)-1-benzothiophen-2-yl[carbonyl}-1,3'-biazetidin-3-yl)-1,3-thiazole-4-carboxamide. MS 467 ($M + H^+$). |
| 50 | N-(1'-{[3-Chloro-6-(trifluoromethyl)-1-benzothiophen-2-yl]carbonyl}-1,3'-biazetidin-3-yl)-1,3-thiazole-2-carboxamide. MS 501 ($M + H^+$). |
| 51 | N-(1'-{[3-Chloro-6-(trifluoromethyl)-1-benzothiophen-2-yl]carbonyl}-1,3'-biazetidin-3-yl)-1,3-thiazole-4-carboxamide. MS 501 ($M + H^+$). |

-continued

| Cpd | Name and data |
|---|---|
| 56 | N-(1'-{[3-Methyl-6-(trifluoromethyl)-1-benzothiophen-2-yl]carbonyl}-1,3'-biazetidin-3-yl)-1,3-thiazole-2-carboxamide. $^1$H NMR (CHLOROFORM-d, 400 MHz): δ = 8.10 (s, 1 H), 7.88 (m, 2 H), 7.64 (d, J = 8.2 Hz, 2 H), 7.60 (d, J = 2.8 Hz 1 H), 4.76 (m, 1 H), 4.27 (br. s., 2 H), 4.05 (m, 2 H), 3.74 (m, 2 H), 3.54 (m, 1H), 3.21 (m, 2H), 2.66 ppm (s, 3 H). MS 481 (M + $H^+$). |
| 65 | N-{1'-[(6-Bromo-3-methyl-1-benzothiophen-2-yl)carbonyl]-1,3'-biazetidin-3-yl}-1,3-thiazole-2-carboxamide. MS 492 (M + $H^+$). |
| 67 | N-(1'-{[3-Methyl-6-(trifluoromethyl)-1-benzothiophen-2-yl]carbonyl}-1,3'-biazetidin-3-yl)-1,3-thiazole-4-carboxamide. $^1$H NMR (CHLOROFORM-d, 400 MHz): δ = 8.76 (d, J = 1.6 Hz, 1 H), 8.18 (d, J = 2.4 Hz, 1 H), 8.10 (s, 1H), 7.88 (d, J = 8.0 Hz, 1 H), 7.80 (d, J = 8.0 Hz, 1 H), 7.64 (d, J = 8.0 Hz, 1 H), 4.76 (m, 1 H), 4.28 (br. s., 2 H), 4.06 (br. s., 2 H), 3.75 (m, 2 H), 3.57 (m, 1H), 3.24 (m, 2H), 2.65 ppm (s, 3 H). MS 481 (M + $H^+$). |
| 73 | 2-{1'-[(6-Bromo-3-chloro-1-benzothiophen-2-yl)carbonyl]-1,3'-biazetidin-3-yl}-2,3-dihydro-1H-isoindol-1-one. MS 516 (M + $H^+$). |
| 87 | 2-{1'-[(6-Bromo-1-benzothiophen-2-yl)carbonyl]-1,3'-biazetidin-3-yl}-2,3-dihydro-1H-isoindol-1-one. MS 483 (M + $H^+$). |
| 93 | 2-{1'-[(5-Bromo-1-benzothiophen-2-yl)carbonyl]-1,3'-biazetidin-3-yl}-2,3-dihydro-1H-isoindol-1-one. MS 483 (M + $H^+$). |
| 99 | 2-(1'-{[3-Chloro-6-(trifluoromethyl)-1-benzothiophen-2-yl]carbonyl}-1,3'-biazetidin-3-yl)-2,3-dihydro-1H-isoindol-1-one. $^1$H NMR (CHLOROFORM-d, 400 MHz): δ = 8.13 (s, 1 H), 8.00 (d, J = 8.4 Hz, 1 H), 7.83 (d, J = 7.6 Hz, 1 H), 7.72 (dd, J = 1.2, 8.4 Hz 1 H), 7.46-7.59 (m, 3 H), 5.08 (m, 1 H), 4.61 (s, 2 H), 4.31 (m, 2 H), 4.11 (m, 2 H), 3.69 (m, 3 H), 3.49 ppm (m, 2 H). MS 506 (M + $H^+$). |
| 100 | 2-{1'-[(3-Chloro-6-fluoro-1-benzothiophen-2-yl)carbonyl]-1,3'-biazetidin-3-yl}-2,3-dihydro-1H-isoindol-1-one. MS 456 (M + $H^+$). |
| 101 | 2-(1'-{[3-Methyl-6-(trifluoromethyl)-1-benzothiophen-2-yl]carbonyl}-1,3'-biazetidin-3-yl)-2,3-dihydro-1H-isoindol-1-one. $^1$H NMR (CHLOROFORM-d, 400 MHz): δ = 8.10 (s, 1 H), 7.89 (d, J = 8.0 Hz, 1 H), 7.84 (d, J = 7.8 Hz, 1 H), 7.65 (d, J = 8.0 Hz, 1 H), 7.46-7.59 (m, 3H), 5.08 (m, 1 H), 4.61 (s, 2H), 4.30 (br. s., 2 H), 4.08 (m, 2 H), 3.69 (m, 2 H), 3.60 (m, 1H), 3.48 (m, 2H), 2.66 ppm (s, 3 H). MS 481 (M + $H^+$). MS 486 (M + $H^+$). |
| 103 | 5-(1'-{[3-Methyl-6-(trifluoromethyl)-1-benzothiophen-2-yl]carbonyl}-1,3'-biazetidin-3-yl)-5,6-dihydro-4H-pyrrolo[3,4-d][1,3]thiazol-4-one. MS 493 (M + $H^+$). |

Example 5

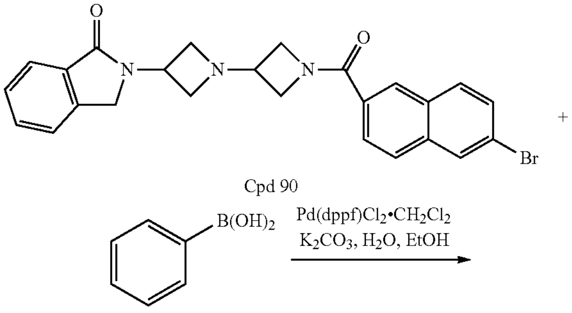

Cpd 90

-continued

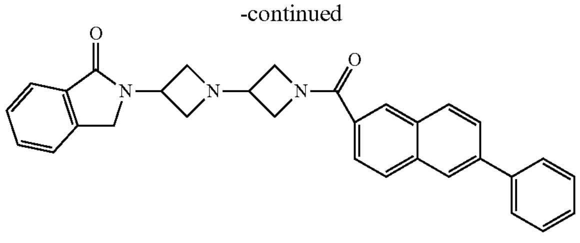

Cpd 69

2-{1'-[(6-Phenylnaphthalen-2-yl)carbonyl]-1,3'-biazetidin-3-yl}-2,3-dihydro-1H-isoindol-1-one, Cpd 69

A mixture of compound 90 (40 mg, 0.08 mmol), phenylboronic acid (21 mg, 0.17 mmol), $K_2CO_3$ (23 mg, 0.17 mmol), and $Pd(dppf)Cl_2.CH_2Cl_2$ (4 mg, 0.005 mmol) in EtOH (0.75 mL) and $H_2O$ (0.15 mL) was heated in a microwave reactor at 130° C. for 30 min. The mixture was diluted with $CH_2Cl_2$, washed with $H_2O$, dried over $Na_2SO_4$ and concentrated. Purification by flash column chromatography (silica gel, 3% MeOH/$CH_2Cl_2$) gave compound 69 (34 mg). MS 474 (M+$H^+$).

Following the procedure described above for Example 5 and substituting the appropriate reagents, starting materials and purification methods known to those skilled in the art, the following compounds of the present invention were prepared:

| Cpd | Name and data |
|---|---|
| 2 | N-(1'-{[3'-(Trifluoromethyl)biphenyl-4-yl]carbonyl}-1,3'-biazetidin-3-yl)-1,3-thiazole-4-carboxamide. $^1$H NMR (CHLOROFORM-d, 400 MHz): δ = 8.77 (s, 1 H), 8.18 (d, J = 2.4 Hz, 1 H), 7.84 (s, 1 H), 7.57-7.79 (m, 8 H), 4.78 (m, 1 H), 4.33 (m, 1 H), 4.25 (m, 1 H), 4.12 (m, 1 H), 4.04 (m, 1 H), 3.75 (m, 2 H), 3.54 (m, 1 H), 3.20 ppm (m, 2 H). MS 487 (M + $H^+$). |
| 5 | N-(1'-{[3'-(Trifluoromethyl)biphenyl-4-yl] carbonyl}-1,3'-biazetidin-3-yl)-1,3-thiazole-2-carboxamide. $^1$H NMR (CHLOROFORM-d, 400 MHz): δ = 7.56-7.87 (m, 10 H), 4.76 (m, 1 H), 4.33 (s, 1 H), 4.25 (m, 1 H), 4.12 (m, 1 H), 4.03 (m, 1 H), 3.74 (m, 2 H), 3.54 (m, 1 H), 3.22 ppm (br. s., 2 H). MS 487 (M + $H^+$). |
| 6 | N-{1'-[(6-Phenyl-1-benzothiophen-2-yl)carbonyl]-1,3'-biazetidin-3-yl}-1,3-thiazole-2-carboxamide. MS 475 (M + $H^+$). |
| 12 | N-(1'-{[4'-(Trifluoromethyl)biphenyl-4-yl]carbonyl}-1,3'-biazetidin-3-yl)-1,3-thiazole-2-carboxamide. MS 487 (M + $H^+$). |
| 14 | N-(1'-{[4'-(Trifluoromethyl)biphenyl-4-yl]carbonyl}-1,3'-biazetidin-3-yl)-1,3-thiazole-4-carboxamide. MS 487 (M + $H^+$). |
| 18 | N-(1'-{[3'-(Methylsulfonyl)biphenyl-4-yl]carbonyl}-1,3'-biazetidin-3-yl)-1,3-thiazole-2-carboxamide. MS 497 (M + $H^+$). |
| 21 | N-{1'-[(6-Phenylnaphthalen-2-yl)carbonyl]-1,3'-biazetidin-3-yl}-1,3-thiazole-2-carboxamide. MS 469 (M + $H^+$). |
| 25 | N-{1'-[(5-Phenylnaphthalen-2-yl)carbonyl]-1,3'-biazetidin-3-yl}benzamide. MS 462 (M + $H^+$). |
| 34 | N-{1'-[(6-Phenylnaphthalen-2-yl)carbonyl]-1,3'-biazetidin-3-yl}benzamide. MS 462 (M + $H^+$). |
| 53 | N-{1'-[(5-Phenylnaphthalen-2-yl)carbonyl]-1,3'-biazetidin-3-yl}-1,3-thiazole-2-carboxamide. MS 469 (M + $H^+$). |
| 58 | N-(1'-{[3-Methyl-3'-(trifluoromethyl)biphenyl-4-yl[carbonyl}-1,3'-biazetidin-3-yl)-1,3-thiazole-2-carboxamide. MS 501 (M + $H^+$). |
| 59 | N-(1'-{[3-Fluoro-4'-(trifluoromethyl)biphenyl-4-yl[carbonyl}-1,3'-biazetidin-3-yl)-1,3-thiazole-2-carboxamide. MS 505 (M + $H^+$). |

-continued

| Cpd | Name and data |
|---|---|
| 63 | N-(1'-{[3-Methyl-4'-(trifluoromethyl)biphenyl-4-yl[carbonyl}-1,3'-biazetidin-3-yl)-1,3-thiazole-2-carboxamide. MS 501 (M + H$^+$). |
| 64 | N-(1'-{[3-Fluoro-3'-(trifluoromethyl)biphenyl-4-yl[carbonyl}-1,3'-biazetidin-3-yl)-1,3-thiazole-2-carboxamide. MS 505 (M + H$^+$). |
| 66 | N-{1'-[(3-Methyl-6-phenyl-1-benzothiophen-2-yl)carbonyl]-1,3'-biazetidin-3-yl}-1,3-thiazole-2-carboxamide. MS 489 (M + H$^+$). |
| 68 | 2-{1'-[(3-Chloro-6-phenyl-1-benzothiophen-2-yl)carbonyl]-1,3'-biazetidin-3-yl}-2,3-dihydro-1H-isoindol-1-one. MS 515 (M + H$^+$). |
| 72 | 2-[1'-((6-[3-(Methylsulfonyl)phenyl]-1-benzothiophen-2-yl}carbonyl)-1,3'-biazetidin-3-yl]-2,3-dihydro-1H-isoindol-1-one. MS 558 (M + H$^+$). |
| 74 | 2-{1'-[(3,6-Diphenyl-1-benzothiophen-2-yl)carbonyl]-1,3'-biazetidin-3-yl}-2,3-dihydro-1H-isoindol-1-one. MS 556 (M + H$^+$). |
| 79 | 2-{1'-[(5-Phenyl-1-benzothiophen-2-yl)carbonyl]-1,3'-biazetidin-3-yl}-2,3-dihydro-1H-isoindol-1-one. $^1$H NMR (CHLOROFORM-d, 400 MHz): δ = 8.04 (d, J = 1.6 Hz, 1 H), 7.92 (d, J = 8.4 Hz, 1 H), 7.84 (d, J = 7.6 Hz, 1 H), 7.76 (s, 1 H), 7.36-7.69 (m, 9 H), 5.09 (m, 1 H), 4.63 (s, 2 H), 4.58 (m, 1 H), 4.39 (m, 1 H), 4.29 (m, 1 H), 4.09 (m, 1 H), 3.70 (m, 2 H), 3.66 (m, 1 H), 3.51 ppm (br. s., 2 H). MS 480 (M + H$^+$). |
| 80 | 2-(1'-{[3'-(Methylsulfonyl)biphenyl-4-yl]carbonyl}-1,3'-biazetidin-3-yl)-2,3-dihydro-1H-isoindol-1-one. MS 502 (M + H$^+$). |
| 82 | 2-[1'-((5-[3-(Methylsulfonyl)phenyl]-1-benzothiophen-2-yl}carbonyl)-1,3'-biazetidin-3-yl]-2,3-dihydro-1H-isoindol-1-one. MS 558 (M + H$^+$). |
| 95 | 2-(1'-{[4-(1-benzothiophen-2-yl)phenyl]carbonyl}-1,3'-biazetidin-3-yl)-2,3-dihydro-1H-isoindol-1-one. MS 480 (M + H$^+$). |
| 97 | 2-{1'-[(5-Phenylnaphthalen-2-yl)carbonyl]-1,3'-biazetidin-3-yl}-2,3-dihydro-1H-isoindol-1-one. MS 474 (M + H$^+$). |
| 98 | 2-{1'-[(6-Phenyl-1-benzothiophen-2-yl)carbonyl]-1,3'-biazetidin-3-yl}-2,3-dihydro-1H-isoindol-1-one. MS 480 (M + H$^+$). |
| 104 | 5-(1'-{[3-Methyl-3'-(trifluoromethyl)biphenyl-4-yl]carbonyl}-1,3'-biazetidin-3-yl)-5,6-dihydro-4H-pyrrolo[3,4-d][1,3]thiazol-4-one. MS 513 (M + H$^+$). |
| 105 | 5-(1'-{[3-Methyl-4'-(trifluoromethyl)biphenyl-4-yl[carbonyl}-1,3'-biazetidin-3-yl)-5,6-dihydro-4H-pyrrolo[3,4-d][1,3]thiazol-4-one. MS 513 (M + H$^+$). |

Example 6

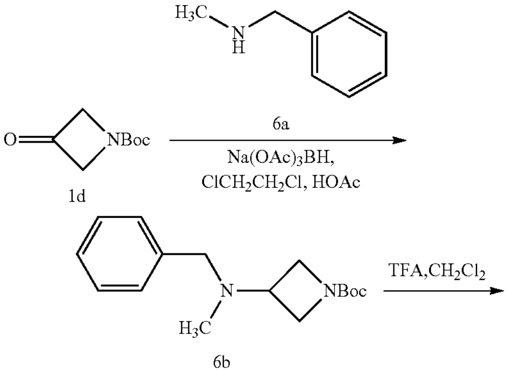

6b

-continued

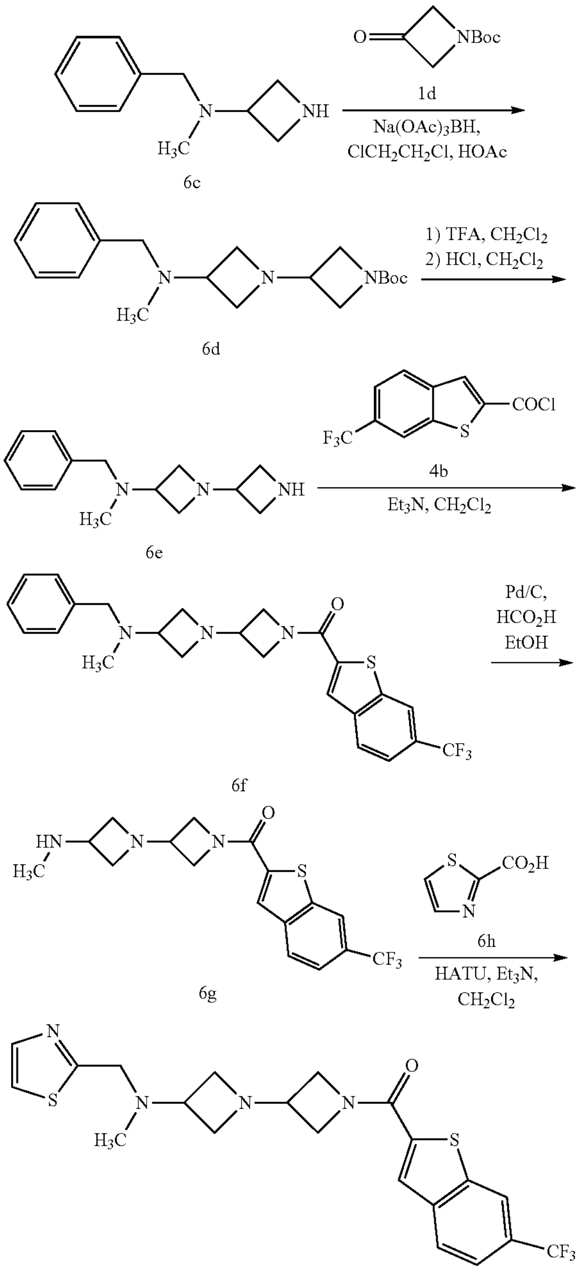

Cpd 37

A. tert-Butyl 3-(benzyl(methyl)amino)azetidine-1-carboxylate, 6b

To a solution of 1-Boc-azetidin-3-one 1d (1.0 g, 5.85 mmol) and N-methyl-benzylamine 6a (1.02 g, 8.43 mmol) in 1,2-dichloroethane (12 mL) and acetic acid (1 mL) was added $Na(OAc)_3BH$ (1.30 g, 6.13 mmol). The reaction mixture was stirred at room temperature for 20 h. The reaction was quenched by the addition of aq. $NaHCO_3$. The resulting mixture was extracted with $CH_2Cl_2$. The organic solution was dried over $Na_2SO_4$ and concentrated. Purification by flash column chromatography (silica gel, 40% EtOAc/heptane) gave compound 6b (1.40 g).

B. tert-Butyl 3-(benzyl(methyl)amino)-[1,3'-biazetidine]-1'-carboxylate, 6d

Intermediate 6d was prepared following the procedure described in Step B of Example 1.

C. (3-(Benzylmethyl)amino)-[1,3'-biazetidin]-1'-yl)(6-(trifluoromethyl)benzo[b]thiophen-2-yl)methanone, 6f Intermediate 6f was prepared following the procedure described in Example 4.

D. N-Methyl-N-(1'-{[6-(trifluoromethyl)-1-benzothiophen-2-yl]carbonyl}-1,3'-biazetidin-3-yl)-1,3-thiazole-2-carboxamide, Cpd 37

A mixture of compound 6f (53 mg, 0.12 mmol), $HCO_2H$ (0.2 mL), and Pd/C (50 mg) in EtOH (4 mL) was stirred at room temperature for 24 h. Additional $HCO_2H$ (0.2 mL) and Pd/C (50 mg) was added. The reaction was stirred for another 24 h. The mixture was filtered and the solution was concentrated. The residue was dissolved in $CH_2Cl_2$ and washed with 1N NaOH, dried over $Na_2SO_4$, and concentrated to give compound 6g (34 mg). A mixture of compound 6g (34 mg, 0.09 mmol), 2-thiazole-carboxylic acid 6h (24 mg, 0.19 mmol), $Et_3N$ (0.05 mL, 0.36 mmol), and HATU (70 mg, 0.18 mmol) in $CH_2Cl_2$ (3 mL) was stirred at room temperature for 20 h. The reaction mixture was diluted with ethyl ether and washed with aq. $NaHCO_3$ and aq. NaCl. The organic solution was dried over $Na_2SO_4$ and concentrated. Purification by flash column chromatography (silica gel, 3% $MeOH/CH_2Cl_2$) gave compound 37 (11 mg). MS 481 ($M+H^+$).

Following the procedure described above for Example 6 and substituting the appropriate reagents, starting materials and purification methods known to those skilled in the art, the following compound of the present invention was prepared:

| Cpd | Name and data |
|---|---|
| 48 | N-Methyl-N-(1'-{[6-(trifluoromethyl)-1-benzothiophen-2-yl]carbonyl}-1,3'-biazetidin-3-yl)-1,3-thiazole-4-carboxamide. MS 481 ($M + H^+$). |

Examples 7-28 provide synthetic routes to useful intermediates for the preparation of compounds of Formula (I).

Example 7

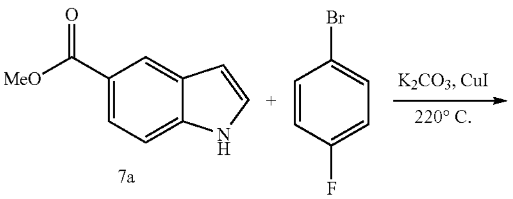

7a

7b

-continued

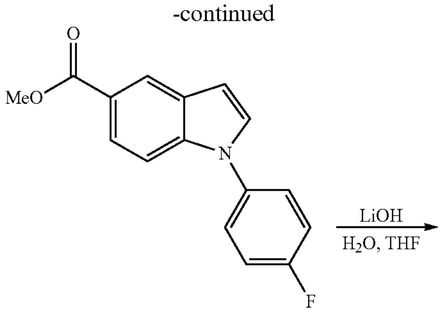

7c

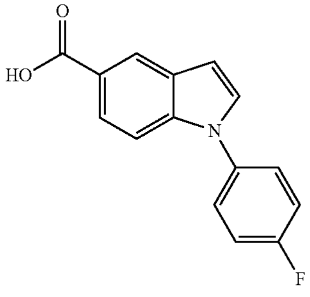

7d

A. Methyl 1-(4-fluorophenyl)-indole-5-carboxylate, 7d

A mixture of methyl indole-5-carboxylate 7a (0.5 g, 2.85 mmol), 1-bromo-4-fluoro-benzene 7b (2 mL, 18.21 mmol), CuI (0.544 g, 2.85 mmol), and $K_2CO_3$ (0.591 g, 4.28 mmol) was heated under microwave at 220° C. for 2.5 hours. The reaction mixture was diluted with $CH_2Cl_2$ and filtered. The solution was concentrated and the residue was purified by flash column chromatography (silica gel, 15% EtOAc/heptane) to give 7c (0.58 g).

B. 1-(4-fluorophenyl)-indole-5-carboxylic acid, 7d

A mixture of methyl 1-(4-fluorophenyl)-indole-5-carboxylate 7c (0.58 g, 2.15 mmol) and $LiOH.H_2O$ (0.36 g, 8.6 mmol) in THF (15 mL) and $H_2O$ (10 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 7d (0.5 g).

Following the procedure described above for Example 7 and substituting the appropriate reagents, starting materials, and purification methods known to those skilled in the art, the following intermediate was prepared:

Cpd 7e

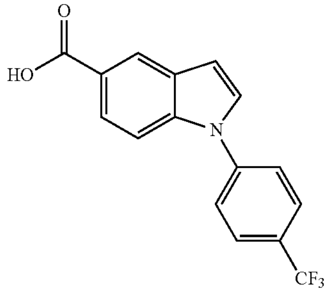

Example 8

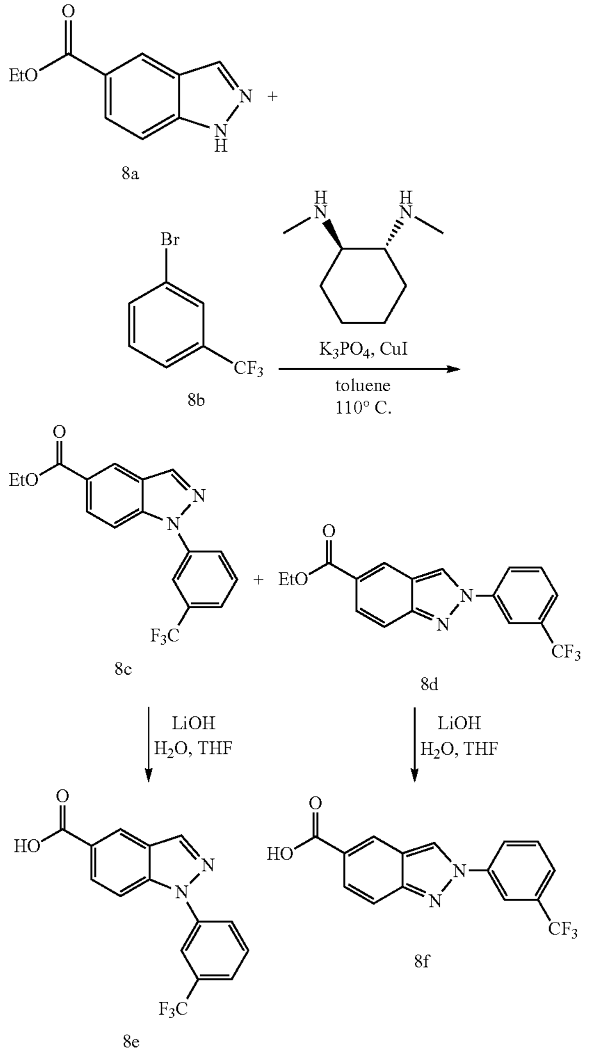

8a 8b 8c 8d 8e 8f

A. Ethyl 1-(3-trifluoromethyl-phenyl)-1H-indazole-5-carboxylate, 8c and Ethyl 2-(3-trifluoromethyl-phenyl)-2H-indazole-5-carboxylate, 8d A mixture of ethyl 1H-indazole-5-carboxylate 8a (150 mg, 0.79 mmol), 1-bromo-3-trifluoromethylbenzene 8b (0.13 mL, 0.95 mmol), CuI (22.5 mg, 0.12 mmol), trans-N,N'-dimethylcyclohexane-1,2-diamine (0.056 mL, 0.36 mmol), and $K_3PO_4$ (0.37 g, 1.74 mmol) in toluene (1.5 mL) was heated at 110° C. for 16 hours. The reaction mixture was diluted with $CH_2Cl_2$ and filtered. The solution was concentrated and the residue was purified by flash column chromatography (silica gel, 10% EtOAc/heptane) to give 8c (190 mg), followed by 8d (37 mg).

B. 1-(3-Trifluoromethyl-phenyl)-1H-indazole-5-carboxylic acid, 8e and 2-(3-Trifluoromethyl-phenyl)-2H-indazole-5-carboxylic acid, 8f A mixture of 8c and 8d and LiOH in THF (120 mL) and $H_2O$ (60 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 8e and 8f.

Example 9

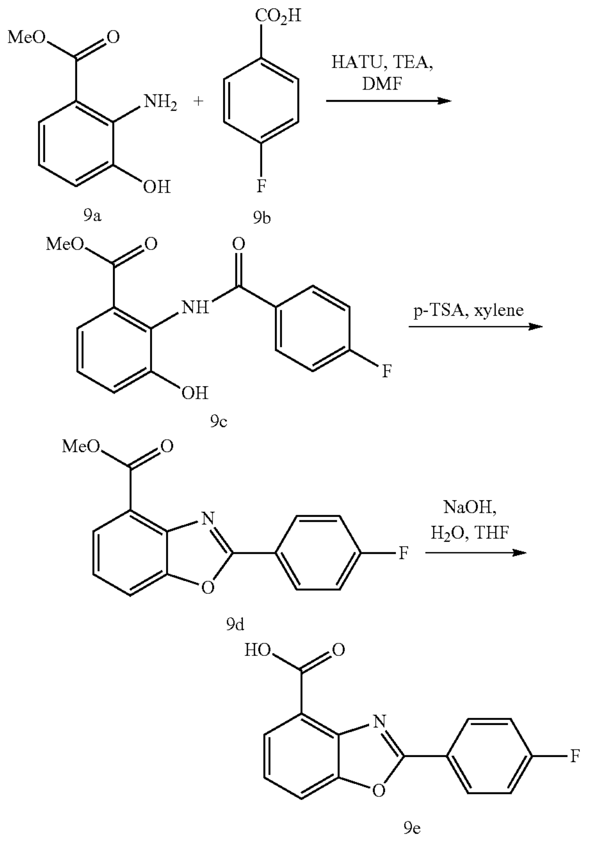

9a 9b 9c 9d 9e

A. Methyl 2-(4-fluoro-benzoylamino)-3-hydroxy-benzoate, 9c

A solution of 1.0 g (4.9 mmol) of methyl 2-amino-3-hydroxybenzoate 9a, 1.03 g (7.4 mmol) of 4-fluorobenzoic acid 9b, 10 mL DMF and 2.9 mL (20.6 mmol) of TEA were placed into a flask and stirred for 10 min. HATU (7.4 mmol, 2.8 g) was added and the reaction was stirred overnight. The reaction mixture was poured into water and extracted with EtOAc. The organics were washed with water and brine and the solvent was evaporated to give 1.2 g of crude product, methyl 2-(4-fluoro-benzoylamino)-3-hydroxy-benzoate, 9c, which was used without purification. MS m/z ($M+H^+$) 290.1.

B. Methyl 2-(4-fluorophenyl)benzo[d]oxazole-4-carboxylate, 9d

Methyl 2-(4-fluoro-benzoylamino)-3-hydroxy-benzoate 9c (7.4 mmol, 1.2 g crude) and 1.3 g (7.5 mmol) of p-toluenesulfonic acid were refluxed in 10 mL of xylene overnight. After cooling saturated $NaHCO_3$ was added and the resulting mixture was extracted with EtOAc. The organic solvent was evaporated to give 1.1 g (55%) of methyl 2-(4-fluorophenyl) benzo[d]oxazole-4-carboxylate, 9d. MS m/z ($M+H^+$) 272.0.

C. 2-(4-Fluorophenyl)-benzo[d]oxazole-4-carboxylic acid, 9e

A mixture of 1.1 g (4.0 mmol) methyl 2-(4-fluorophenyl) benzo[d]oxazole-4-carboxylate 9d and 3.7 mL of 3N aqueous NaOH in 10 mL of THF was refluxed overnight. After cooling the reaction mixture was poured into water and acidified with conc. HCl. The resulting solid was filtered and dried to give 830 mg (79%) of 2-(4-fluorophenyl)-benzo[d]oxazole-4-carboxylic acid, 9e. MS m/z (M+H$^+$) 258.1.

Following the procedure described above for Example 9, and substituting the appropriate reagents, starting materials, and purification methods known to those skilled in the art, the following intermediate compounds were prepared:

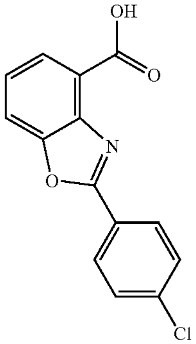

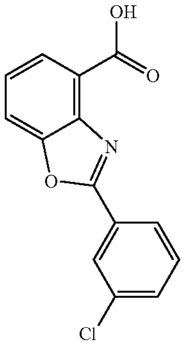

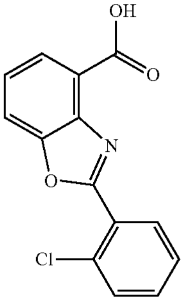

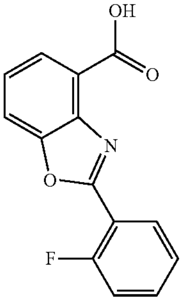

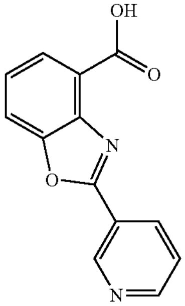

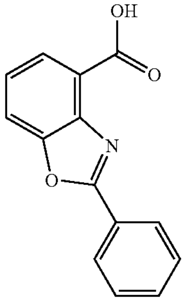

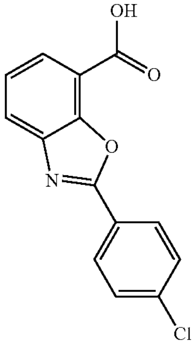

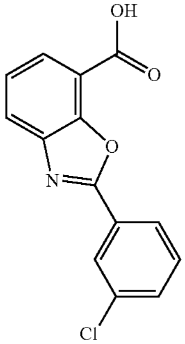

-continued

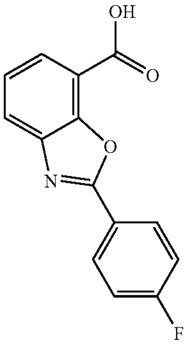

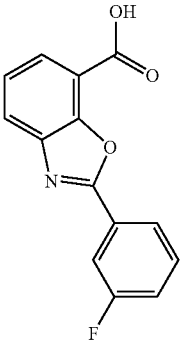

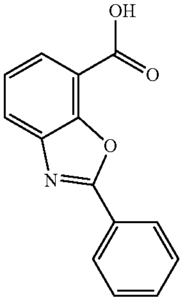 [SMILES: O=C(O)c1cccc2nc(-c3ccccc3)oc12]

Example 10

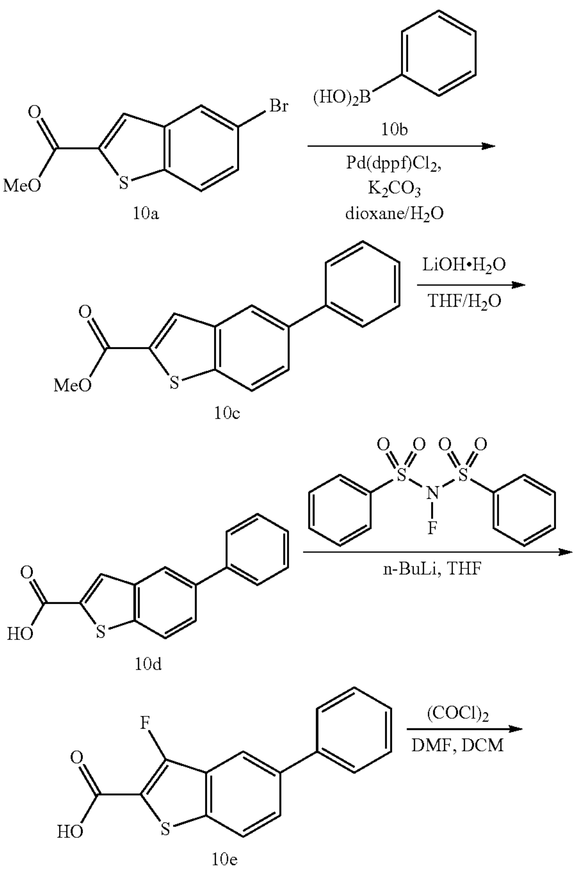

-continued

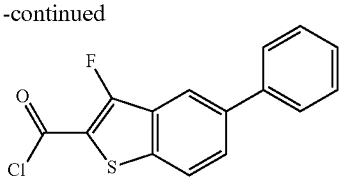

10f

A. Methyl 5-phenyl-benzo[b]thiophene-2-carboxylate, 10c

A mixture of compound 10a (542.3 mg, 2 mmol), phenyl boronic acid 10b (268.2 mg, 2.2 mmol), $Pd(dppf)Cl_2.CH_2Cl_2$ (98 mg, 0.12 mmol), and $K_2CO_3$ (414.6 mg, 3 mmol), in a dioxane (4 mL)/water (1 mL) mixture, was placed in a capped vial and heated at 80° C. overnight. The reaction mixture was then diluted with EtOAc and water. The organic layer was concentrated under reduced pressure and purified by flash column chromatography (silica gel, 2-10% EtOAc/heptane) to give compound 10c (510 mg). MS m/z $(M+H^+)$ 269.1.

B. 5-Phenyl-benzo[b]thiophene-2-carboxylic acid, 10d

A solution of compound 10c (510 mg, 1.9 mmol) and $LiOH.H_2O$ (319 mg, 7.6 mmol) in $THF/H_2O$ (10/10 mL) was stirred at room temperature overnight. The resulting mixture was concentrated and diluted with water. The water layer was acidified with 1N aqueous HCl to pH~4 and extracted with $CH_2Cl_2$. The organic solution was dried over $Na_2SO_4$ and concentrated to give 10d (479 mg), which was used in the next reaction without further purification. MS m/z $(M+H^+)$ 255.0.

C. 3-Fluoro-5-phenyl-benzo[b]thiophene-2-carboxylic acid, 10e

To a solution of compound 10d (507 mg, 1.99 mmol) in THF (8 mL) at −70° C. was added n-BuLi (1.6 M in hexane, 2.62 mL, 4.19 mmol). The mixture was stirred at −70° C. for 1 h; then a solution of N-fluorobenzenesulfonimide (817.3 mg, 2.59 mmol) in THF (2 mL) was slowly added. The reaction mixture was allowed to warm to room temperature and was stirred overnight. The resulting mixture was partitioned between dilute aqueous HCl and EtOAc. The organic solution was washed with water and brine, dried over $Na_2SO_4$, and concentrated. The residue was triturated with $CH_2Cl_2$, filtered and the solid dried to give compound 10e (391.9 mg). MS m/z $(M+H^+)$ 273.0.

D. 3-Fluoro-5-phenyl-benzo[b]thiophene-2-carbonyl chloride, 10f

To a solution of compound 10e (136.2 mg, 0.5 mmol) in $CH_2Cl_2$ (5 mL) at room temperature was added $(COCl)_2$ (0.064 mL, 0.75 mmol), followed by DMF (0.01 mL, 0.125 mmol). The reaction mixture was stirred at room temperature for 18 h. The reaction mixture was then concentrated to give compound 10f (light pink powder).

Example 11

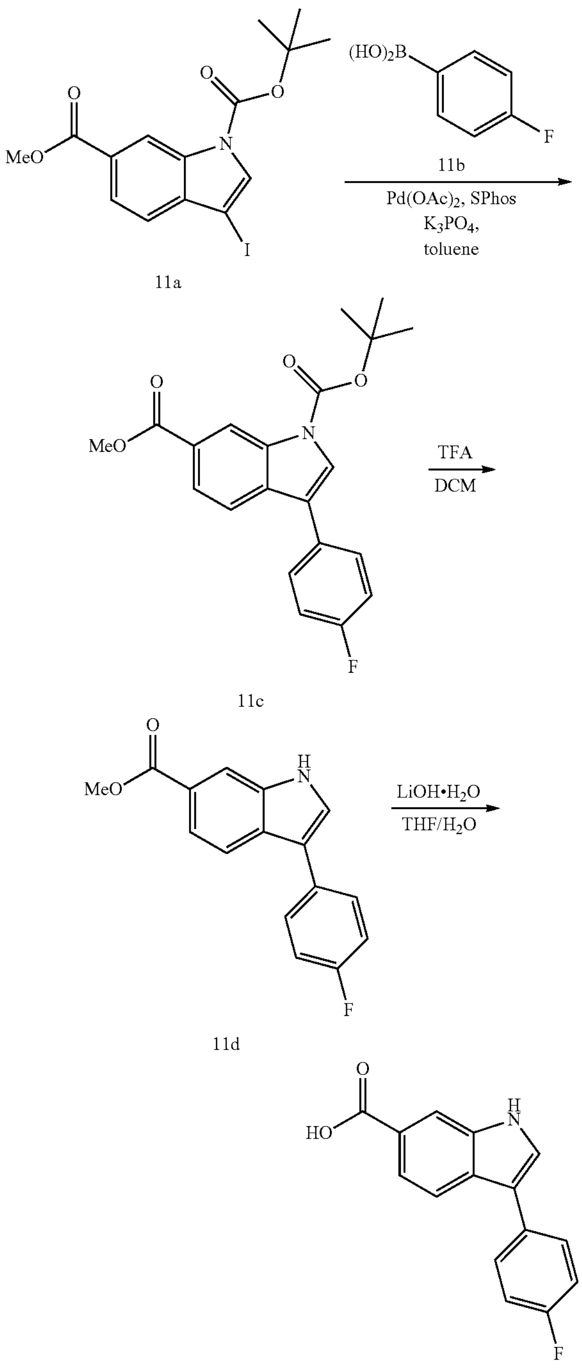

11a, 11c, 11d, 11e

A. 1-tert-Butyl 6-methyl 3-(4-fluorophenyl)-1H-indole-1,6-dicarboxylate, 11c A mixture of compound 11a (1.00 g, 2.49 mmol), 4-fluorophenyl boronic acid 11b (523 mg, 3.74 mmol), $Pd(OAc)_2$ (44.8 mg, 0.2 mmol), 2-dicyclohexylphosphino-2',6'-dimethoxybiphenyl (SPhos, 204.7 mg, 0.5 mmol), and $K_3PO_4$ (1.06 g, 4.99 mmol), in toluene (5 mL) was placed in a capped vial and heated at 90° C. under $N_2$ for 3 h. The reaction mixture was then diluted with EtOAc and water. The organic layer was washed with brine, concentrated under reduced pressure, and purified by flash column chromatography (silica gel, 2-10% EtOAc/heptane) to give compound 11c as a light yellow solid, which was further recrystallized from heptane to obtain white solid (707 mg). MS m/z ($M+H^+$) 370.2.

B. Methyl 3-(4-fluorophenyl)-1H-indole-6-carboxylate, 11d

To a solution of compound 11c (705 mg, 1.91 mmol) in $CH_2Cl_2$ (4 mL) was added trifluoroacetic acid (1.5 mL) at room temperature. The mixture was stirred at room temperature for 2 h. The resulting mixture was concentrated to give compound 11d (603.3 mg) as a white solid. MS m/z ($M+H^+$) 270.1.

C. 3-(4-Fluorophenyl)-1H-indole-6-carboxylic acid, 11e

A solution of compound 11d (303 mg, 0.79 mmol), and $LiOH.H_2O$ (132.7 mg, 3.16 mmol) in $THF/H_2O$ (10 mL/10 mL) was stirred at 45° C. for 5 h. The resulting mixture was concentrated and diluted with water. The water layer was acidified with 1N aqueous HCl to pH~4 and extracted with $CH_2Cl_2$. The organic solution was dried over $Na_2SO_4$ and concentrated to give 11e (249 mg). MS m/z ($M+H^+$) 256.0.

Following the procedure described above for Example 11, and substituting the appropriate reagents, starting materials and purification methods known to those skilled in the art, the following intermediate compounds were prepared:

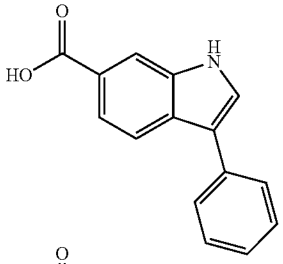

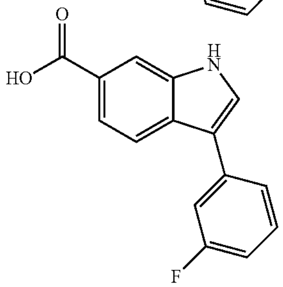

Example 12

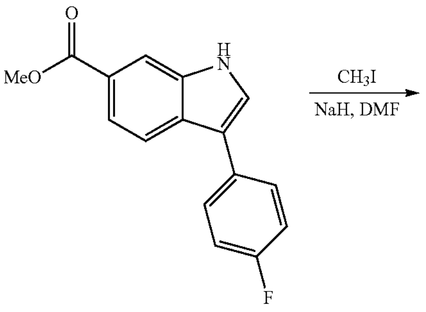

11d

-continued

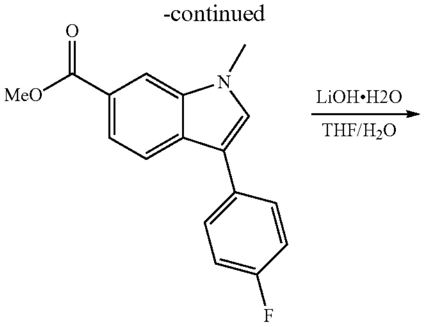

12a

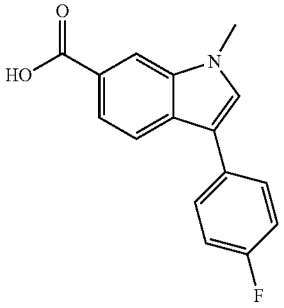

12b

A. Methyl 3-(4-fluorophenyl)-1-methyl-1H-indole-6-carboxylate, 12a

To a solution of compound 11d (300 mg, 0.78 mmol) in DMF (3 mL) was added NaH (60% in mineral oil, 68.9 mg, 1.72 mmol) at 0° C. The mixture was stirred at 0° C. for 30 min, then $CH_3I$ (0.053 mL, 0.86 mmol) was added and stirring continued at 0° C. for another 1 h. The resulting mixture was diluted with EtOAc and water. The organic layer was washed with brine and concentrated. The residue was recrystallized from heptane, filtered and the solid dried to give compound 12a (265 mg) as a light yellow solid. MS m/z ($M+H^+$) 284.1.

B. 3-(4-Fluoro-phenyl)-1-methyl-1H-indole-6-carboxylic acid, 12b

A solution of compound 12a (264 mg, 0.93 mmol) and $LiOH.H_2O$ (156.4 mg, 3.73 mmol) in $THF/H_2O$ (10 mL/10 mL) was stirred at 45° C. for 5 h. The resulting mixture was concentrated and diluted with water. The water layer was acidified with 1N aqueous HCl to pH~4 and extracted with $CH_2Cl_2$. The organic solution was dried over $Na_2SO_4$ and concentrated to give compound 12b (252 mg). MS m/z ($M+H^+$) 270.1.

Following the procedure described above for Example 12 and substituting the appropriate reagents, starting materials and purification methods known to those skilled in the art, the following intermediate compound was prepared:

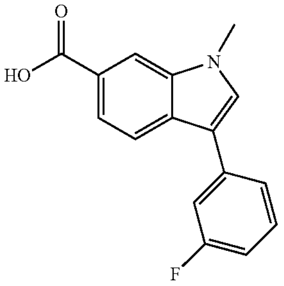 [SMILES: Cn1cc(-c2cccc(F)c2)c2ccc(C(=O)O)cc21]

Example 13

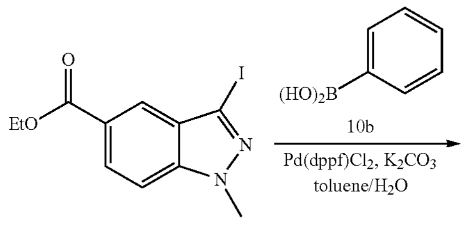

13a

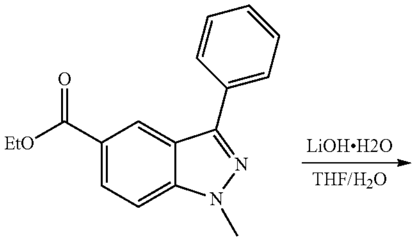

13b

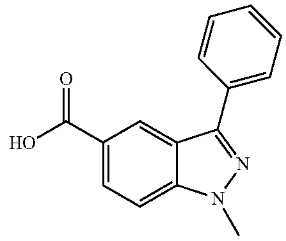

13c

A. Ethyl 1-Methyl-3-phenyl-1H-indazole-5-carboxylate, 13b

A mixture of compound 13a (300 mg, 0.91 mmol), phenyl boronic acid 10b (133 mg, 1.09 mmol), $Pd(dppf)Cl_2.CH_2Cl_2$ (40 mg, 0.055 mmol), and $K_2CO_3$ (251.2 mg, 1.82 mmol), in a toluene (2 mL)/water (0.4 mL) mixture, was placed in a capped vial and heated at 90° C. overnight. The reaction mixture was then diluted with EtOAc and water. The organic layer was concentrated under reduced pressure and purified by flash column chromatography (silica gel, 2-10% EtOAc/Heptanes) to give compound 13b (231 mg). MS m/z ($M+H^+$) 281.1.

B. 1-Methyl-3-phenyl-1H-indazole-5-carboxylic acid, 13c

A solution compound 13b (230 mg, 0.58 mmol), and $LiOH.H_2O$ (98 mg, 2.33 mmol) in $THF/H_2O$ (10/10 mL) was stirred at 45° C. for 8 h. The resulting mixture was concentrated and diluted with water. The water layer was acidified with 1N aqueous HCl to pH~4 and extracted with $CH_2Cl_2$. The organic solution was dried over $Na_2SO_4$ and concentrated to give 13c (206 mg). MS m/z ($M+H^+$) 253.1.

Following the procedure described above for Example 13 and substituting the appropriate reagents, starting materials and purification methods known to those skilled in the art, the following intermediate compounds were prepared:

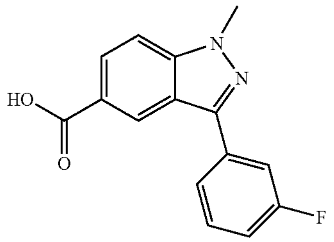

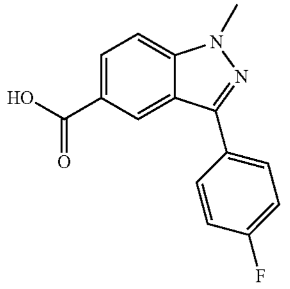

Example 14

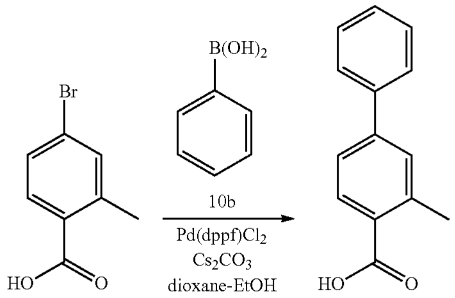

14a 14b

A. 3-Methyl-[1,1'-biphenyl]-4-carboxylic acid, 14b

To a suspension of compound 14a (0.025 g, 0.115 mmol), compound 10b (0.0139 g, 0.14 mmol), and $Cs_2CO_3$ (0.094 g, 0.288 mmol) in dioxane (3 mL) and EtOH (1 mL) was added $Pd(dppf)Cl_2$ (0.0084 g, 0.0115 mmol). The reaction mixture was stirred at 80° C. for 3 h. After cooling, the solid was removed by filtration and washed with $CH_3OH$. The filtrate was concentrated. The crude product 14b was purified by reverse phase chromatography. MS m/z ($M+H^+$) 213.1.

Following the procedure described above for Example 14 and substituting the appropriate reagents, starting materials and purification methods known to those skilled in the art, the following intermediate compounds were prepared:

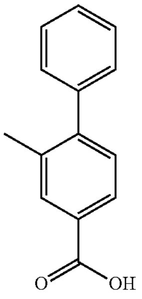

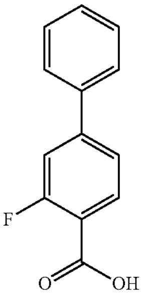

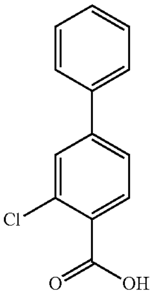

-continued

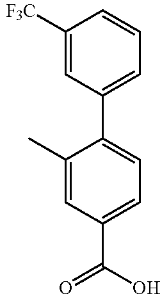

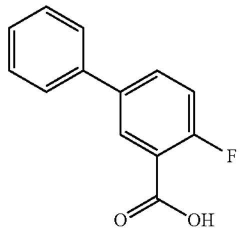

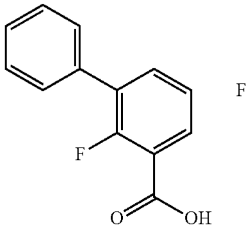

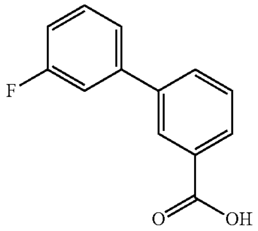

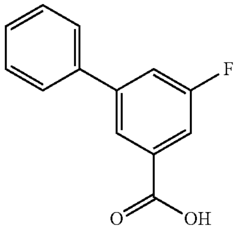

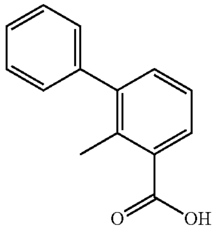

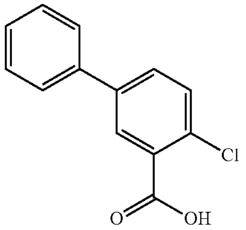

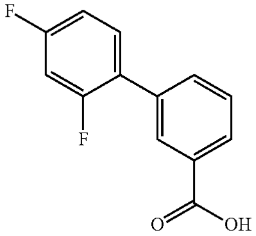

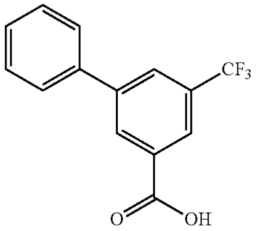

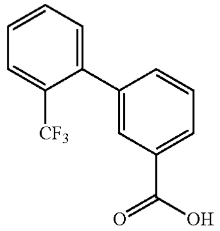

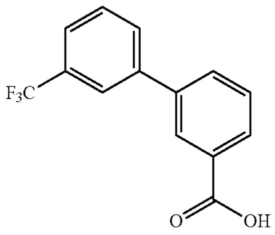

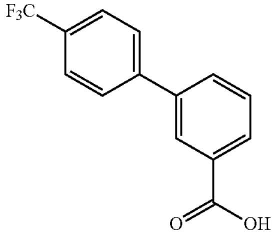

Example 15

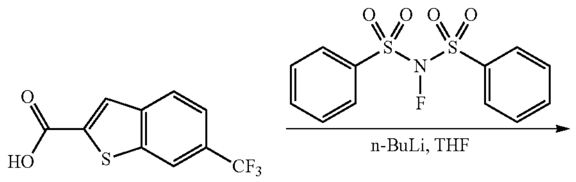

15a

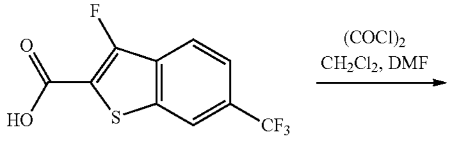

15b

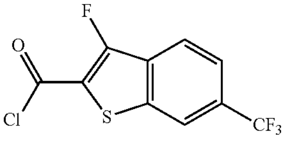

15c

A. 3-Fluoro-6-trifluoromethyl-benzo[b]thiophene-2-carboxylic acid, 15b

A solution of 6-trifluoromethyl-benzo[b]thiophene-2-carboxylic acid 15a (2.031 mmol, 0.50 g) in THF (8 mL) at −70° C. was treated with a 1.6 M solution of n-BuLi in hexanes (4.26 mmol, 2.66 mL). After 1 h at −70° C., N-fluorobenzenesulfonimide (2.64 mmol, 0.833 g) in THF (2 mL) was slowly added and the reaction was warmed to room temperature. After 1 h the mixture was partitioned between dilute aqueous HCl and EtOAc. The organic layer was washed with water and brine, and then concentrated. The residue was triturated with $CH_2Cl_2$. The off-white precipitate was filtered and collected to provide 15b.

B. 3-Fluoro-6-trifluoromethyl-benzo[b]thiophene-2-carbonyl chloride, 15c

To compound 15b (0.14 g, 0.53 mmol) in $CH_2Cl_2$ (5 mL) at room temperature was added $(COCl)_2$ (0.051 mL, 0.58 mmol), followed by 2 drops of DMF. The reaction mixture was stirred at room temperature for 18 h. The reaction mixture was then concentrated to give compound 15c.

Example 16

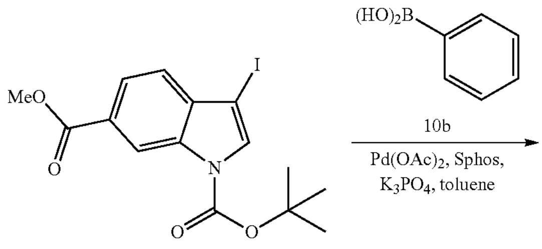

11a

-continued

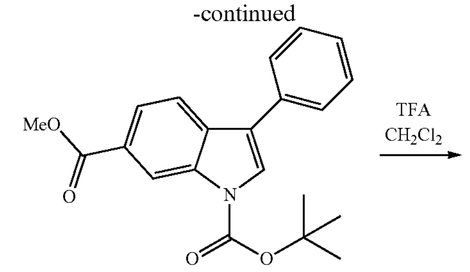

16a

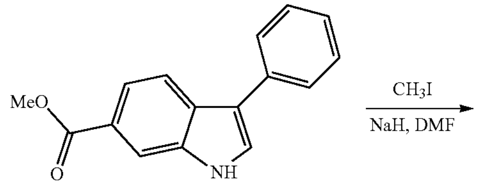

16b

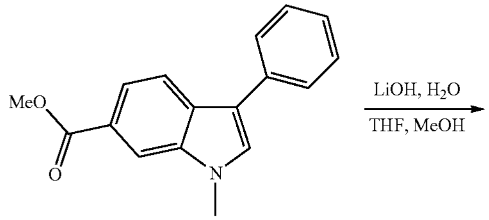

16c

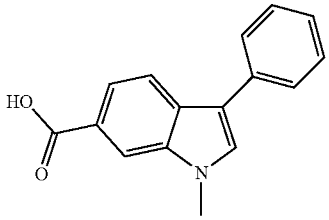

16d

A. 1-tert-Butyl 6-methyl 3-phenyl-1H-indole-1,6-dicarboxylate, 16a

A mixture of 1-tert-butyl 6-methyl 3-iodo-1H-indole-1,6-dicarboxylate 11a (5.02 mmol, 2.016 g), phenylboronic acid 10b (7.53 mmol, 0.92 g), $Pd(OAc)_2$ (0.402 mmol, 90 mg), Sphos 0.904 mmol, (0.37 g), and $K_3PO_4$ (10.1 mmol, 2.13 g) in toluene (10 mL) in sealed reaction vial was stirred at room temperature for 2 min and then heated at 90° C. under $N_2$ for 4 h. The reaction mixture was quenched with EtOAc and water. The organic layer was concentrated and purified by flash column chromatography (silica gel, 8% EtOAc/hexanes). The desired product was collected as a light yellow solid that was washed with small amount of hexanes to obtain 16a as a white solid.

B. Methyl 3-phenyl-1H-indole-6-carboxylate, 16b

To a solution of 1-tert-butyl 6-methyl 3-phenyl-1H-indole-1,6-dicarboxylate 16a (4.04 mmol, 1.42 g) in $CH_2Cl_2$ (8 mL) was added 6 mL of TFA. The resulting solution was stirred for 3 h. The mixture was then concentrated and washed with hexanes to afford 16b.

C. Methyl 1-methyl-3-phenyl-1H-indole-6-carboxylate, 16c

NaH (60% dispersion in mineral oil, 4.52 mmol, 186 mg) was added portion-wise to a solution of methyl 3-phenyl-1H-indole-6-carboxylate (2.07 mmol, 757 mg) in DMF at 0° C. and the mixture was stirred for 20 min. Methyl iodide (2.28 mmol, 0.14 mL) was added and the reaction mixture was maintained at 0° C. for 1 h. Water was then added and the reaction was extracted with EtOAc. The organics were concentrated and purified by flash column chromatography (silica gel, 15% EtOAc/hexanes) to give 16c.

D. 1-Methyl-3-phenyl-1H-indole-6-carboxylic acid, 16d

A mixture of compound 16c (517 mg, 1.95 mmol) and LiOH (187 mg, 7.80 mmol) in THF/MeOH/$H_2O$ (4/4/4 mL) was stirred for 4 h. A 15% citric acid solution (20 mL) was added, and the mixture was then extracted with EtOAc (3×). The combined extracts were washed with brine, dried over $Na_2SO_4$, filtered, and concentrated under reduced pressure. The residue, compound 16d, was dried under reduced pressure for 18 h.

Following the procedure described above for Example 16 and substituting the appropriate reagents, starting materials and purification methods known to those skilled in the art, the following intermediate compounds were prepared:

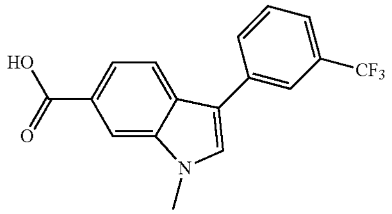

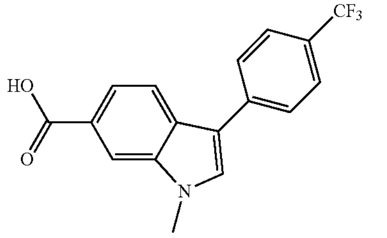

Example 17

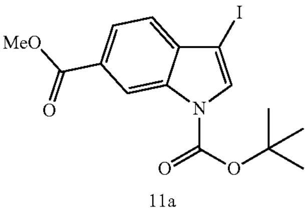

11a

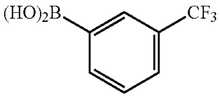

17a

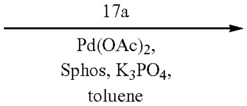

-continued

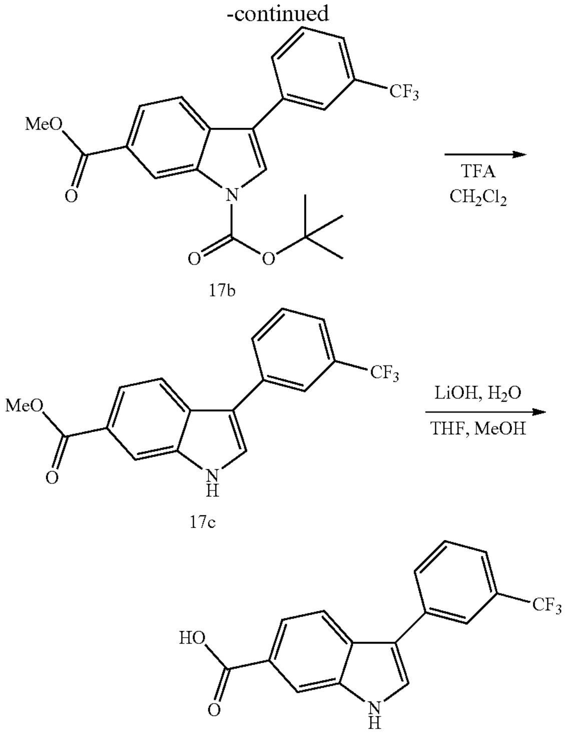

17b

17c

17d

A. 1-tert-Butyl 6-methyl 3-(3-(trifluoromethyl)phenyl)-1H-indole-1,6-dicarboxylate, 17b The title compound 17b was prepared using the method described in Example 16, substituting 17a for 10b in Step A.

B. Methyl 3-(3-(trifluoromethyl)phenyl)-1H-indole-6-carboxylate, 17c

The title compound 17c was prepared using the method described in Example 16, substituting 17b for 16a in Step B.

C. 3-(3-(Trifluoromethyl)phenyl)-1H-indole-6-carboxylic acid, 17d

The title compound was prepared using the method described in Example 16, substituting 17c for 16c in Step D.

Following the procedure described above for Example 17 and substituting the appropriate reagents, starting materials and purification methods known to those skilled in the art, the following intermediate compound was prepared:

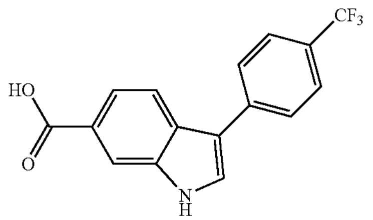 [SMILES: O=C(O)c1ccc2c(-c3ccc(C(F)(F)F)cc3)c[nH]c2c1]

Example 18

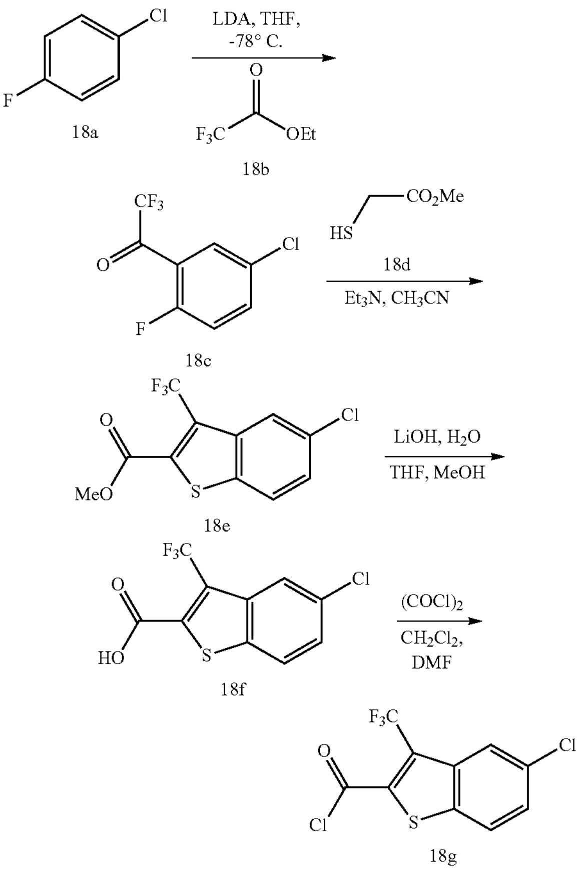

18a

18b

18c

18d

18e

18f

18g

A. 1-(5-Chloro-2-fluoro-phenyl)-2,2,2-trifluoro-ethanone, 18c

To a solution of LDA (2.0 M in THF/heptane/ethylbenzene, 25.3 mmol, 12.6 mL) in dry THF was slowly added 1-fluoro-4-chloro-benzene 18a (23.0 mmol, 2.45 mL) at −78° C. The mixture was stirred for 1 h at −78° C. and ethyl trifluoroacetate 18b (25.3 mmol, 3.02 mL) was added. The reaction mixture was allowed to warm to room temperature overnight and was quenched with saturated aqueous $NH_4Cl$ solution. The mixture was extracted with EtOAc. The organic extracts were concentrated and purified by flash column chromatography (silica gel, 15% EtOAc/hexanes) to give a mixture of the compound 18c along with a regio-isomeric by-product, 1-(5-fluoro-2-chloro-phenyl)-2,2,2-trifluoroethanone, in a ratio of 5:1 (18c is the major product).

B. Methyl 5-chloro-3-(trifluoromethyl)benzo[b]thiophene-2-carboxylate, 18e

A solution of compound 18c (6.62 mmol, 1.5 g), methyl 2-mercaptoacetate 18d (6.62 mmol, 0.6 mL), and $Et_3N$ (8.6 mmol, 1.2 mL) in acetonitrile (12 mL) was heated at 75° C. for 4 h. The reaction was diluted with EtOAc and water. The organic layer was concentrated and purified by flash column chromatography (silica gel, 10% EtOAc/hexanes) to provide the compound 18e.

C. 5-Chloro-3-trifluoromethyl-benzo[b]thiophene-2-carboxylic acid, 18f

A mixture of compound 18e (574 mg, 1.95 mmol) and LiOH (187 mg, 7.80 mmol) in THF/MeOH/$H_2O$ (4/4/4 mL) was stirred for 4 h. A 15% citric acid solution (20 mL) was added, and the mixture was then extracted with EtOAc (3×). The combined extracts were washed with brine, dried over $Na_2SO_4$, filtered, and concentrated under reduced pressure. The residue, compound 18f, was dried under reduced pressure for 18 h and was used without purification.

D. 5-Chloro-3-trifluoromethyl-benzo[b]thiophene-2-carbonyl chloride, 18g

To compound 18f in $CH_2Cl_2$ (5 mL) at room temperature was added $(COCl)_2$, followed by 2 drops of DMF. The reaction mixture was stirred at room temperature for 18 h. The reaction mixture was then concentrated to give compound 18g.

Example 19

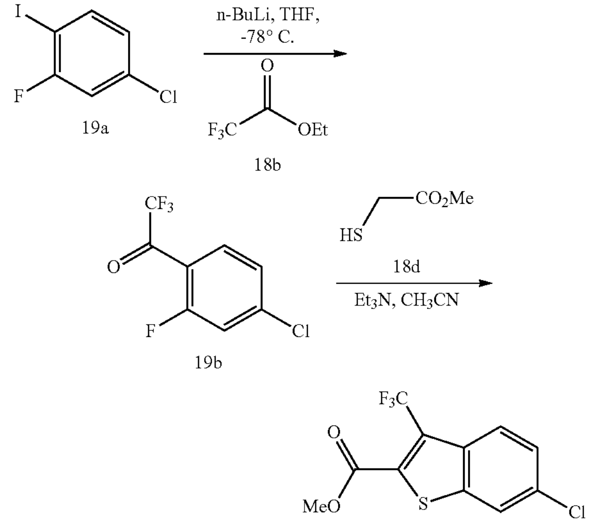

19a 18b 19b 18d 19c

A. 1-(4-Chloro-2-fluoro-phenyl)-2,2,2-trifluoro-ethanone, 19b

To a solution of n-BuLi (1.6 M in hexanes, 4.68 mmol, 2.93 mL) in dry THF was slowly added 4-chloro-2-fluoro-1-iodobenzene 19a (3.9 mmol, 1.0 g) at −78° C. under $N_2$. The mixture was stirred for 1 h at −78° C. and ethyl trifluoroacetate 18b (0.51 mL, 4.29 mmol) was added. The reaction was allowed to warm to room temperature overnight and was quenched with saturated aqueous $NH_4Cl$ solution. The mixture was extracted with EtOAc. The organic extracts were concentrated and purified by flash column chromatography (silica gel, 15% EtOAc/hexanes) to give compound 19b.

B. Methyl 6-chloro-3-(trifluoromethyl)benzo[b]thiophene-2-carboxylate, 19c

The title compound 19c was prepared using a similar method described in Example 18, substituting 19b for 18c in Step B.

Example 20

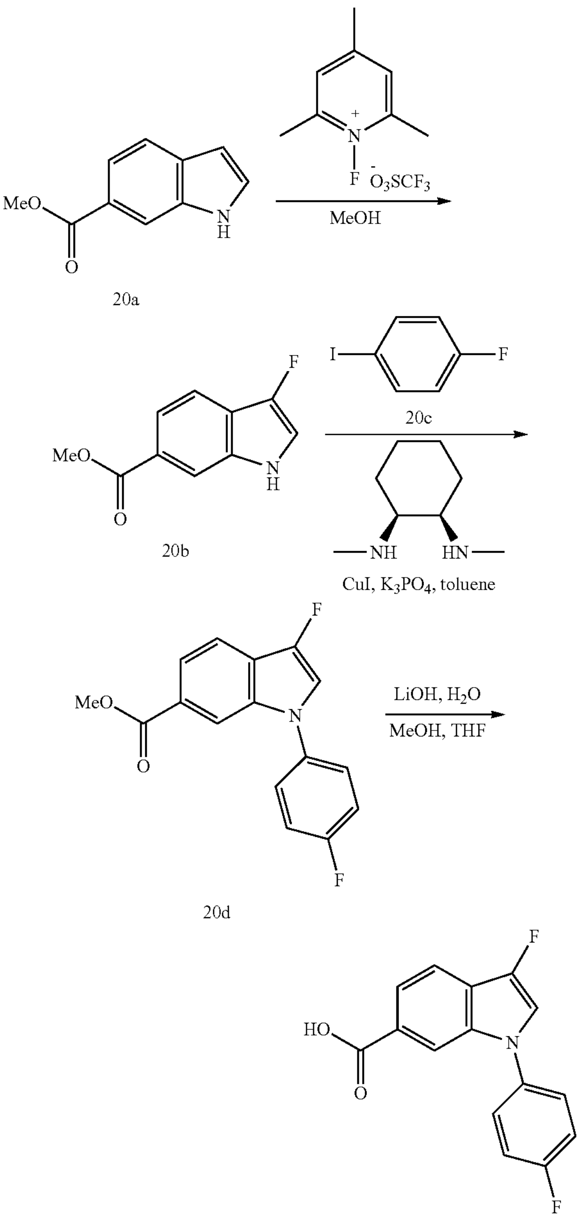

20a 20b 20c 20d 20e

A. Methyl 3-fluoro-1H-indole-6-carboxylate, 20b

A solution of methyl 1H-indole-6-carboxylate 20a (11.4 mmol, 2.0 g) and N-fluoro-2,4,6-trimethylpyridinium triflate (14.8 mmol, 4.3 g) in MeOH (100 mL) was heated at reflux for 18 h. The reaction mixture was concentrated and purified by flash column chromatography (silica gel, 15-20% EtOAc/hexanes) to give compound 20b as an off-white solid.

B. Methyl 3-fluoro-1-(4-fluorophenyl)-1H-indole-6-carboxylate, 20d

Compound 20b (0.264 mmol, 51 mg), CuI (0.0264 mmol, 5 mg) and $K_3PO_4$ (0.66 mmol, 40 mg) were combined in a sealed reaction tube and the vial was back-flushed with $N_2$. 4-fluoro-iodobenzene 20c (0.264 mmol, 0.0394 mL) and N,N'-dimethylcyclohexane-1,2-diamine (0.0792 mmol, 0.0125 mL) were added via syringe, followed by toluene. The reaction mixture was heated at 95° C. for 6 h. The reaction was diluted with EtOAc and water. The reaction mixture was concentrated and purified by flash column chromatography (silica gel, 20% EtOAc/hexanes) to give compound 20d.

C. 3-Fluoro-1-(4-fluorophenyl)-1H-indole-6-carboxylic acid, 20e

The title compound 20e was prepared using the method described in Example 18, Step C.

Example 21

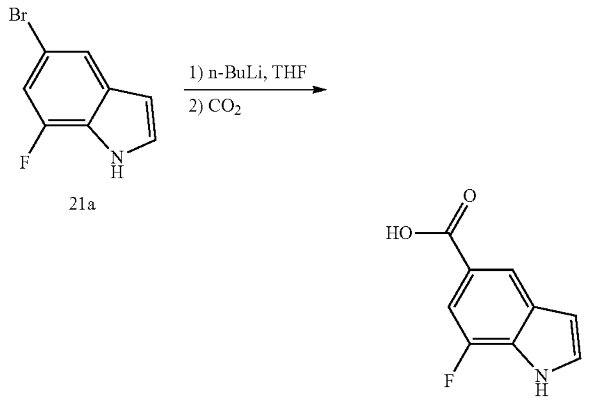

21a

21b

A. 7-Fluoro-1H-indole-5-carboxylic acid, 21b

To a solution of 5-bromo-7-fluoroindole 21a (1.71 mmol, 365 mg) in THF at −60° C. was added n-BuLi (1.6 M solution in hexanes, 5.2 mmol, 3.2 mL). The solution was kept at −60° C. for 4 h and was then poured onto an excess of freshly crushed dry ice. Water was added and the mixture was acidified to pH 4. The organic phase was concentrated and the residue was purified by flash column chromatography (silica gel, 35% EtOAc/hexanes) to give compound 21b.

Example 22

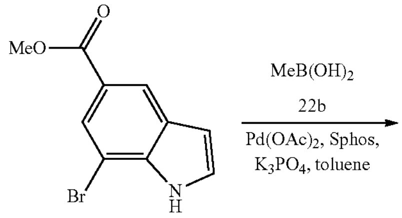

22a

-continued

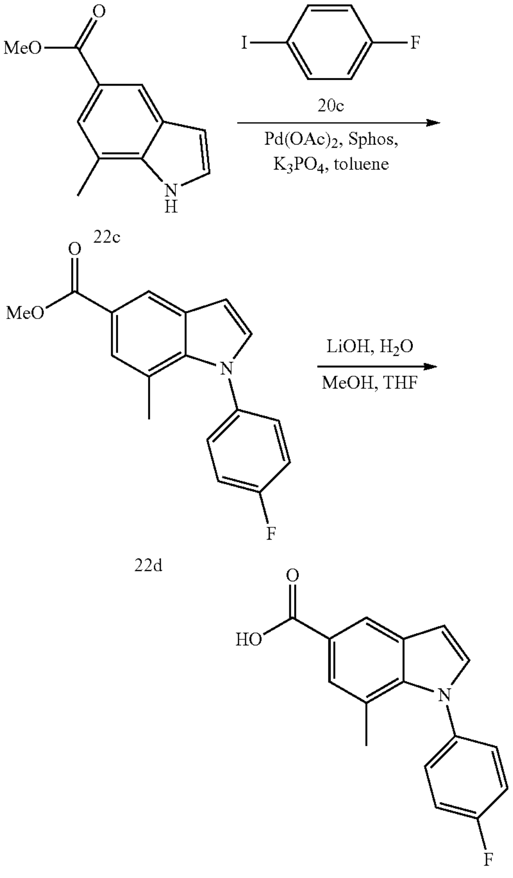

22c

22d

22e

A. Methyl 7-methyl-1H-indole-5-carboxylate, 22c

A mixture of compound 22a (0.613 mmol, 156 mg), methylboronic acid 22b (0.92 mmol, 79 mg), $Pd(OAc)_2$ (0.09 mmol, 20 mg), SPhos (0.215 mmol, 88 mg), and $K_3PO_4$ (1.23 mmol, 0.26 g) in toluene (2 mL) was heated to 100° C. for 3 h in a sealed reaction vessel. The reaction was diluted with EtOAc and water. The organic layer was concentrated and purified by flash column chromatography (silica gel, 10% EtOAc/hexanes) to give compound 22c.

B. Methyl 1-(4-fluorophenyl)-7-methyl-1H-indole-5-carboxylate, 22d

The title compound was prepared using the method described in Example 20, substituting 22c for 20b in Step B.

C. 1-(4-Fluorophenyl)-7-methyl-1H-indole-5-carboxylate, 22e

The title compound was prepared using the method described in Example 18, Step C.

Example 23

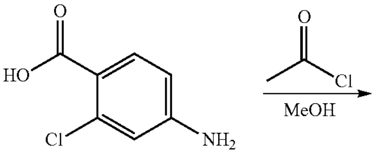

23a

-continued

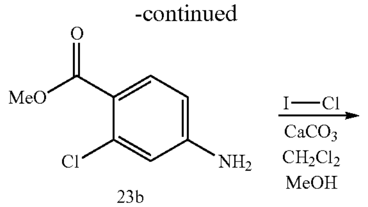

23b

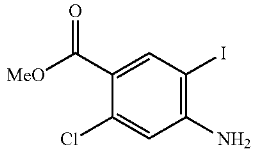

+

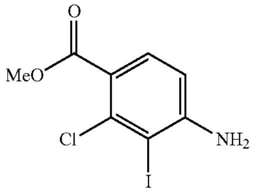

23c 23d

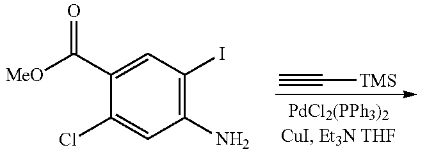

23c

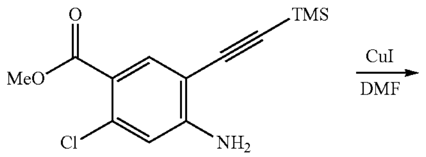

23e

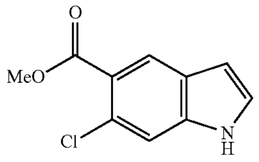

23f

A. Methyl 4-amino-2-chloro-benzoate, 23b

Acetyl chloride (35.2 mmol, 2.5 mL) was added dropwise to a stirring solution of 4-amino-2-chloro-benzoic acid 23a (12.9 mmol, 2.22 g) in methanol (50 mL). The mixture was heated at reflux for 18 h, cooled, and concentrated under vacuum. The residue was taken up in EtOAc, washed with saturated aqueous $NaHCO_3$ and brine, dried, and concentrated under vacuum. The crude product was purified by flash column chromatography (silica gel, 30% EtOAc/hexanes) to give compound 23b.

B. Methyl 4-amino-2-chloro-5-iodo-benzoate, 23c

To a suspension of compound 23b (1.18 g, 6.38 mmol) and $CaCO_3$ (12.8 mmol, 1.28 g) in MeOH (13 mL) was added a solution of iodine monochloride (6.70 mmol, 1.09 g) in $CH_2Cl_2$ (6 mL) dropwise at room temperature. The resulting reaction mixture was stirred at room temperature for 1.5 h. The reaction mixture was concentrated and then partitioned between EtOAc and water. The organic layer was concentrated and purified by flash column chromatography (silica gel, 20-25% EtOAc/hexanes) to provide methy 4-amino-2-chloro-5-iodo-benzoate 23c as the major the product and methy 4-amino-2-chloro-3-iodo-benzoate 23d as the minor product.

C. Methyl 4-amino-2-chloro-5-((trimethylsilyl)ethynyl)benzoate, 23e

To a mixture of compound 23c (0.642 mmol, 200 mg), CuI (0.064 mmol, 12.2 mg) and $Pd(PPh_3)_2Cl_2$ (0.064 mmol, 45 mg) in THF (2 mL) was added ethynyltrimethylsilane (0.963 mmol, 95 mg) followed by $Et_3N$ (7.19 mmol, 1 mL) under $N_2$. The reaction mixture was stirred at room temperature for 1.5 h and then partitioned between EtOAc and water. The organic layer was concentrated and purified by flash column chromatography (silica gel, 15% EtOAc/hexanes) to give compound 23e.

D. Methyl 6-chloro-1H-indole-5-carboxylate, 23f

A mixture of compound 23e (0.532 mmol, 150 mg) and CuI (0.32 mmol, 60 mg) in DMF (1.5 mL) was heated at 110° C. for 5 h and then cooled to room temperature. The reaction was quenched with water and extracted with EtOAc. The organic layer was concentrated and purified by flash column chromatography (silica gel, 15% EtOAc/hexanes) to give compound 23f.

Example 24

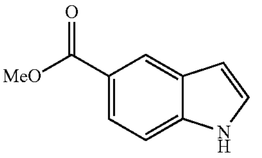

+

24a

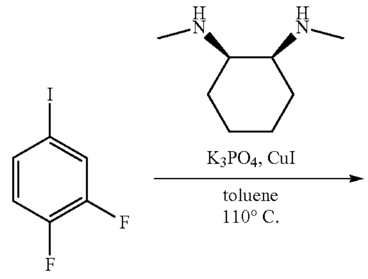

24b

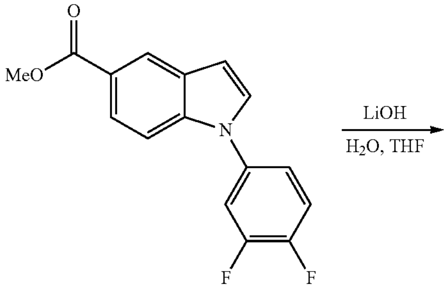

24c

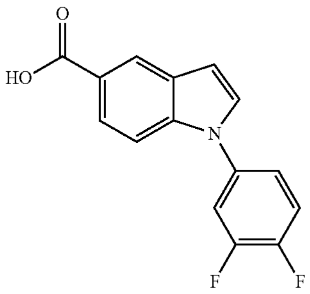

24d

A. Methyl 1-(3,4-difluorophenyl)-indole-5-carboxylate, 24c

A mixture of methyl indole-5-carboxylate 24a (2 g, 11.4 mmol), 1-iodo-3,4-difluoro-benzene 24b (1.5 mL, 12.5 mmol), CuI (0.22 g, 1.14 mmol), trans-N,N'-dimethylcyclo-hexane-1,2-diamine (0.54 mL, 3.43 mmol), and $K_3PO_4$ (6.06 g, 28.5 mmol) in toluene (12 mL) was heated at 110° C. for 7 hours. The reaction mixture was diluted with $CH_2Cl_2$ and filtered. The solution was concentrated and the residue was purified by flash column chromatography (silica gel, 20% EtOAc/heptane) to give 24c (3.0 g).

B. 1-(3,4-difluorophenyl)-indole-5-carboxylic acid, 24d

A mixture of methyl 1-(3,4-difluorophenyl)-indole-5-carboxylate 24c (3.0 g, 10.4 mmol) and LiOH (1.0 g, 41.8 mmol) in THF (120 mL) and $H_2O$ (60 mL) was stirred at room temperature for 5 days. Aqueous 10% HCl solution was added to the reaction mixture to adjust pH=3~4. The resulting mixture was extracted with EtOAc (2×). The organic solution was washed with aq. NaCl, dried over $Na_2SO_4$ and concentrated to give 24d (2.85 g).

Example 25

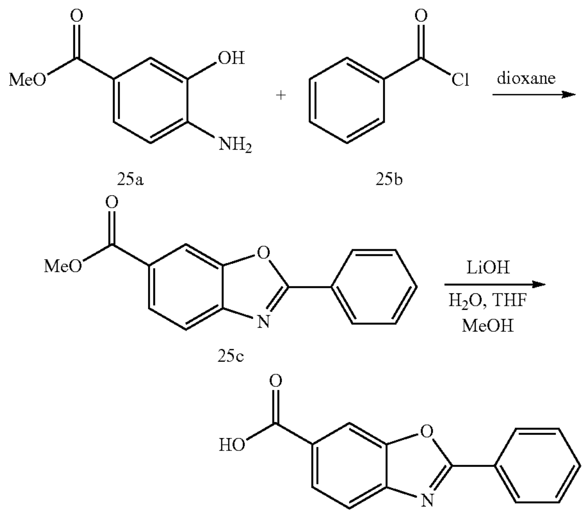

25a 25b 25c 25d

A. Methyl 2-phenyl-benzoxazole-6-carboxylate, 25c

A mixture of methyl 4-amino-3-hydroxy-benzoate 25a (0.3 g, 1.8 mmol) and benzoyl chloride 25b (0.23 mL, 2.0 mmol) in dioxane (2.5 mL) was heated at 210° C. under microwave for 15 min. The reaction mixture was diluted with $CH_2Cl_2$ and washed with aq. $NaHCO_3$. The organic solution was dried over $Na_2SO_4$, concentrated and purified by flash column chromatography (silica gel, 20% EtOAc/heptane) to give 25c (0.39 g).

B. 2-Phenyl-benzoxazole-6-carboxylic acid, 25d

A mixture of methyl 2-phenyl-benzoxazole-6-carboxylate 25c (0.37 g, 1.46 mmol) and LiOH (0.10 g, 4.2 mmol) in THF (4 mL), MeOH (4 mL), and $H_2O$ (4 mL) was stirred at room temperature for 6 h. Aqueous 1N HCl solution was added to the mixture to adjust pH to 3~4. The resulting mixture was extracted with EtOAc (2×). The organic solution was washed with aq. NaCl, dried over $Na_2SO_4$ and concentrated to give 25d (0.34 g).

Example 26

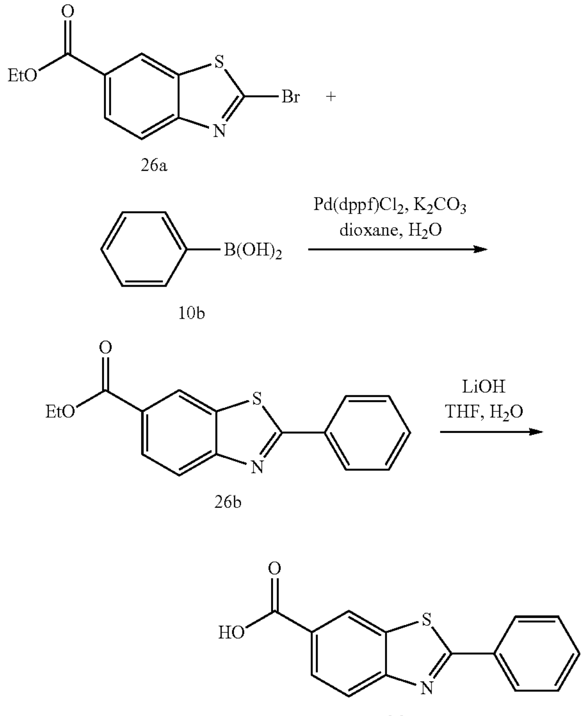

26a 10b 26b 26c

A. Ethyl 2-phenyl-benzothiazole-6-carboxylate, 26b

A mixture of ethyl 2-bromo-benzothiazole-6-carboxylate 26a (300 mg, 1.05 mmol), phenylboronic acid 10b (192 mg, 1.57 mmol), $K_2CO_3$ (188 mg, 1.36 mmol) and Pd(dppf) $Cl_2.CH_2Cl_2$ (43 mg, 0.05 mmol) in dioxane (2 mL) and $H_2O$ (0.4 ml) was heated at 120° C. for 25 min under microwave. The reaction mixture was diluted with $CH_2Cl_2$, washed with $H_2O$, dried over $Na_2SO_4$, and concentrated. Purification by flash column chromatography (silica gel, 15% EtOAc/heptane) gave 26b (220 mg).

B. 2-Phenyl-benzothiazole-6-carboxylic acid, 26c

Ethyl 2-phenyl-benzothiazole-6-carboxylate 26b (220 mg, 0.78 mmol) was stirred with LiOH (74 mg, 3.1 mmol) in THF (4 mL) and $H_2O$ (4 mL) for 16 h. Aqueous 1N HCl solution was added to the mixture to adjust pH to 3~4. The resulting mixture was extracted with EtOAc (2×). The organic solution was washed with aq. NaCl, dried over $Na_2SO_4$ and concentrated to give 26c (200 mg).

Example 27

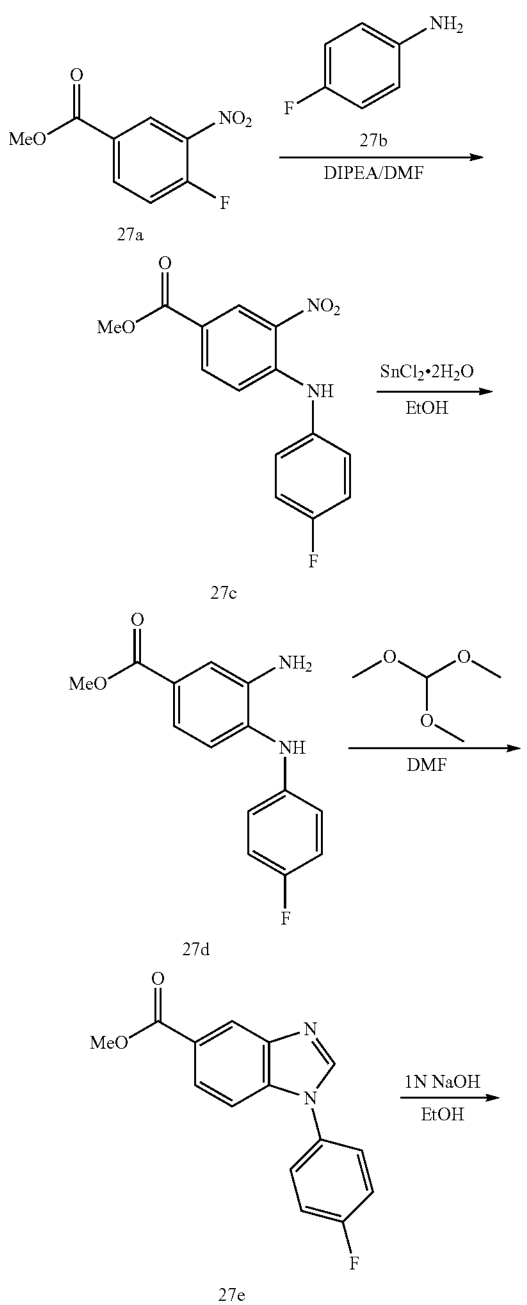

27a

27c

27d

27e

A. Methyl 4-((4-fluorophenyl)amino)-3-nitrobenzoate, 27c

A mixture of methyl 4-fluoro-3-nitrobenzoate 27a (1 g, 5.02 mmol), 4-fluoroaniline 27b (4.34 mL, 5.02 mmol), and DIPEA (1.04 mL, 6.03 mmol) in DMF (10 mL) was stirred at room temperature for 2 h. Water was added to the mixture; the resulting solid was filtered, washed with water, and dried. The crude product 27c was used in the next reaction without purification.

B. Methyl 3-amino-4-((4-fluorophenyl)amino)benzoate, 27d

A mixture of 27c (1.4 g, 4.8 mmol) and $SnCl_2.2H_2O$ (4.9 g, 21.7 mmol) in EtOH (50 mL) was stirred at 80° C. After 4 h, the mixture was cooled to room temperature and was slowly added to saturated aqueous $NaHCO_3$. The solid was filtered and washed with $H_2O$. The solid was triturated with EtOAc and the filtrate was concentrated. The crude product 27d was used in the next reaction without purification. MS m/z $(M+H^+)$ 261.1.

C. Methyl 1-(4-fluorophenyl)-1H-benzimidazole-5-carboxylate, 27e

A mixture of 27d (0.18 g, 0.693 mmol) and trimethyl orthoformate (0.7 mL, 6.39 mmol) in DMF (2 mL) was refluxed for 5 h and then cooled to room temperature. Water was added to the mixture. The resulting solid was filtered, washed, with water, and dried. The crude product 27e was used in the next reaction without purification. MS m/z $(M+H^+)$ 271.1.

D. 1-(4-Fluorophenyl)-1H-benzo[d]imidazole-5-carboxylic acid, 27f

To a solution of 27e (0.18 g, 0.666 mmol) in EtOH (10 mL) was added 1N aqueous NaOH (2.5 mL, 2.5 mmol). The mixture was stirred at room temperature for 4 d. The solvent was evaporated and 1N aqueous HCl was added, followed by extraction with EtOAc. The organic layer was dried over $MgSO_4$ and concentrated. The crude product 27f was purified by preparative reverse phase chromatography. MS m/z $(M+H^+)$ 257.1.

Following the procedure described above for Example 27 and substituting the appropriate reagents, starting materials and purification methods known to those skilled in the art, the following intermediate compounds were prepared.

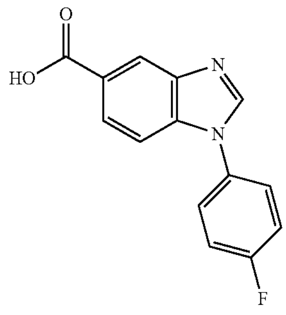

27f

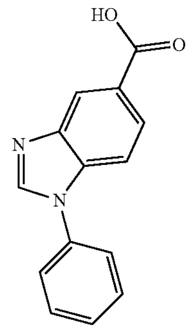

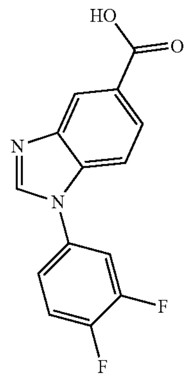

-continued

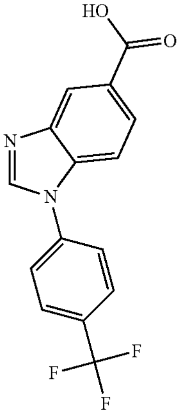

Example 28

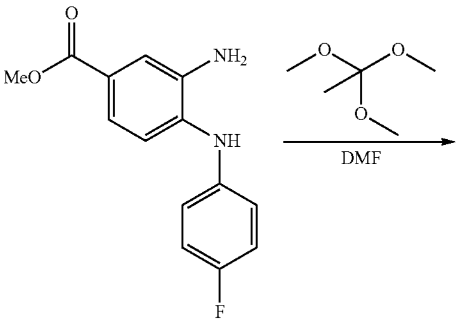

27d

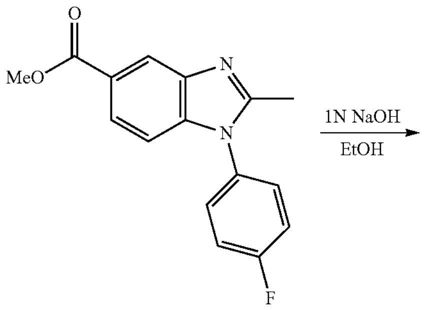

28a

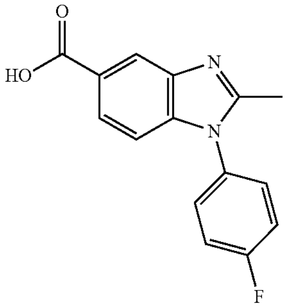

28b

A. Methyl 2-methyl-1-(4-fluorophenyl)-1H-benzimidazole-5-carboxylate, 28a

The title compound 28a was prepared using the method described in Example 27, substituting trimethyl orthoacetate for trimethyl orthoformate in Step C. The crude product 28a was used in the next reaction without purification. MS m/z $(M+H^+)$ 285.1.

B. 2-Methyl-1-(4-fluorophenyl)-1H-benzimidazole-5-carboxylate, 28b

The title compound 28b was prepared using the method described in Example 28, substituting 28a for 27e in Step D. MS m/z $(M+H^+)$ 271.2.

Following the procedure described above for Example 28 and substituting the appropriate reagents, starting materials and purification methods known to those skilled in the art, the following intermediate compounds were prepared.

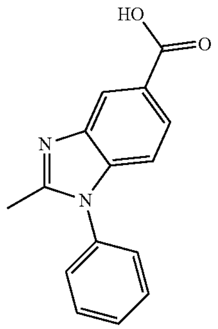

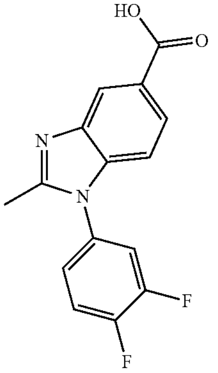

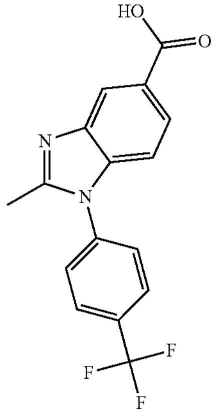

The schemes and examples described herein were used to prepare compounds of Formula (Ia)

Formula (Ia)

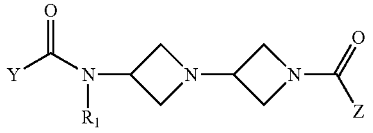

selected from the group consisting of a compound wherein Y is thiazol-2-yl, $R_1$ is H, and Z is 1-(4-trifluoromethylphenyl)-1H-indol-5-yl;

a compound wherein Y is thiazol-4-yl, $R_1$ is H, and Z is 4-(3-trifluoromethylphenyl)phenyl;

a compound wherein Y is thiazol-2-yl, $R_1$ is H, and Z is 1-(phenylsulfonyl)-1H-indol-5-yl;

a compound wherein Y is thiazol-2-yl, $R_1$ is H, and Z is 2-phenyl-benzothiazol-6-yl;

a compound wherein Y is thiazol-2-yl, $R_1$ is H, and Z is 4-(3-trifluoromethylphenyl)phenyl;

a compound wherein Y is thiazol-2-yl, $R_1$ is H, and Z is 6-phenyl-benzothiophen-2-yl;

a compound wherein Y is thiazol-2-yl, $R_1$ is H, and Z is 6-trifluoromethyl-benzothiophen-2-yl;

a compound wherein Y is thiazol-2-yl, $R_1$ is H, and Z is 4-trifluoromethyl-benzothiophen-2-yl;

a compound wherein Y is thiazol-2-yl, $R_1$ is H, and Z is 4-(5-trifluoromethyl-thien-2-yl)-phenyl;

a compound wherein Y is thiazol-2-yl, $R_1$ is H, and Z is 4-(phenylmethyl)-phenyl;

a compound wherein Y is thiazol-4-yl, $R_1$ is H, and Z is 1-(4-fluorophenyl)-1H-indol-5-yl;

a compound wherein Y is thiazol-2-yl, $R_1$ is H, and Z is 4-(4-trifluoromethylphenyl)-phenyl;

a compound wherein Y is thiazol-2-yl, $R_1$ is H, and Z is 1-phenyl-1H-indol-5-yl;

a compound wherein Y is thiazol-4-yl, $R_1$ is H, and Z is 4-(4-trifluoromethylphenyl)-phenyl;

a compound wherein Y is thiazol-2-yl, $R_1$ is H, and Z is 3-methyl-5-chloro-benzothiophen-2-yl;

a compound wherein Y is thiazol-2-yl, $R_1$ is H, and Z is 4-(4-trifluoromethylphenylmethyl)-phenyl;

a compound wherein Y is thiazol-2-yl, $R_1$ is H, and Z is 2-phenyl-benzoxazol-6-yl;

a compound wherein Y is thiazol-2-yl, $R_1$ is H, and Z is 4-(3-methanesulfonylphenyl) phenyl;

a compound wherein Y is thiazol-2-yl, $R_1$ is H, and Z is 5-bromo-naphth-2-yl;

a compound wherein Y is thiazol-2-yl, $R_1$ is H, and Z is 4-(3-trifluoromethylphenylmethyl)-phenyl;

a compound wherein Y is thiazol-2-yl, $R_1$ is H, and Z is 6-phenyl-naphth-2-yl;

a compound wherein Y is thiazol-4-yl, $R_1$ is H, and Z is 2-phenyl-benzothiazol-6-yl;

a compound wherein Y is thiazol-2-yl, $R_1$ is H, and Z is 6-bromo-benzothiophen-2-yl;

a compound wherein Y is phenyl, $R_1$ is H, and Z is 5-bromo-naphth-2-yl;

a compound wherein Y is phenyl, $R_1$ is H, and Z is 5-phenyl-naphth-2-yl;

a compound wherein Y is phenyl, $R_1$ is H, and Z is 4-(4-trifluoromethyl phenylmethyl)-phenyl;

a compound wherein Y is thiazol-2-yl, $R_1$ is H, and Z is 1-phenyl-1H-indol-6-yl;

a compound wherein Y is thiazol-2-yl, $R_1$ is H, and Z is 2-(3-trifluoromethylphenyl)-benzoxazol-6-yl;

a compound wherein Y is thiazol-2-yl, $R_1$ is H, and Z is 4-phenyl-phenyl;

a compound wherein Y is thiazol-2-yl, $R_1$ is H, and Z is 2-(4-trifluoromethylphenyl)-benzoxazol-6-yl;

a compound wherein Y is phenyl, $R_1$ is H, and Z is 4-(phenylmethyl)-phenyl;

a compound wherein Y is thiazol-2-yl, $R_1$ is H, and Z is 4-phenoxy-phenyl;

a compound wherein Y is thiazol-2-yl, $R_1$ is H, and Z is 2-(4-chlorophenyl)-benzoxazol-6-yl;

a compound wherein Y is phenyl, $R_1$ is H, and Z is 6-phenyl-naphth-2-yl;

a compound wherein Y is thiazol-2-yl, $R_1$ is H, and Z is 2-phenyl-benzoxazol-5-yl;

a compound wherein Y is phenyl, $R_1$ is H, and Z is 3-methyl-5-chloro-benzothiophen-2-yl;

a compound wherein Y is thiazol-2-yl, $R_1$ is methyl, and Z is 6-trifluoromethyl-benzothiophen-2-yl;

a compound wherein Y is thiazol-2-yl, $R_1$ is H, and Z is 4-(phenylcarbonyl)-phenyl;

a compound wherein Y is phenyl, $R_1$ is H, and Z is 4-phenyl-phenyl;

a compound wherein Y is thiazol-2-yl, $R_1$ is H, and Z is 6-bromo-naphth-2-yl;

a compound wherein Y is phenyl, $R_1$ is H, and Z is 2-phenyl-benzoxazol-6-yl;

a compound wherein Y is phenyl, $R_1$ is H, and Z is 6-bromo-naphth-2-yl;

a compound wherein Y is thiazol-2-yl, $R_1$ is H, and Z is 4-bromophenyl;

a compound wherein Y is phenyl, $R_1$ is H, and Z is 5-trifluoromethyl-benzothiophen-2-yl;

a compound wherein Y is phenyl, $R_1$ is H, and Z is 4-phenoxy-phenyl;

a compound wherein Y is thiazol-4-yl, $R_1$ is H, and Z is 2-bromo-benzothiazol-6-yl;

a compound wherein Y is thiazol-2-yl, $R_1$ is H, and Z is 5-trifluoromethyl-benzothiazol-2-yl;

a compound wherein Y is thiazol-4-yl, $R_1$ is methyl, and Z is 6-trifluoromethyl-benzothiophen-2-yl;

a compound wherein Y is thiazol-4-yl, $R_1$ is H, and Z is 6-trifluoromethyl-benzothiophen-2-yl;

a compound wherein Y is thiazol-2-yl, $R_1$ is H, and Z is 3-chloro-6-trifluoromethyl-benzothiophen-2-yl;

a compound wherein Y is thiazol-4-yl, $R_1$ is H, and Z is 3-chloro-6-trifluoromethyl-benzothiophen-2-yl;

a compound wherein Y is thiazol-2-yl, $R_1$ is H, and Z is 1-phenyl-1H-indazol-5-yl;

a compound wherein Y is thiazol-2-yl, $R_1$ is H, and Z is 5-phenyl-naphth-2-yl;

a compound wherein Y is thiazol-4-yl, $R_1$ is H, and Z is 1-(3,4-difluorophenyl)-1H-indol-5-yl;

a compound wherein Y is thiazol-2-yl, $R_1$ is H, and Z is 1-(2,4-difluorophenyl)-1H-indol-5-yl;

a compound wherein Y is thiazol-2-yl, $R_1$ is H, and Z is 3-methyl-6-trifluoromethyl-benzothiophen-2-yl;

a compound wherein Y is thiazol-2-yl, $R_1$ is H, and Z is 1-(3,4-difluorophenyl)-1H-indol-5-yl;

a compound wherein Y is thiazol-2-yl, $R_1$ is H, and Z is 2-methyl-4-(3-trifluoromethylphenyl)-phenyl;

a compound wherein Y is thiazol-2-yl, $R_1$ is H, and Z is 2-fluoro-4-(4-trifluoromethylphenyl)-phenyl;

a compound wherein Y is thiazol-4-yl, $R_1$ is H, and Z is 1-(2,4-difluorophenyl)-1H-indol-5-yl;

a compound wherein Y is thiazol-2-yl, $R_1$ is H, and Z is 1-(4-fluorophenyl)-1H-indol-5-yl;

a compound wherein Y is thiazol-2-yl, $R_1$ is H, and Z is 1-(4-fluorophenyl)-3-methyl-1H-indol-5-yl;

a compound wherein Y is thiazol-2-yl, $R_1$ is H, and Z is 2-methyl-4-(4-trifluoromethylphenyl)phenyl;

a compound wherein Y is thiazol-2-yl, $R_1$ is H, and Z is 2-fluoro-4-(3-trifluoromethylphenyl)-phenyl;

a compound wherein Y is thiazol-2-yl, $R_1$ is H, and Z is 3-methyl-6-bromo-benzothiophen-2-yl;

a compound wherein Y is thiazol-2-yl, $R_1$ is H, and Z is 3-methyl-6-phenyl-benzothiophen-2-yl; and a compound wherein Y is thiazol-4-yl, $R_1$ is H, and Z is 3-methyl-6-trifluoromethyl-benzothiophen-2-yl;

and pharmaceutically acceptable salt forms thereof.

The schemes and examples described herein were used to prepare compounds of Formula (Ib)

Formula (Ib)

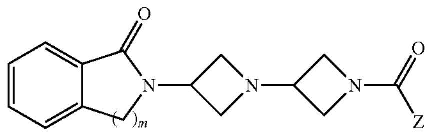

selected from the group consisting of a compound wherein m is 1, and Z is 3-chloro-6-phenyl-benzothiophen-2-yl;

a compound wherein m is 1, and Z is 6-phenyl-naphth-2-yl;

a compound wherein m is 1, and Z is 1-(4-trifluoromethylphenyl)-1H-indol-5-yl;

a compound wherein m is 1, and Z is 1-(phenylsulfonyl)-1H-indol-5-yl;

a compound wherein m is 1, and Z is 6-(3-methanesulfonylphenyl)-benzothiophen-2-yl;

a compound wherein m is 1, and Z is 3-chloro-6-bromo-benzothiophen-2-yl;

a compound wherein m is 1, and Z is 3,6-diphenyl-benzothiophen-2-yl;

a compound wherein m is 1, and Z is 1-(3-trifluoromethylphenyl)-1H-indol-5-yl;

a compound wherein m is 1, and Z is 4-(5-trifluoromethyl-thien-2-yl)-phenyl;

a compound wherein m is 1, and Z is 2-phenyl-benzoxazol-5-yl;

a compound wherein m is 1, and Z is 2-(3-trifluoromethylphenyl)-benzoxazol-6-yl;

a compound wherein m is 1, and Z is 5-phenyl-benzothiophen-2-yl;

a compound wherein m is 1, and Z is 4-(3-methanesulfonylphenyl)phenyl;

a compound wherein m is 1, and Z is 6-trifluoromethyl-benzothiophen-2-yl;

a compound wherein m is 1, and Z is 5-(3-methanesulfonylphenyl)benzothiophen-2-yl;

a compound wherein m is 1, and Z is 5-bromo-naphth-2-yl;

a compound wherein m is 1, and Z is 2-phenyl-benzoxazol-6-yl;

a compound wherein m is 1, and Z is 1-phenyl-1H-indol-5-yl;

a compound wherein m is 1, and Z is 4-(3-trifluoromethylphenylmethyl)phenyl;

a compound wherein m is 1, and Z is 6-bromo-benzothiophen-2-yl;

a compound wherein m is 1, and Z is 2-(4-chlorophenyl)-benzoxazol-6-yl;

a compound wherein m is 1, and Z is 1-(2-trifluoromethylphenyl)-1H-indol-5-yl;

a compound wherein m is 1, and Z is 6-bromo-naphth-2-yl;

a compound wherein m is 1, and Z is 4-piperadin-1-yl-phenyl;

a compound wherein m is 1, and Z is 4-phenyl-phenyl;

a compound wherein m is 1, and Z is 5-bromo-benzothiophen-2-yl;

a compound wherein m is 1, and Z is 4-(phenylmethyl)phenyl;

a compound wherein m is 1, and Z is 4-(benzothiophen-2-yl) phenyl a compound wherein m is 1, and Z is 4-bromophenyl;

a compound wherein m is 1, and Z is 5-phenyl-naphth-2-yl;

a compound wherein m is 1, and Z is 6-phenyl-benzothiophen-2-yl;

a compound wherein m is 1, and Z is 3-chloro-6-trifluoromethyl-benzothiophen-2-yl;

a compound wherein m is 1, and Z is 3-chloro-6-fluoro-benzothiophen-2-yl;

a compound wherein m is 1, and Z is 3-methyl-6-trifluoromethyl-benzothiophen-2-yl; and a compound wherein m is 1, and Z is 1-(4-fluorophenyl)-1H-indol-5-yl;

and pharmaceutically acceptable salt forms thereof.

The schemes and examples described herein were used to prepare compounds of Formula (Ic)

Formula (Ic)

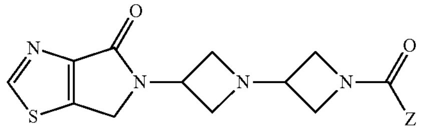

selected from the group consisting of a compound wherein Z is 3-methyl-6-trifluoromethyl-benzothiophen-2-yl;

a compound wherein Z is 2-methyl-4-(3-trifluoromethylphenyl)phenyl;

a compound wherein Z is 2-methyl-4-(4-trifluoromethylphenyl)phenyl; and a compound wherein Z is 1-(4-trifluoromethylphenyl)-1H-indol-5-yl;

and pharmaceutically acceptable salt forms thereof.

BIOLOGICAL EXAMPLES

In Vitro Methods

Example 1

MGL Enzyme Activity Assay

All rate-based assays were performed in black 384-well polypropylene PCR microplates (Abgene) in a total volume of 30 μL. Substrate 4-methylumbelliferyl butyrate (4MU-B; Sigma) and either purified mutant MGL (mut-MGLL 11-313 L179S L186S) or purified wild type MGL (wt-MGLL 6H-11-313) were diluted separately into 20 mM PIPES buffer (pH=7.0), containing 150 mM NaCl and 0.001% Tween 20. Compounds of Formula (I), including Formulas I(a), I(b), and I(c), were pre-dispensed (50 nL) into the assay plate using a Cartesian Hummingbird prior to adding 4MU-B (25 μL of 1.2× solution to a final concentration of 10 μM) followed by enzyme (5 μL of a 6× solution to a final concentration of 5 nM) to initiate the reaction. Final compound concentrations ranged from 17 to 0.0003 μM. The fluorescence change due to 4MU-B cleavage was monitored with excitation and emission wavelengths of 335 and 440 nm, respectively, and a bandwidth of 10 nm (Safire$^2$, Tecan) at 37° C. for 5 min.

The $IC_{50}$ values for the following compounds were determined using Microsoft Office Excel from a fit of the equation to the concentration-response plot of the fractional activity as a function of inhibitor concentration.

BIOLOGICAL DATA TABLE 1

| Cpd | MGL mutant inh $IC_{50}$ (μM) | MGL wild type inh $IC_{50}$ (μM) |
|---|---|---|
| 1 | 0.005 | <0.005 |
| 2 | 0.006 | 0.008 |
| 3 | 0.006 | |
| 4 | 0.007 | 0.013 |
| 5 | 0.007 | 0.015 |
| 6 | 0.008 | |
| 7 | 0.010 | <0.005 |
| 8 | 0.012 | |
| 9 | 0.013 | 0.506 |
| 10 | 0.015 | 0.070 |
| 11 | 0.015 | |
| 12 | 0.018 | <0.005 |
| 13 | 0.019 | <0.005 |
| 14 | 0.027 | 0.009 |
| 15 | 0.028 | |
| 16 | 0.032 | <0.005 |
| 17 | 0.048 | 0.037 |
| 18 | 0.059 | |
| 19 | 0.063 | |
| 20 | 0.065 | |
| 21 | 0.069 | |
| 22 | 0.086 | |
| 23 | 0.093 | |
| 24 | 0.099 | |
| 25 | 0.154 | |
| 26 | 0.157 | |
| 27 | 0.167 | |
| 28 | 0.180 | |
| 29 | 0.184 | |
| 30 | 0.264 | |
| 31 | 0.270 | |
| 32 | 0.287 | |
| 33 | 0.303 | |
| 34 | 0.332 | |
| 35 | 0.341 | |
| 36 | 0.458 | |
| 37 | 0.476 | |
| 38 | 0.588 | |
| 39 | 0.604 | |
| 40 | 0.882 | |
| 41 | 0.939 | |
| 42 | 0.997 | |
| 43 | 1.684 | |
| 44 | 1.831 | |
| 45 | 2.775 | |
| 46 | 3.754 | |
| 47 | 4.750 | |
| 48 | 8.125 | 12.888 |
| 49 | <0.005 | 0.014 |
| 50 | <0.005 | <0.005 |
| 51 | <0.005 | <0.005 |
| 52 | <0.005 | <0.005 |
| 53 | <0.005 | |
| 54 | | 0.005 |
| 55 | | 0.005 |
| 56 | | 0.006 |
| 57 | | 0.007 |
| 58 | | 0.008 |
| 59 | | 0.010 |
| 60 | | 0.011 |
| 61 | | 0.012 |
| 62 | | 0.015 |
| 63 | | 0.029 |
| 64 | | <0.005 |
| 65 | | <0.005 |
| 66 | | <0.005 |
| 67 | | <0.005 |
| 68 | 0.006 | <0.005 |
| 69 | 0.008 | <0.005 |
| 70 | 0.008 | <0.005 |
| 71 | 0.008 | |
| 72 | 0.009 | <0.005 |
| 73 | 0.012 | <0.005 |
| 74 | 0.012 | <0.005 |
| 75 | 0.015 | |
| 76 | 0.015 | <0.005 |
| 77 | 0.016 | 0.031 |

BIOLOGICAL DATA TABLE 1-continued

| Cpd | MGL mutant inh $IC_{50}$ (μM) | MGL wild type inh $IC_{50}$ (μM) |
|---|---|---|
| 78 | 0.017 | |
| 79 | 0.018 | 0.010 |
| 80 | 0.019 | |
| 81 | 0.019 | |
| 82 | 0.022 | 0.016 |
| 83 | 0.023 | |
| 84 | 0.031 | |
| 85 | 0.036 | |
| 86 | 0.050 | |
| 87 | 0.050 | |
| 88 | 0.096 | |
| 89 | 0.098 | |
| 90 | 0.154 | |
| 91 | 0.236 | |
| 92 | 0.242 | |
| 93 | 0.360 | |
| 94 | 0.412 | |
| 95 | 0.750 | |
| 96 | 4.674 | |
| 97 | <0.005 | <0.005 |
| 98 | <0.005 | <0.005 |
| 99 | <0.005 | <0.005 |
| 100 | <0.005 | |
| 101 | | 0.006 |
| 102 | | 0.011 |
| 103 | | 0.021 |
| 104 | | 0.066 |
| 105 | | 0.887 |
| 106 | | <0.005 |

Example 2

2-AG Accumulation Assay

To measure the accumulation of 2-AG due to inhibition of MGL, one g rat brain was homogenized using a Polytron homogenizer (Brinkmann, PT300) in 10 mL of 20 mM HEPES buffer (pH=7.4), containing 125 mM NaCl, 1 mM EDTA, 5 mM KCl and 20 mM glucose. Compounds of Formula (I) (10 μM) were pre-incubated with rat brain homogenate (50 mg). After a 15-min incubation time at 37° C., $CaCl_2$ (final concentration=10 mM) was added and then incubated for 15 min at 37° C. in a total volume of 5 mL. The reactions were stopped with 6 mL organic solvent extraction solution of 2:1 chloroform/methanol. Accumulated 2-AG in the organic phase was measured by a HPLC/MS method, according to the following equation:

$$\text{percent vehicle}=(2\text{-}AG \text{ accumulation in the presence of compound}/2\text{-}AG \text{ accumulation in vehicle})\times 100.$$

BIOLOGICAL DATA TABLE 2

| Cpd No | Rat Brain 2AG % VehCntrl (%) @0.01 mM | Rat Brain 2AG % VehCntrl (%) @0.1 mM | Rat Brain 2AG % VehCntrl (%) @1 mM | Rat Brain 2AG % VehCntrl (%) @10 mM |
|---|---|---|---|---|
| 1 | | 168 | 370 | 639 |
| 2 | | | 620 | |
| 3 | | | 271 | |
| 4 | | | 148 | |
| 5 | | 147 | 347 | 921 |
| 7 | | | 243 | |
| 8 | | | 127 | |
| 9 | | | 193 | 160 |
| 10 | | | | 659 |
| 11 | | | | 220 |
| 12 | | | 215 | 557 |

BIOLOGICAL DATA TABLE 2-continued

| Cpd No | Rat Brain 2AG % VehCntrl (%) @0.01 mM | Rat Brain 2AG % VehCntrl (%) @0.1 mM | Rat Brain 2AG % VehCntrl (%) @1 mM | Rat Brain 2AG % VehCntrl (%) @10 mM |
|---|---|---|---|---|
| 13 | | | 441 | |
| 14 | | | 187 | |
| 15 | | | | 611 |
| 16 | | | | 123 |
| 17 | | 282 | 355 | 486 |
| 18 | | | 218 | |
| 19 | | | | 418 |
| 20 | | | | 977 |
| 21 | | | | 581 |
| 23 | | | | 343 |
| 24 | | | | 73 |
| 49 | | | 167 | |
| 50 | | | 460 | |
| 51 | | | 477 | |
| 52 | | | 291 | |
| 53 | | | | 722 |
| 54 | | | 315 | |
| 55 | | | 353 | |
| 56 | | | 413 | |
| 57 | | | 424 | |
| 58 | | | 157 | |
| 59 | | | 265 | |
| 60 | | | 273 | |
| 61 | | | 338 | |
| 62 | | | 334 | |
| 63 | | | 185 | |
| 64 | | | 253 | |
| 65 | | | 324 | |
| 66 | | | 399 | |
| 67 | | | 434 | |
| 68 | | | 433 | |
| 69 | | | | 600 |
| 70 | 104 | 165 | 483 | 736 |
| 71 | | | | 400 |
| 72 | | | 781 | |
| 73 | | | 295 | |
| 74 | | | 323 | |
| 75 | | | | 1160 |
| 76 | | 112 | 204 | 725 |
| 77 | | | | 478 |
| 78 | | | | 1140 |
| 79 | | 144 | 253 | 676 |
| 80 | | | 166 | |
| 81 | | | 192 | 409 |
| 82 | | | 490 | |
| 83 | | | | 416 |
| 84 | | | 152 | 435 |
| 85 | | | | 693 |
| 86 | | | | 447 |
| 87 | | | | 250 |
| 88 | | | | 294 |
| 89 | | | | 663 |
| 97 | | | | 518 |
| 98 | | | | 613 |
| 99 | | | 449 | |
| 100 | | | 208 | |
| 101 | | | 534 | |
| 102 | | | 332 | |
| 103 | | | 360 | |
| 106 | | | 414 | |

Example 3

MGL ThermoFluor° Assay

Mutant

The ThermoFluor (TF) assay is a 384-well plate-based binding assay that measures thermal stability of proteins[1,2]. The experiments were carried out using instruments available from Johnson & Johnson Pharmaceutical Research & Development, LLC. TF dye used in all experiments was 1,8-ANS (Invitrogen: A-47). Final TF assay conditions used for MGL studies were 0.07 mg/ml of mutant MGL, 100 μM ANS, 200 mM NaCl, 0.001% Tween-20 in 50 mM PIPES (pH=7.0).

Screening compound plates contained 100% DMSO compound solutions at a single concentration. For follow-up concentration-response studies, compounds were arranged in a pre-dispensed plate (Greiner Bio-one: 781280), wherein compounds were serially diluted in 100% DMSO across 11 columns within a series. Columns 12 and 24 were used as DMSO reference and contained no compound. For both single and multiple compound concentration-response experiments, the compound aliquots (46 nL) were robotically predispensed directly into 384-well black assay plates (Abgene: TF-0384/k) using the Hummingbird liquid handler. Following compound dispension, protein and dye solutions were added to achieve the final assay volume of 3 μL. The assay solutions were overlayed with 1 μL of silicone oil (Fluka, type DC 200: 85411) to prevent evaporation.

Bar-coded assay plates were robotically loaded onto a thermostatically controlled PCR-type thermal block and then heated from 40 to 90° C. degrees at a ramp-rate of 1° C./min for all experiments. Fluorescence was measured by continuous illumination with UV light (Hamamatsu LC6), supplied via fiber optics and filtered through a band-pass filter (380-400 nm; >60D cutoff). Fluorescence emission of the entire 384-well plate was detected by measuring light intensity using a CCD camera (Sensys, Roper Scientific) filtered to detect 500±25 nm, resulting in simultaneous and independent readings of all 384 wells. A single image with 20-sec exposure time was collected at each temperature, and the sum of the pixel intensity in a given area of the assay plate was recorded vs temperature and fit to standard equations to yield the $T_m$[1].

1. Pantoliano, M. W., Petrella, E. C., Kwasnoski, J. D., Lobanov, V. S., Myslik, J., Graf, E., Carver, T., Asel, E., Springer, B. A., Lane, P., and Salemme, F. R. (2001) *J Biomol Screen* 6, 429-40.
2. Matulis, D., Kranz, J. K., Salemme, F. R., and Todd, M. J. (2005) *Biochemistry* 44, 5258-66.

The $K_d$ values for certain compounds of Formula (I) were determined from a fit of the equation to the concentration-response plot of the fractional activity as a function of $L_m$. For some experiments, quantitative NMR spectroscopy (qNMR) was used to measure concentration of the initial 100% DMSO compound solutions and, using the same fitting method, $qK_d$ values were determined.

BIOLOGICAL DATA TABLE 3

| Cpd No. | MGL mutant ThermoFluor $K_d$ (μM) |
|---|---|
| 1 | 0.006 |
| 2 | 0.022 |
| 3 | 0.0333 |
| 4 | 0.143 |
| 5 | 0.0112 |
| 7 | 0.010 |
| 8 | 0.128 |
| 9 | 0.014 |
| 11 | 0.044 |
| 12 | 0.051 |
| 13 | 0.050 |
| 14 | 0.086 |
| 17 | 0.333 |
| 18 | 0.215 |
| 27 | 0.446 |
| 31 | 0.154 |
| 39 | 0.222 |

BIOLOGICAL DATA TABLE 3-continued

| Cpd No. | MGL mutant ThermoFluor $K_d$ (μM) |
|---|---|
| 43 | 3.33 |
| 45 | 0.833 |
| 46 | 3.40 |
| 47 | 2.50 |
| 48 | >31 |
| 49 | 0.0319 |
| 50 | 0.0007 |
| 51 | 0.00220 |
| 52 | 0.0734 |
| 56 | 0.00215 |
| 58 | 0.0666 |
| 61 | 0.0333 |
| 64 | 0.020 |
| 67 | 0.0107 |
| 68 | 0.0033 |
| 70 | 0.0035 |
| 71 | 0.050 |
| 72 | 0.0332 |
| 73 | 0.0313 |
| 74 | 0.0013 |
| 75 | 0.007 |
| 76 | 0.010 |
| 77 | 0.1 |
| 78 | 0.040 |
| 79 | 0.0333 |
| 80 | 0.192 |
| 81 | 0.016 |
| 82 | 0.105 |
| 84 | 0.060 |
| 85 | 0.0250 |
| 87 | 0.040 |
| 92 | 0.1 |
| 93 | 0.0769 |
| 94 | 0.091 |
| 99 | 0.0027 |
| 100 | 0.047 |
| 101 | 0.004 |
| 102 | 0.016 |
| 103 | 0.033 |
| 104 | 0.215 |
| 105 | 3.64 |

In Vivo Methods

Example 4

CFA-Induced Paw Radiant Heat Hypersensitivity

Each rat was placed in a test chamber on a warm glass surface and allowed to acclimate for approximately 10 min. A radiant thermal stimulus (beam of light) was focused through the glass onto the plantar surface of each hind paw in turn. The thermal stimulus was automatically shut off by a photoelectric relay when the paw was moved or when the cut-off time was reached (20 sec for radiant heat at ~5 amps). An initial (baseline) response latency to the thermal stimulus was recorded for each animal prior to the injection of complete Freund's adjuvant (CFA). Twenty-four hours following intraplantar CFA injection, the response latency of the animal to the thermal stimulus was re-evaluated and compared to the animal's baseline response time. Only rats that exhibited at least a 25% reduction in response latency (i.e., are hyperalgesic) were included in further analysis. Immediately following the post-CFA latency assessment, the indicated test compound or vehicle was administered orally. Post-compound treatment withdrawal latencies were assessed at fixed time intervals, typically 30, 60, 120, 180, and 300 min.

The percent reversal (% R) of hypersensitivity was calculated in one of two different ways: 1) using group mean values or 2) using individual animal values. More specifically:

Method 1.

For all compounds, the % R of hypersensitivity was calculated using the mean value for groups of animals at each time point according to the following formula:

% reversal=[(group treatment response−group CFA response)/(group baseline response−group CFA response)]×100

Results were given for the maximum % reversal observed for each compound at any time point tested.

Method 2.

For some compounds, the % R of hypersensitivity was calculated separately for each animal according to the following formula:

% reversal=[(individual treatment response−individual CFA response)/(individual baseline response−individual CFA response)]×100.

Results are given as a mean of the maximum % reversal values calculated for each individual animal.

BIOLOGICAL DATA TABLE 4

| Cpd No. | dose (mg/kg, p.o.) | vehicle | no. of animals | last time point (min) | Method 1: peak % reversal | Method 2: peak % reversal |
|---|---|---|---|---|---|---|
| 1 | 10 | HPβCD | 8 | 300 | −18.6 | −19.0 |
| 1 | 30 | HPβCD | 8 | 300 | 10.3 | 7.4 |
| 2 | 30 | HPβCD | 8 | 300 | 47.9 | |
| 5 | 30 | HPβCD | 9 | 300 | 57.4 | 55.8 |
| 17 | 30 | HPβCD | 8 | 180 | 27 | 31.5 |
| 56 | 30 | HPβCD | 8 | 300 | −1.3 | |
| 67 | 30 | HPβCD | 8 | 300 | 35.7 | |
| 70 | 10 | HPβCD | 8 | 300 | 28.2 | 22.5 |
| 70 | 30 | HPβCD | 8 | 300 | 4.7 | 5 |
| 76 | 10 | HPβCD | 8 | 300 | 15.7 | 26.7 |
| 76 | 30 | HPβCD | 8 | 300 | 17.1 | 17.7 |
| 77 | 30 | HPβCD | 8 | 180 | 9.9 | 6.9 |
| 79 | 30 | HPβCD | 8 | 300 | 33.7 | |
| 99 | 30 | HPβCD | 8 | 300 | 27.6 | |
| 101 | 30 | HPβCD | 8 | 300 | 6.1 | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

We claim:

1. A compound of Formula (I)

Formula (I)

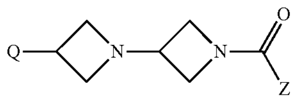

wherein

Q is selected from

Q1

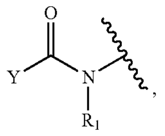

-continued

Q2

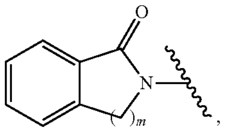, or

Q3

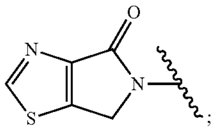;

wherein

Y is $C_{6-10}$ aryl or a heteroaryl that is thiazolyl, pyrrolyl, or oxazolyl;

$R^1$ is hydrogen or $C_{1-4}$ alkyl; and m is an integer from 1 to 3;

Z is $C_{6-10}$aryl or a heteroaryl selected from the group consisting of quinolinyl, benzothiophenyl, benzoxazolyl, benzothiazolyl, benzimidazolyl, indolyl, and indazolyl;

wherein Z is (i) optionally independently substituted with one to three substituents selected from the group consisting of $C_{1-4}$ alkyl, fluoro, chloro, bromo, trifluoromethyl, and piperidin-1-yl; provided that no more than one substituent on Z is piperidin-1-yl or (ii) (a) substituted with

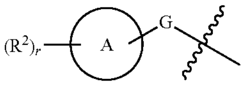

and (b) optionally further substituted with one additional methyl, chloro, fluoro, or phenyl substituent;

wherein ring A is phenyl, thienyl, or benzothiophenyl; provided that when ring A is thienyl or benzothiophenyl, G is a bond or —$CH_2$— or when A is phenyl, G is selected from the group consisting of a bond, O, —$CH_2$—, $SO_2$, and C(O); and $R^2$ is trifluoromethyl, fluoro, chloro, or methanesulfonyl;

r is an integer from 0 to 3;

and enantiomers, diastereomers, and pharmaceutically acceptable salts thereof.

2. The compound of claim 1 wherein Q is selected from

Q1

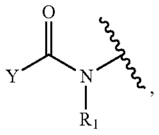,

Q2

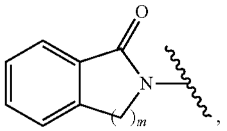, or

-continued

Q3

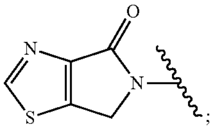;

wherein

Y is phenyl or thiazolyl;

$R^1$ is hydrogen or methyl; and m is 1.

3. The compound of claim 2 wherein $R^1$ is hydrogen.

4. The compound of claim 1 wherein Z is $C_{6-10}$aryl or a heteroaryl selected from the group consisting of benzothiophenyl, benzoxazolyl, benzothiazolyl, indolyl, and indazolyl;

wherein Z is (i) independently substituted with one to two substituents selected from the group consisting of $C_{1-4}$ alkyl, fluoro, chloro, bromo, trifluoromethyl, and piperidin-1-yl; provided that no more than one substituent on Z is piperidin-1-yl or (ii) (a) substituted with

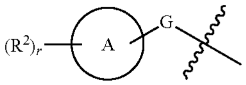

and (b) optionally further substituted with one additional methyl, chloro, fluoro, or phenyl substituent;

wherein ring A is phenyl, thienyl, or benzothiophenyl; provided that when ring A is thienyl or benzothiophenyl, G is a bond or —$CH_2$— or when ring A is phenyl G is a bond, O, —$CH_2$—, $SO_2$, or C(O); and $R^2$ is trifluoromethyl, fluoro, chloro, or methanesulfonyl; and r is an integer from 0 to 3.

5. The compound of claim 4 wherein Z is $C_{6-10}$aryl or a heteroaryl selected from the group consisting of benzothiophenyl, benzoxazolyl, benzothiazolyl, indolyl, and indazolyl;

wherein Z is (i) optionally independently substituted with one to two substituents selected from the group consisting of $C_{1-4}$ alkyl, fluoro, chloro, bromo, and trifluoromethyl or (ii) (a) substituted with

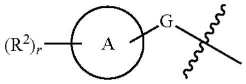

and (b) optionally further substituted with one additional methyl, chloro, fluoro, or phenyl substituent;

wherein ring A is phenyl or thienyl; provided that when ring A is phenyl, G is a bond, —$CH_2$—, or $SO_2$ or when ring A is thienyl, G is a bond or —$CH_2$—; and $R^2$ is trifluoromethyl, fluoro, chloro, or methanesulfonyl; and r is an integer from 0 to 2.

6. A compound of Formula (I)

Formula (I)

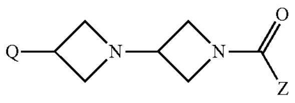

wherein:

Q is selected from

Q1

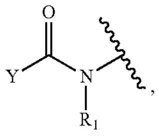

Q2

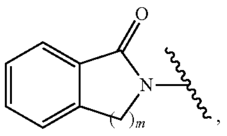

or

Q3

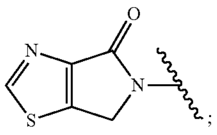

wherein

Y is phenyl or thiazolyl;

$R^1$ is hydrogen or methyl; and m is 1;

Z is $C_{6-10}$aryl or a heteroaryl selected from the group consisting of benzothiophenyl, benzoxazolyl, benzothiazolyl, indolyl, and indazolyl;

wherein Z is (i) independently substituted with one to two substituents selected from the group consisting of $C_{1-4}$ alkyl, fluoro, chloro, bromo, trifluoromethyl, and piperidin-1-yl; provided that no more than one substituent on Z is piperidin-1-yl or (ii) (a) substituted with

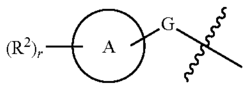

and (b) optionally further substituted with one additional methyl, chloro, fluoro, or phenyl substituent;

wherein ring A is phenyl, thienyl, or benzothiophenyl; provided that when ring A is thienyl or benzothiophenyl, G is a bond or $-CH_2-$ or when ring A is phenyl, G is a bond, 0, $-CH_2-$, $SO_2$, or C(O); and $R^2$ is trifluoromethyl, fluoro, chloro, or methanesulfonyl; and r is an integer from 0 to 3;

and enantiomers, diastereomers, and pharmaceutically acceptable salts thereof.

7. A compound of Formula (I)

Formula (I)

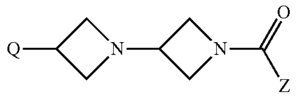

wherein:

Q is selected from

Q1

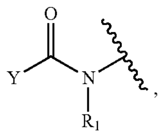

Q2

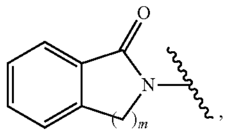

or

Q3

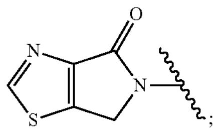

wherein

Y is phenyl or thiazolyl;

$R^1$ is hydrogen; and m is 1;

Z is $C_{6-10}$aryl or a heteroaryl selected from the group consisting of benzothiophenyl, benzoxazolyl, benzothiazolyl, indolyl, and indazolyl;

wherein Z is (i) independently substituted with one to two substituents selected from the group consisting of $C_{1-4}$ alkyl, fluoro, chloro, bromo, and trifluoromethyl or (ii) (a) substituted with

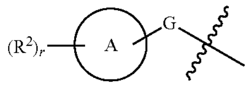

and (b) optionally further substituted with one additional methyl, chloro, fluoro, or phenyl substituent;

wherein ring A is phenyl or thienyl; provided that when ring A is thienyl, G is a bond or $-CH_2-$ or when ring A is phenyl G is a bond, $-CH_2-$, or $SO_2$;

$R^2$ is trifluoromethyl, fluoro, chloro, or methanesulfonyl; and r is an integer from 0 to 2;

and enantiomers, diastereomers, and pharmaceutically acceptable salts thereof.

8. A compound of Formula (Ib)

Formula (Ib)

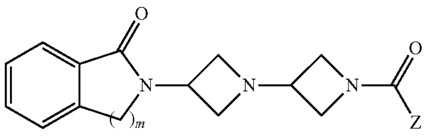

selected from the group consisting of
a compound wherein m is 1, and Z is 3-chloro-6-phenyl-benzothiophen-2-yl;
a compound wherein m is 1, and Z is 6-phenyl-naphth-2-yl;
a compound wherein m is 1, and Z is 1-(4-trifluoromethylphenyl)-1H-indol-5-yl;
a compound wherein m is 1, and Z is 1-(phenylsulfonyl)-1H-indol-5-yl;
a compound wherein m is 1, and Z is 6-(3-methanesulfonylphenyl)-benzothiophen-2-yl;
a compound wherein m is 1, and Z is 3-chloro-6-bromo-benzothiophen-2-yl;
a compound wherein m is 1, and Z is 3,6-diphenyl-benzothiophen-2-yl;
a compound wherein m is 1, and Z is 1-(3-trifluoromethylphenyl)-1H-indol-5-yl;
a compound wherein m is 1, and Z is 4-(5-trifluoromethyl-thien-2-yl)-phenyl;
a compound wherein m is 1, and Z is 2-phenyl-benzoxazol-5-yl;
a compound wherein m is 1, and Z is 2-(3-trifluoromethylphenyl)-benzoxazol-6-yl;
a compound wherein m is 1, and Z is 5-phenyl-benzothiophen-2-yl;
a compound wherein m is 1, and Z is 4-(3-methanesulfonylphenyl)phenyl;
a compound wherein m is 1, and Z is 6-trifluoromethyl-benzothiophen-2-yl;
a compound wherein m is 1, and Z is 5-(3-methanesulfonylphenyl)benzothiophen-2-yl;
a compound wherein m is 1, and Z is 5-bromo-naphth-2-yl;
a compound wherein m is 1, and Z is 2-phenyl-benzoxazol-6-yl;
a compound wherein m is 1, and Z is 1-phenyl-1H-indol-5-yl;
a compound wherein m is 1, and Z is 4-(3-trifluoromethylphenylmethyl)phenyl;
a compound wherein m is 1, and Z is 6-bromo-benzothiophen-2-yl;
a compound wherein m is 1, and Z is 2-(4-chlorophenyl)-benzoxazol-6-yl;
a compound wherein m is 1, and Z is 1-(2-trifluoromethylphenyl)-1H-indol-5-yl;
a compound wherein m is 1, and Z is 6-bromo-naphth-2-yl;
a compound wherein m is 1, and Z is 4-piperadin-1-yl-phenyl;
a compound wherein m is 1, and Z is 4-phenyl-phenyl;
a compound wherein m is 1, and Z is 5-bromo-benzothiophen-2-yl;
a compound wherein m is 1, and Z is 4-(phenylmethyl)phenyl;
a compound wherein m is 1, and Z is 4-(benzothiophen-2-yl)phenyl
a compound wherein m is 1, and Z is 4-bromophenyl;
a compound wherein m is 1, and Z is 5-phenyl-naphth-2-yl;
a compound wherein m is 1, and Z is 6-phenyl-benzothiophen-2-yl;
a compound wherein m is 1, and Z is 3-chloro-6-trifluoromethyl-benzothiophen-2-yl;
a compound wherein m is 1, and Z is 3-chloro-6-fluoro-benzothiophen-2-yl;
a compound wherein m is 1, and Z is 3-methyl-6-trifluoromethyl-benzothiophen-2-yl; and
a compound wherein m is 1, and Z is 1-(4-fluorophenyl)-1H-indol-5-yl;
and pharmaceutically acceptable salt forms thereof.

9. A compound of Formula (Ic)

Formula (Ic)

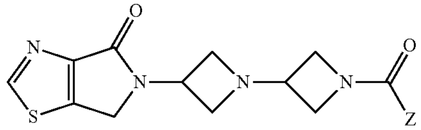

selected from the group consisting of
a compound wherein Z is 3-methyl-6-trifluoromethyl-benzothiophen-2-yl;
a compound wherein Z is 2-methyl-4-(3-trifluoromethylphenyl)phenyl;
a compound wherein Z is 2-methyl-4-(4-trifluoromethylphenyl)phenyl; and
a compound wherein Z is 1-(4-trifluoromethylphenyl)-1H-indol-5-yl;
and pharmaceutically acceptable salt forms thereof.

10. A pharmaceutical composition comprising a compound of claim 1 and at least one of a pharmaceutically acceptable carrier, a pharmaceutically acceptable excipient, and a pharmaceutically acceptable diluent.

11. A pharmaceutical composition of claim 10, wherein the composition is a solid oral dosage form.

12. A pharmaceutical composition of claim 10, wherein the composition is a syrup, an elixir, or a suspension.

* * * * *